US010126291B2

(12) United States Patent
Yu et al.

(10) Patent No.: US 10,126,291 B2
(45) Date of Patent: Nov. 13, 2018

(54) APPARATUS FOR DISEASE DETECTION

(71) Applicants: Chris C Yu, Conneautville, PA (US); Xuedong Du, Shanghai (CN); He Yu, Honolulu, HI (US)

(72) Inventors: Chris C Yu, Conneautville, PA (US); Xuedong Du, Shanghai (CN); He Yu, Honolulu, HI (US)

(73) Assignee: AnPac Bio-Medical Science Co., Ltd., Tortola (VG)

( * ) Notice: Subject to any disclaimer, the term of this patent is extended or adjusted under 35 U.S.C. 154(b) by 231 days.

(21) Appl. No.: 13/856,935

(22) Filed: Apr. 4, 2013

(65) Prior Publication Data
US 2014/0342441 A1    Nov. 20, 2014

Related U.S. Application Data
(62) Division of application No. 13/807,859, filed on Feb. 18, 2013.

(51) Int. Cl.
*B01L 3/00* (2006.01)
*G01N 33/50* (2006.01)

(52) U.S. Cl.
CPC ........ *G01N 33/50* (2013.01); *B01L 3/502707* (2013.01); *B01L 3/502761* (2013.01); *B01L 2200/0647* (2013.01); *B01L 2200/0652* (2013.01); *B01L 2200/0663* (2013.01); *B01L 2200/0668* (2013.01); *B01L 2400/043* (2013.01); *B01L 2400/0415* (2013.01); *B01L 2400/0487* (2013.01)

(58) Field of Classification Search
CPC .............. G01N 33/50; B01L 3/502707; B01L 3/502761; B01L 2200/0652; B01L 2200/0663; B01L 2200/0668; B01L 2400/0415; B01L 2400/043; B01L 2400/0487
See application file for complete search history.

(56) References Cited

U.S. PATENT DOCUMENTS

| | | | |
|---|---|---|---|
| 5,976,466 A | 11/1999 | Ratner et al. | |
| 6,583,044 B2 * | 6/2003 | Bahl et al. | 438/619 |
| 2008/0093229 A1 * | 4/2008 | Lim et al. | 205/792 |
| 2008/0286750 A1 * | 11/2008 | Xu | G01N 33/48728 435/4 |
| 2009/0116207 A1 | 5/2009 | Lim et al. | |
| 2009/0131905 A1 * | 5/2009 | Allen et al. | 604/501 |
| 2009/0131995 A1 | 5/2009 | Sloan et al. | |

(Continued)

FOREIGN PATENT DOCUMENTS

WO    WO 2008-066965    6/2008

*Primary Examiner* — Erik B Crawford
(74) *Attorney, Agent, or Firm* — Weisun Rao; Greenberg Traurig, LLP

(57) ABSTRACT

The present invention provides, among others, apparatus for detecting a disease, comprising a system delivery biological subject and a probing and detecting device, wherein the probing and detecting device includes a first micro-device and a first substrate supporting the first micro-device, the first micro-device contacts a biologic material to be detected and is capable of measuring at the microscopic level an electric, magnetic, electromagnetic, thermal, optical, acoustical, biological, chemical, physical, or mechanical property of the biologic material.

103 Claims, 58 Drawing Sheets

(56) References Cited

U.S. PATENT DOCUMENTS

| | | | |
|---|---|---|---|
| 2009/0156427 A1 | 6/2009 | Zhang et al. | |
| 2011/0200948 A1* | 8/2011 | Yu .................. | B81C 1/00119 430/314 |
| 2011/0227558 A1* | 9/2011 | Mannion ............... | B82Y 30/00 324/71.1 |

* cited by examiner

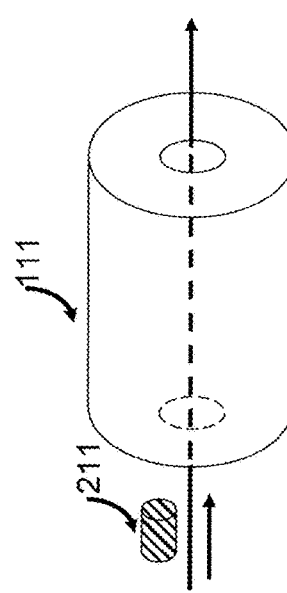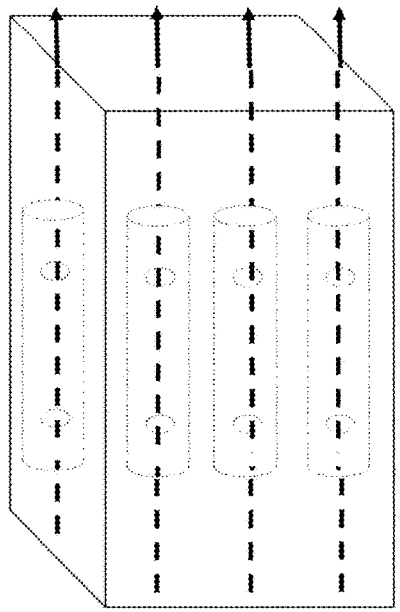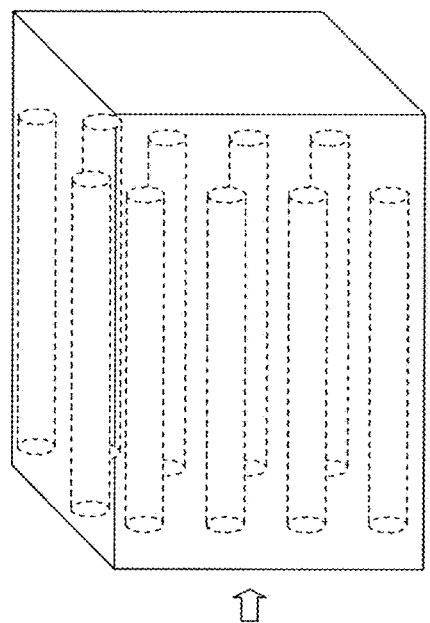
FIGURE 1

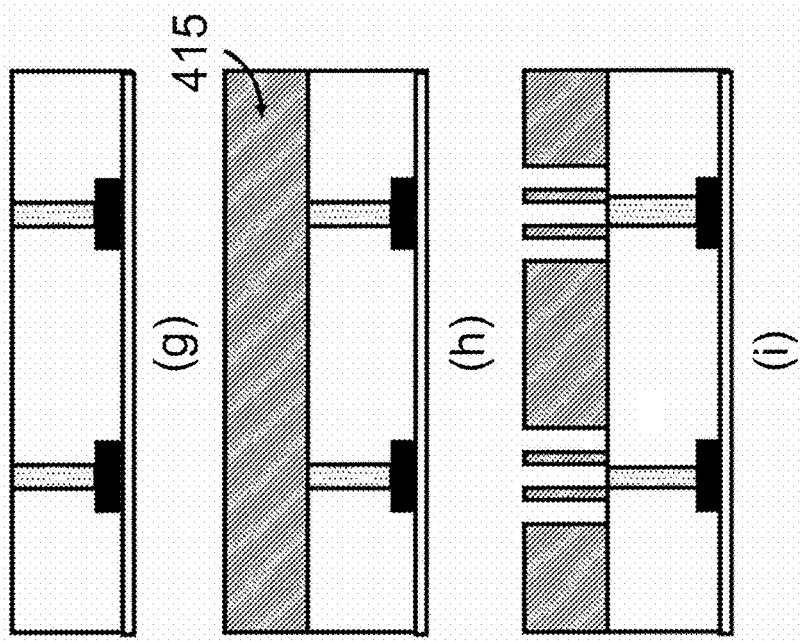
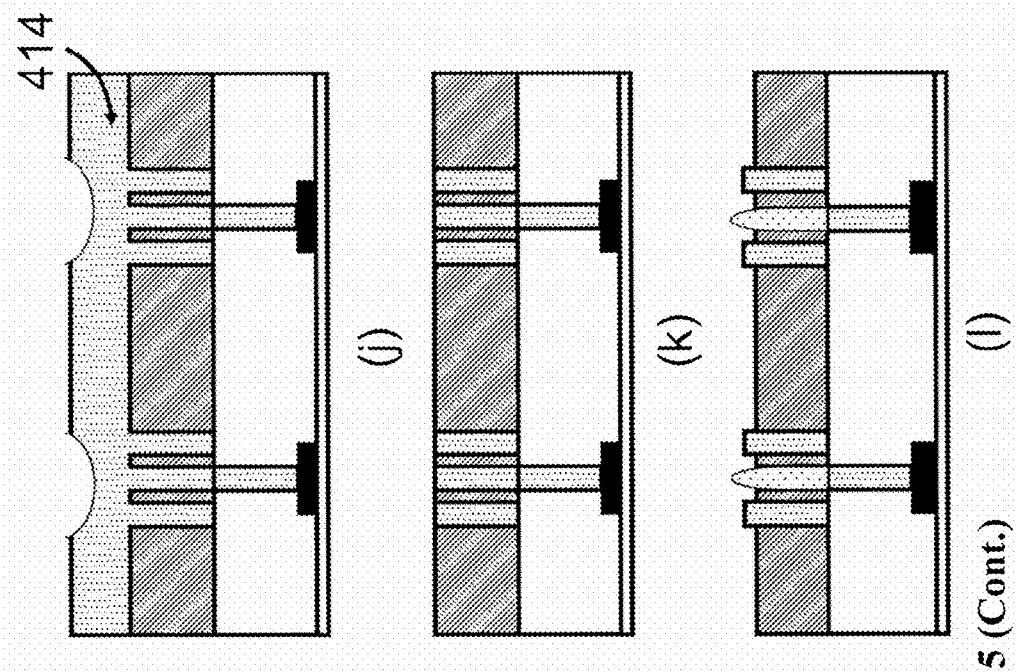
FIGURE 5 (Cont.)

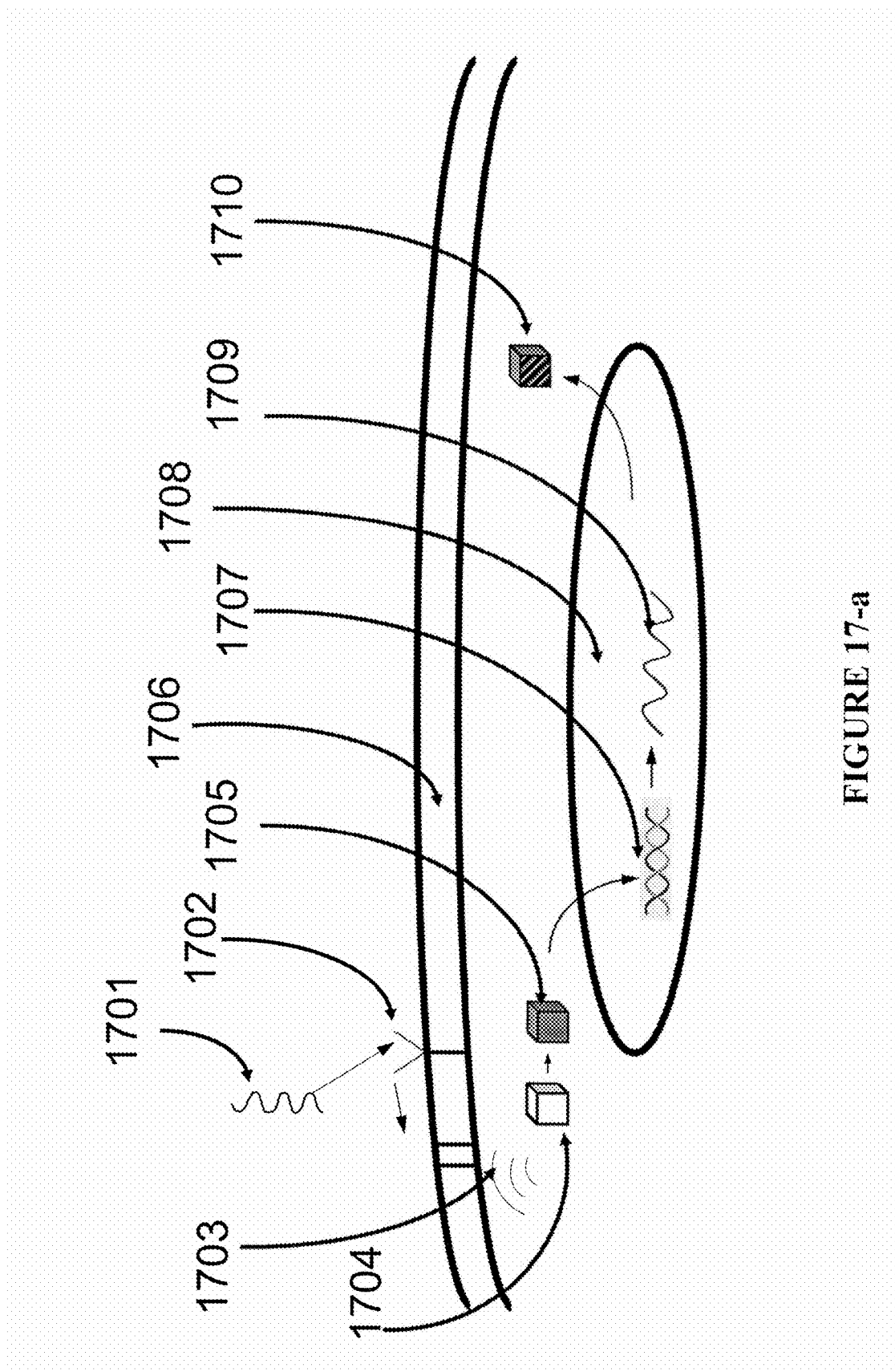
FIGURE 17-a

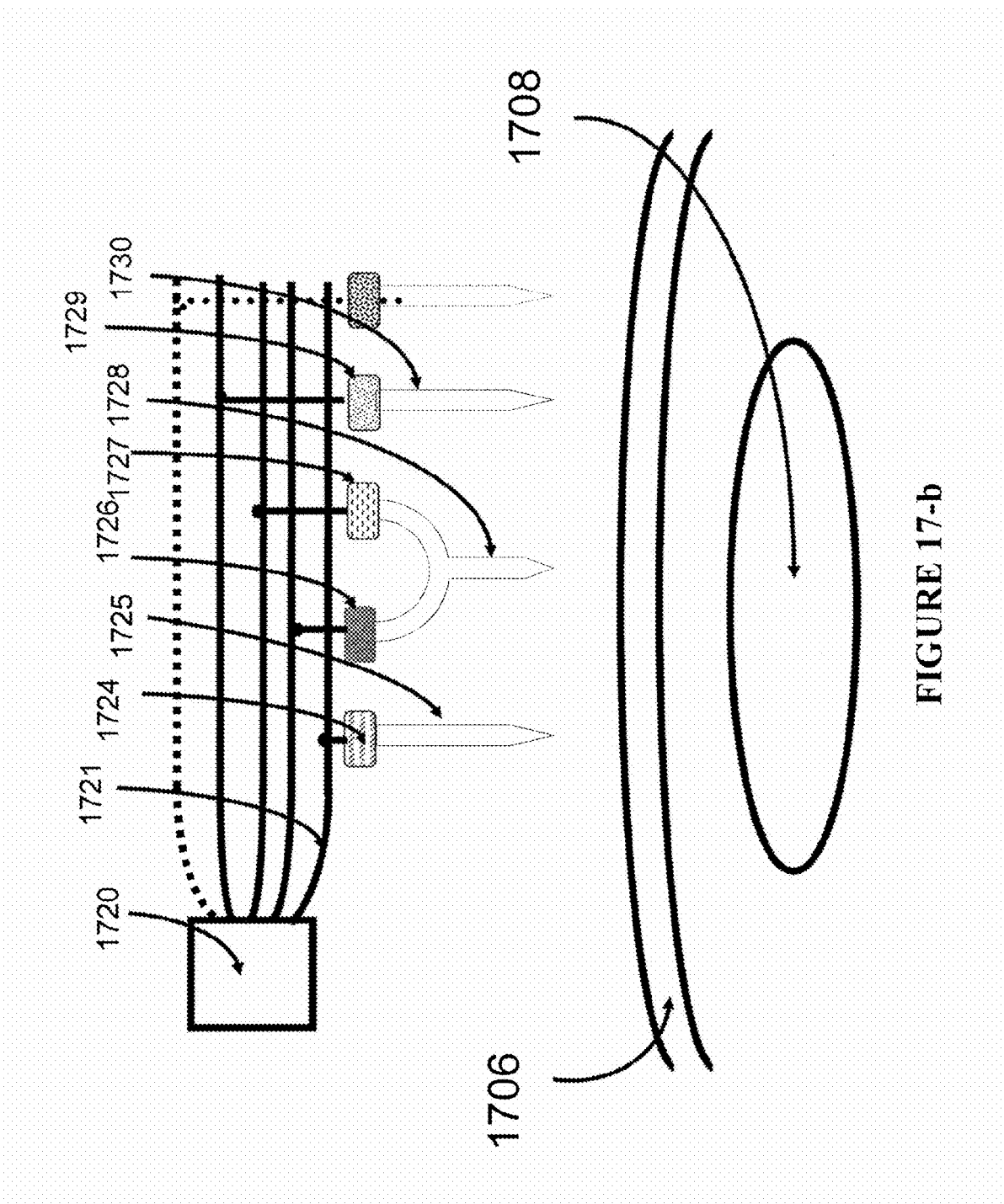

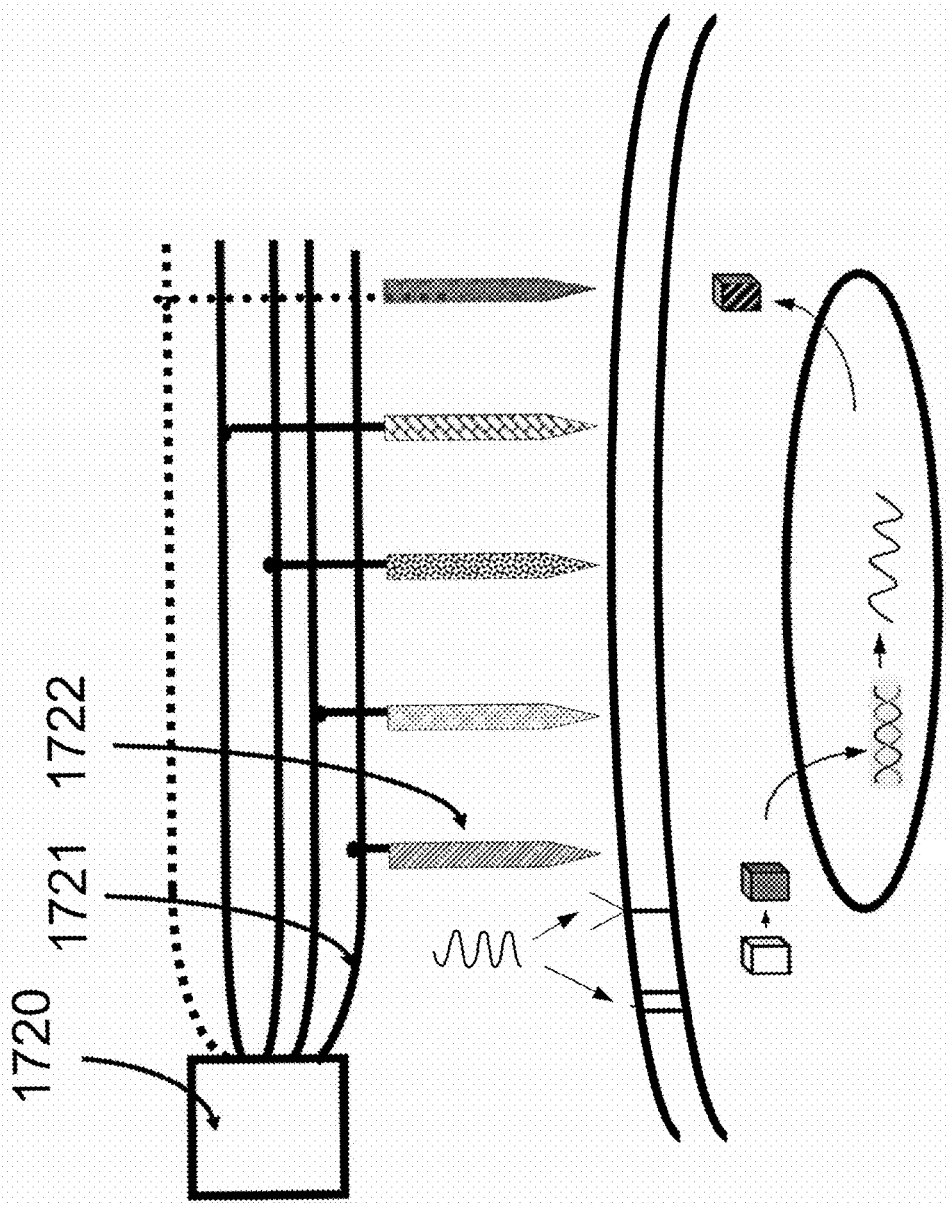
FIGURE 17-c

Detecting device covered with transparent panel

APPARATUS FOR DISEASE DETECTION

CROSS REFERENCE TO RELATED APPLICATIONS

This application is a divisional application of and claims priority to U.S. application Ser. No. 13/807,859, filed on Dec. 31, 2012, the entire contents of which are incorporated herein by reference.

This application is a national phase application and claims the benefit, under 35 U.S.C. § 371, of PCT/US2011/042637, filed on Jun. 30, 2011, which in turn claims priority to U.S. Application No. 61/360,041, filed on Jun. 30, 2010; U.S. Application No. 61/389,960, filed on Oct. 5, 2010; U.S. Application No. 61/430,641, filed on Jan. 7, 2011; U.S. Application No. 61/467,097, filed on Mar. 24, 2011; and U.S. Application No. 61/498,954, filed on Jun. 20, 2011; the contents of all of which are incorporated herein by reference in their entireties.

BACKGROUND OF THE INVENTION

Many serious diseases with high morbidity and mortality, including cancer and heart diseases, are very difficult to diagnose early and accurately. Current disease diagnosis technologies typically rely on macroscopic data and information such as body temperature, blood pressure, and scanned images of the body. To detect serious diseases such as cancer, many of the diagnosis apparatus commonly used today are based on imaging technologies, including x-ray, CT scan, and nuclear magnetic resonance (NMR). While they provide various degrees of usefulness in disease diagnosis, most of them cannot provide accurate, totally safe, and cost-effective diagnosis of such serious diseases as cancer at an early stage. Further, many of the existing diagnosis techniques and related apparatus are invasive and sometimes not readily accessible, especially in remote regions or rural areas.

Even the newly emerged DNA tests have not been proven effective in diagnosing a wide range of diseases in a rapid, reliable, accurate, and cost-effective manner. In recent years, there have been some efforts in using nano technologies for various biological applications, with most of the work focused on gene mapping and moderate developments in the field of disease detection. For instance, Pantel et al. discussed the use of a MicroEelectroMechanical Systems (MEMS) sensor for detecting cancer cells in blood and bone marrow in vitro (see, e.g., Klaus Pantel et al., *Nature Reviews,* 2008, 8, 329); Kubena et al. disclose in U.S. Pat. No. 6,922,118 the deployment of MEMS for detecting biological agents; and Weissman et al. disclose in U.S. Pat. No. 6,330,885 utilizing MEMS sensor for detecting accretion of biological matter.

However, to date, most of the above described technologies have been limited to isolated examples for sensing, using systems of relatively simple constructions and large dimensions but often with limited functions, and lack sensitivities and specificities. Further, some existing technologies utilizing nano-particles and biological approaches have the drawbacks of requiring complicated sample preparation procedures (such as using chemical or biological markers), difficulty in data interpretation, and too much reliance on visual and color change as means of diagnosis (which is subjective and of limited resolution), making them unsuitable for early stage disease detection, e.g., for such serious diseases as cancer.

These drawbacks call for novel solutions that not only overcome them but also bring enhanced accuracy, specificity, efficiency, non-invasiveness, and speed in early-stage disease detection at reduced costs.

SUMMARY OF THE INVENTION

The present invention in general relates to a class of innovative disease detection apparatus which utilizes novel micro-devices (or functionalities) integrated onto them for carrying out diagnosis at microscopic levels, in vivo or in vitro, on a single cell, a single biological molecular (e.g., DNA, RNA, or protein), a single biological subject (e.g., a single virus), or other sufficiently small unit or fundamental biological composition. These apparatus can be made by using state-of-the-art micro-device fabrication technologies and novel process flows such as integrated circuit fabrication technologies. As used herein, the term "disease detection apparatus" can be interchanged with such terms as disease detection device or apparatus integrated with micro-devices, or any other similar terms of the same meaning. Apparatus of this invention containing multiple micro-devices can detect multiple parameters of a biological sample to be analyzed. These disease detection apparatus are capable of detecting diseases at their early stages with a high degree of sensitivity, specificity, speed, convenience (e.g., reduced apparatus size), or affordability (e.g., reduced costs).

One key component of the detection apparatus is a class of novel micro-devices and their inventive fabrication processes which enable these novel micro-devices to perform at a much higher level than those of conventional disease detection apparatus or technologies, due to much improved detection sensitivity, specificity, and speed. Examples of fabrication techniques that can be used to make the micro-devices described herein include but not limited to mechanical, chemical, physical-chemical, chemical mechanical, biophysical, bio-physical mechanical, electro-mechanical, bio-electro-mechanical, micro-electro-mechanical, electro-chemical-mechanical, electro-bio-chemical-mechanical, nano-fabrication techniques, integrated circuit and semiconductor manufacturing techniques and processes. For a general description of some of the applicable fabrication technologies, see, e.g., R. Zaouk et al., *Introduction to Microfabrication Techniques,* in Microfluidic Techniques (S. Minteer, ed.), 2006, Humana Press; *Microsystem Engineering of Lab-on-a-chip Devices,* 1st Ed. (Geschke, Klank & Telleman, eds.), John Wiley & Sons., 2004. Micro-device functionalities would at least include sensing, detecting, measuring, diagnosing, monitoring, and analyzing for disease diagnosis. Multiple micro-devices can be integrated onto a piece of detection apparatus to make the apparatus more advanced and sophisticated for further enhanced measurement sensitivity, specificity, speed and functionalities, with ability to measure the same parameter or a set of different parameters.

Optional components of the apparatus includes means to perform at least the function of addressing, controlling, forcing, receiving, amplifying, or storing information from each probe. Such means can be, e.g., a central control unit that includes a controlling circuitry, an addressing unit, an amplifier circuitry, a logic processing circuitry, a memory unit, an application specific chip, a signal transmitter, a signal receiver, or a sensor.

Specifically, one aspect of this invention provides apparatus for detecting a disease, each comprising a first micro-device and a first substrate supporting the first micro-device, wherein the first micro-device contacts a biological subject to be analyzed and is capable of measuring at the microscopic level an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electrochemical, bio-electro-chemical-mechanical, physical, or mechanical property of the biologic material. The apparatus can further optionally include a device for reading the data from measuring the property.

In some embodiments, the difference in the measured property of the tested biologic material and that of a biologic sample from a subject free of the disease is indicative of the possible occurrence of the disease in early stage.

In some other embodiments, the electrical property is surface charge, surface potential, oscillation in electrical signal (e.g., oscillation in ions, pulsing electrical field, pulsing surface charge, pulsing voltage), electrical field, electrical field distribution, electrical charge distribution, or impedance; the thermal property is temperature; the chemical property is pH value, ionic strength, bonding strength; the physical property is density; and the mechanical property is hardness, shear strength, elongation strength, fracture stress, adhesion, elasticity, or density.

In some other embodiments, each of the apparatus further comprises at least one or more additional micro-devices. In these embodiments, each of the micro-devices contained in the apparatus comprises a conductive material, an electrically insulating material, or a semiconductor material; and each of the micro-devices can comprise the same or different material(s) and can measure the same or different properties at the same or different time. These multiple micro-devices can be spaced out, e.g., with a distance of at least 10 angstroms on the substrate. The multiple micro-devices integrated in a disease detection apparatus can sequentially and/or simultaneously measure various parameters from a biological subject being detected at macroscopic and/or microscopic levels. Sometimes, in an apparatus with multiple micro-devices, some micro-devices can act as probing devices to disturb the biological subject and trigger a response from the biological subject, while other micro-devices in the apparatus can act as detection devices to measure the triggered response by the biological subject.

In some other embodiments, each of the micro-devices has the size ranging from about 1 angstrom (Å) to about 5 millimeter (e.g., from 5 Å to 1 millimeter).

In some other embodiments, the apparatus comprises one or more additional substrates on which the micro-devices are placed. Each of the substrates can comprise the same or a different material (e.g., a conductive material or an insulator), can be in the same or a different shape (e.g., a slab or a tube), and each substrate can be a two- or three-dimensional object. They can take the form of cylinder, slabs, or any other desired shapes and configurations, in order to further improve their measurement sensitivity, specificity, speed, sample size, and reduce cost and size.

In terms of detection apparatus to integrate micro-devices, in one novel detection apparatus design, to increase measurement sensitivity, micro-devices mounted on two slabs separated by a small spacing with sample to be measured between the two said slabs can be used to detect disease with improved speed, with micro-devices measuring cells, DNAs, and desired items in the sample in parallel. The surface area of the slabs can be maximized in order to have maximum number of micro-devices placed on the slabs and enhance measurement efficiency and speed. Optionally, multiple micro-devices integrated on the surface of the slabs can be closely spaced with their spacing matching that of cells, DNAs, and items to be measured.

In another novel configuration, a detection apparatus integrated with micro-devices is shaped in the form of a cylinder, with multiple micro-devices with detection probes integrated/mounted in the inter surfaces of the cylinder and with sample to be measured (such as blood) flowing through the cylinder.

In yet another innovative configuration, a detection apparatus with integrated micro-devices is shaped in the form of a rectangular pipe, with multiple micro-devices with detection probes integrated/mounted in the inter surfaces of the pipe and with sample to be measured (such as blood) flowing through the rectangular pipe.

In another aspect, the invention provides another set of apparatus for detecting a disease in a biological subject, comprising a system for delivering the biological subject to be detected and a probing and detecting device for probing and detecting the biological subject.

The difference in the measured property of the detected biologic material and of a standard biologic sample is indicative of the possible occurrence of the disease.

In some embodiments, the probing and detecting device comprises a first micro-device and a first substrate supporting the first micro-device, the first micro-device contacts the biologic subject to be detected and is capable of measuring at the microscopic level an electric, magnetic, electromagnetic, thermal, optical, acoustical, biological, chemical, electro-mechanical, electro-chemical, electro-chemical-mechanical, bio-chemical, bio-chemical-physical, bio-mechanical, bio-electro-mechanical, bio-electro-chemical, bio-electro-chemical-mechanical, physical, or mechanical property of the biologic subject. For example, the electrical property can be surface charge, surface potential, resting potential, electrical current, electrical field distribution, electric dipole, electric quadruple, three-dimensional electrical or charge cloud distribution, electrical properties at telomere of DNA and chromosome, or impedance; the thermal property can be temperature, or vibrational frequency of biological item or molecules; the optical property can be optical absorption, optical transmission, optical reflection, optical-electrical property, brightness, or fluorescent emission; the chemical property can be pH value, chemical reaction, bio-chemical reaction, bio-electro-chemical reaction, reaction speed, reaction energy, oxygen concentration, oxygen consumption rate, ionic strength, catalytic behavior, or bonding strength; the physical property can be density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

In some embodiments of the apparatus, the probing and detecting device applies to the biological subject a voltage ranging from about 1 mV to about 10 V, or from about 1 mV to about 1.0 V.

In some embodiments of the apparatus, the first micro-device comprises a conductive material, an electrically insulating material, a biological material, or a semiconductor material.

In some embodiments of the apparatus, the first micro-device has a size ranging from about 1 angstrom to about 5 millimeter.

In some embodiments of the apparatus, the probing and detecting device further comprises one or more additional micro-devices, each of which is also capable of measuring at the microscopic level an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical property of the biologic entity. The electrical property can be surface charge, surface potential, resting potential, electrical current, electrical field distribution, electric dipole, electric quadruple, three-dimensional electrical or charge cloud distribution, electrical properties at telomere of DNA and chromosome, or impedance; the thermal property can be temperature, or vibrational frequency of biological item or molecules; the optical property can be optical absorption, optical transmission, optical reflection, optical-electrical property, brightness, or fluorescent emission; the chemical property can be pH value, chemical reaction, bio-chemical reaction, bio-electro-chemical reaction, reaction speed, reaction energy, oxygen concentration, oxygen consumption rate, ionic strength, catalytic behavior, or bonding strength; the physical property can be density or geometric size; the acoustic property can be frequency, speed of acoustic waves, acoustic frequency and intensity spectrum distribution, acoustic intensity, acoustical absorption, or acoustical resonance; and the mechanical property can be internal pressure, hardness, shear strength, elongation strength, fracture stress, adhesion, mechanical resonance frequency, elasticity, plasticity, or compressibility.

In some embodiments of the apparatus, each of the additional micro-devices comprises a conductive material, an electrically insulating material, a biological material, or a semiconductor material. Further, each of the additional micro-devices comprises a material that is the same as or different from the material of the first micro-device and is capable of measuring the same or different property of the biologic subject as the first-micro-device does.

In some embodiments of the apparatus, the first micro-device and each of the additional micro-devices are capable of measuring the surface charge, surface potential, resting potential, electrical current, electrical field distribution, electric dipole, electric quadruple, three-dimensional electrical or charge cloud distribution, electrical properties at telomere of DNA and chromosome, impedance, temperature, vibrational frequency, optical absorption, optical transmission, optical reflection, optical-electrical property, brightness, fluorescent emission, pH value, chemical reaction, bio-chemical reaction, bio-electro-chemical reaction, reaction speed, reaction energy, oxygen concentration, oxygen consumption rate, ionic strength, catalytic behavior, bonding strength, density, geometric size, frequency, speed of acoustic waves, acoustic frequency and intensity spectrum distribution, acoustic intensity, acoustical absorption, acoustical resonance, internal pressure, hardness, shearing strength, elongation strength, fracture stress, adhesion, mechanical resonance frequency, elasticity, plasticity, or compressibility. They can measure the same or different properties at the same or different times.

In some embodiments of the apparatus, the probing device and the micro-devices are placed with a desired distance between each other.

In some embodiments of the apparatus, each of the additional micro-devices has a size ranging from about 1 angstrom to about 5 millimeter.

In some embodiments of the apparatus, the micro-devices are spaced out on the substrate by a distance of at least 10 angstroms (e.g., from about 5 microns to about 100 microns).

In some embodiments of the apparatus, the substrate is in the shape of a slab, a tube, or an array of tubes; or the substrate is a three-dimensional object.

In some embodiments of the apparatus, the probing and detecting device further comprises a second substrate of the same or different material as the first substrate.

In some embodiments, the apparatus further comprises a device for reading the data from measuring the property by the probing and detecting device.

In some embodiments, the apparatus each further comprises a system for delivering fluid which comprises a pressure generator, a pressure regulator, a throttle valve, a pressure gauge, and distributing kits. The pressure generator can include a motor piston system and a bin containing compressed gas; the pressure regulator can down-regulate or up-regulate the pressure to a desired value; the pressure gauge feeds back the measured value to the throttle valve which then regulates the pressure to approach the target value.

The fluid to be delivered in the apparatus can be a liquid or gas. Examples of the liquid include blood, urine, saliva, tear, saline, and sweat; whereas examples of the gas include nitrogen, argon, helium, neon, krypton, xenon, or radon.

In some embodiments of the apparatus, the probing and detecting device further comprises a system controller which comprises a pre-amplifier, a lock-in amplifier, an electrical meter, a thermal meter, a switching matrix, a system bus, a nonvolatile storage device, a random access memory, a processor, or a user interface. The interface may include a sensor which can be, e.g., a thermal sensor, a flow meter, or a piezo meter.

In some embodiments, the apparatus may further include a biological interface, a system controller, or at least one system for reclaiming or treatment medical waste. Reclaiming and treatment of medical waste is performed by the same system or by two different systems.

In some embodiments, the apparatus further include a testing sample delivery system, a testing sample distribution system, a distribution channel, a pre-processing unit, a detection device, a global positioning system, a motion device, a signal transmitter, a signal receiver, a sensor, a memory storage unit, a logic processing unit, an application specific chip, a testing sample recycling and reclaiming unit, a micro-electro-mechanical device, a multi-functional device, or a micro-instrument to perform surgery, cleaning, or medical function. Such additional components each may be fabricated by methods known in the art, e.g., as described in PCT/US2011/024672, U.S. application Ser. No. 12/416, 280, and PCT/US2010/041001, all of which are incorporated herein by reference in their entireties.

In some embodiments of the apparatus, the system for delivering the biological subject comprises at least one channel inside which the biological subject to be detected travels in a certain direction; the probing and detecting device comprises at least one probing micro-device and at least one detecting micro-device, at least one probing micro-device is located before at least one detecting micro-device relative to the direction in which the biological subject travels, and the probing micro-device and the detecting micro-device can be attached to the interior or exterior wall of the channel.

In some embodiments of the apparatus, the shapes and sizes of different sections of the channel can be the same or different; the width of the channel ranges from about 1 nm to about 1 mm; the channel can be straight, curved, or angled; the interior wall of the channel defines a circular, oval, or polygon space; the interior wall of the channel defines a circular or rectangular space; the channel is a circular carbon nano-tube.

In some embodiments of the apparatus, the carbon nano-tube has a diameter ranging from about 0.5 nm to about 100 nm and a length ranging from about 5.0 nm to about 10 mm.

In some embodiments of the apparatus, the interior wall of the channel has at least one concave that may be in the same section as a probing or detecting micro-device. The concave groove can be a cubic space or an angled space; the concave groove can have a depth ranging from about 10 nm to about 1 mm.

In some embodiments of the apparatus, a distribution fluid is injected into the channel, either before or after the biological subject passes a probing micro-device, to aid the traveling or separation of the biological subject inside the channel. The distribution fluid can be injected into the channel through a distribution fluid channel connected to an opening in the channel wall.

The apparatus can be for detecting the diseases of more than one biological subjects and the channel comprises a device located therein for separating or dividing the biological subjects based on different levels of a same property of the biological subjects. The separating or dividing device can be, e.g., a slit and separates or divides biological subjects based on their properties such as surface charges.

The apparatus can further include a filtering device for removing irrelevant objects from the biologic subject for detection.

The biological subject can be a DNA, telomere of DNA, RNA, chromosome, cell, cell substructure, protein, or virus.

In some embodiments, the apparatus may further includes a unit for delivering the biological subject, a channel, a detection unit, a data storage unit, a data analysis unit, a central control unit, a biological sample recirculation unit, a waste disposal unit; a pre-processing unit, a signal processing unit, or a disposal processing unit. All the additional components can be integrated on a single device or a board along with the delivering system and probing and detecting probe. The pre-processing unit may comprise a sample filtration unit; a delivery unit for delivering a desired ion, a biological component, or a bio-chemical component; a recharging unit; a constant pressure delivery unit; and a sample pre-probing disturbing unit. The sample filtration unit may comprise an entrance channel, a disturbing fluid channel, an accelerating chamber, and a slit. The signal processing unit may comprise an amplifier, a lock-in amplifier, an A/D (analog-to-digital or alternative to direct electric current) converter, a micro-computer, a manipulator, a display, and network connections. The signal processing unit may collect more than one signal, and the signals can be integrated to cancel noise or to enhance the signal to noise ratio.

In some embodiments of the apparatus, a bio-compatible fluid is injected into the disturbing fluid channel to separate the biological subject, or the bio-compatible fluid is injected from the entrance of the disturbing fluid channel and delivered to an opening in the entrance channel wall. The bio-compatible fluid comprises saline, water, an oxygen-rich liquid, or plasma.

In some embodiments of the apparatus, the angle between the entrance channel and the disturbing fluid channel ranges from about 0° to about 180°, from about 30° to about 150°, from about 60° to about 120°, or from about 75° to about 105°, or about 90°; the width of each channel ranges from about 1 nm to about 1 mm; and at least one of the channels comprises one probing device attached to the channel's sidewall, wherein the probing device is capable of measuring at the microscopic level an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property of the biological subject. The sample filtration unit may comprise an entrance channel, a biocompatible micro-filter, or an exit channel.

In some embodiments of the apparatus, the biocompatible micro-filter is capable of filtering the biological subject based on at least one property selected from physical size, hardness, elasticity, shear strength, weight, surface feature, optical, acoustical, thermal, chemical, mechanical, biological, bio-chemical, electrical, electro-chemical, magnetic, electromagnetic, electro-mechanical, electro-chemical-mechanical, and electro-chemical-biological property.

In some embodiments of the apparatus, the recharging unit recharges nutrient or respiring gas to the biological subject. The nutrient can include a biocompatible strong or weak electrolyte, amino acid, mineral, ions, oxygen, oxygen-rich liquid, intravenous drip, glucose, or protein; and the respiring gas can include oxygen.

In some embodiments, the biological subject to be tested comprises blood, urine, saliva, tear, saline, or sweat.

In still another aspect, the invention provides alternative apparatus for detecting a disease in a biological subject. The apparatus each comprise a launching chamber to launch a probe object at a desired speed and direction, a detection unit, a probe object, a detection component, a channel for transporting the biological subject to be tested and the probe object.

In some embodiments of these apparatus, the launching chamber comprises a piston for releasing the probe object and a channel for directing the probe object.

Yet still another set of apparatus for detecting a disease in a biological subject as provided by this invention are those fabricated by a method comprising: providing a substrate; sequentially depositing a first material and a second material as two layers onto the substrate to form a material stack; patterning the second material to form a first desired feature; depositing a third material onto the material stack to cover the second material; optionally patterning the first material and third material to form a second desired feature; and optionally depositing a fourth material onto the material stack; wherein the detection device is capable of interacting with the biological subject to generate a response signal.

In some embodiments, in these methods used for fabricating the apparatus, the second material can be patterned by microelectronic processes.

In some embodiments, in these methods used for fabricating the apparatus, the first material and third material can be the same or different.

In some embodiments, in these methods used for fabricating the apparatus, the first material and third material are patterned by lithography and etch processes selective to the second material to form at least one type of trench feature in the layers of the third material and first material.

In some embodiments, in these methods used for fabricating the apparatus, the fabrication method may further comprise capping the top of the material stack to form an enclosed trench. The enclosed trench can, e.g., be used to observe and record features and behaviors of the biological subject. The capping can comprise, e.g., placing a second device on the top of the material stack, and the second device can be a device identical to the detection device being capped, a piece of glass or crystal, or a functional device selected from the group consisting of an imaging device, an optical sensor, a memory storage, a signal transmission, a logic processing component, a circuit for data storage, signal transmission, and signal processing.

In some embodiments, in these methods used for fabricating the apparatus, the first feature or second feature is selected from the group consisting of partitioned chambers, chambers connected with channels, channels, probe generator (probe), detection probes, electrically connective interconnection lines, optical transmission lines, and piezo-electric lines. For example, the partitioned chambers can be for pre-processing of the biological subject for initial screening and enhancement of concentration of diseased biological subject for further testing, chambers connected with channels are for pre-processing and detection, channels can be for biological subject to flow through, the probe generator (probe) can be for generating probe and disturb signal onto the biological subject for triggering a response signal, the detection probe can be for measuring properties of the biological subject and the response signal, the electrically connective interconnection lines can be for transmitting signals, the optical transmission lines can be for transmitting signals, and piezo-electric lines can be for using piezo-electric effect to probe biological subjects.

In some embodiments, in these methods used for fabricating the apparatus, the second material is patterned using lithography and etch processes selective to the first material to form a desired component such as a detection probe.

In some embodiments, in these methods used for fabricating the apparatus, the first and third materials are patterned using lithography and etch processes selective to the second material to form at least one type of trench feature in the layers of the third and first materials, with the second material reasonably aligned with the wall of the trench.

In some embodiments, in these methods used for fabricating the apparatus, the thickness of the fourth material is thinner than that of the third material.

In some embodiments, the second and the fourth materials form detection probes.

In some embodiments, the second and the fourth materials form a probe and a detector, respectively.

In some embodiments, the apparatus may further include an imaging device for observing and recording properties and behaviors of the biological subject.

In some embodiments, the apparatus may further include a pre-processing unit with chambers for pre-screening and enhancing a diseased biological subject for further testing, channels for carrying fluidic sample to flow through, probes for probing and disturbing the biological subject being tested for generating response signals, detection probes for measuring properties and response signals of the biological subject, and an imaging device, a camera, a viewing station, an acoustic detector, a thermal detector, an ion emission detector, or a thermal recorder for observing and recording properties and behaviors of the biological subject.

In some embodiments, the apparatus may further include a memory storage, a signal transmission, a logic processing component, or a circuit for data storage, signal transmission, or signal processing. These additional devices can be fabricated by microelectronics processes on the substrate where the first material is deposited.

In some embodiments, the apparatus may have typical channel dimensions ranging from about 2 microns×2 microns to about 100 microns×100 microns in cross sectional area for a square-shaped channel, a radius ranging from about 1 micron to about 20 microns in cross sectional area for a circular shaped channel, and a typical probe dimension ranging from about 0.5 micron×0.5 micron to about 20 microns×20 microns in cross sectional area for a square-shaped probe.

In some embodiments, the apparatus may have typical channel dimensions ranging from about 6 microns×6 microns to about 14 microns×14 microns in cross sectional area for a square-shaped channel, a radius ranging from about 3 microns to about 8 microns in cross sectional area for a circular shaped channel, and a typical probe dimension ranging from about 0.5 micron×0.5 micron to about 10 microns×10 microns in cross sectional area for a square shaped probe.

In some embodiments, the first material and the fourth material each comprise un-doped oxide ($SiO_2$), silicon nitride, doped oxide, a polymer material, glass, or an insulating material.

In some embodiments, the second material and third material each comprise an electrically conductive material, aluminum, an aluminum alloy, copper, a copper alloy, tungsten, a tungsten alloy, gold, a gold alloy, silver, a silver alloy, or a piezo-electric material. Examples of the piezo-electric material include, but are not limited to, quartz, berlinite, gallium, orthophosphate, $GaPO_4$, tourmaline, ceramics, barium, titanate, $BatiO_3$, lead zirconate, titanate PZT, zinc oxide, aluminum nitride, and a polyvinylidene fluoride.

In yet some other embodiments, the second material and fourth material each comprise an electrically conductive material or a piezo-electric material. Examples of the electrically conductive material include, but are not limited to, aluminum, an aluminum alloy, copper, a copper alloy, tungsten, a tungsten alloy, gold, a gold alloy, silver, a silver alloy; whereas examples of the piezo-electric material include, but are not limited to, quartz, berlinite, gallium, orthophosphate, $GaPO_4$, tourmaline, ceramics, barium, titanate, $BatiO_3$, lead zirconate, titanate PZT, zinc oxide, aluminum nitride, and a polyvinylidene fluoride.

In some embodiments of the apparatus, the detection device comprises at least one probe, at least one detector, or at least one pair of probe and detector, the probe generates a probing or disturbing signal onto the biological subject to give a response signal, and the detector measures the response signal thus generated.

In some embodiments of the apparatus, the second material is patterned by microelectronic processes to form a first desired feature; the first material and third material are optionally patterned by microelectronic processes to form a second desired feature; and the first material and third material can be the same or different.

In some embodiments, the methods for fabricating the apparatus further include capping the top of the material stack to form an enclosed trench, with such trench used for test sample transportation or detection site.

One of the key novel aspects of this patent application is the design and fabrication process flows of micro-devices and methods of using the micro-devices for contacting and measuring properties, at microscopic levels and in a three dimensional space, of a biological subject (e.g., a single cell or a single biological molecule such as DNA or RNA). The micro-devices have micro-probes arranged in a three dimensional manner with feature sizes as small as a cell, a DNA, and a RNA and capable of trapping, sorting, probing, measuring, or modifying biological subjects.

Another aspect of this invention relates to methods for fabricating a micro-device. The methods include depositing various materials on a substrate and, in the interims of depositing every two materials, pattern the materials by microelectronic technology and associated processes, wherein the micro-device is capable of measuring at the microscopic level the electric, magnetic, electromagnetic, thermal, optical, acoustical, biological, chemical, physical, physical-chemical, bio-chemical, bio-physical, mechanical, bio-chemical mechanical, bio-electro-mechanical, bio-electro-chemical mechanical, electro-chemical mechanical, micro-electro-mechanical property of a biologic subject that the micro-device is to contact.

Still another aspect of this invention relates to methods for fabricating a micro-device, which include depositing a first material on the substrate, patterning the first material by a microelectronic process to give rise to at least one patterned residual and leaving part of the substrate surface uncovered by the first material, depositing a second non-conductive material atop the processed first material and the substrate, creating an opening in the second material and exposing part of the patterned residual of the first material, filling up the opening in the second material with a third material. In some embodiments, the microelectronic process comprises thin film deposition, photolithography, etching, cleaning, or chemical mechanical polishing.

Yet in still another aspect, the invention provides methods for fabricating a micro-device, which include the first step of depositing a first material onto a substrate; the second step of depositing a second material onto the first material and then patterning the second material with a microelectronic technology or process; and repeating the second step at least once with a material that can be the same as or different from the first or second material. The materials used in the repeated steps can be the same as or different from the first or second material. In some embodiments, at least one of the materials used in fabricating the micro-device is a piezo-electric material or a conductive material.

In some embodiments, multiple fabricated micro-devices can be coupled, joined, and connected by physical or electrical method to constitute the more advanced devices.

In some embodiments, the apparatuses of this invention can be integrated on a single device (e.g., by using a semiconductor processing technology) or assembled on a board (e.g., by using a computer packaging technology).

In some embodiments, patterning of a material is done by a microelectronic process (e.g., chemical vapor deposition, physical vapor deposition, or atomic layer deposition to deposit various materials on a substrate as an insulator or conductor; lithography or etch to transfer patterns from design to structure; chemical mechanical planarization, chemical cleaning for particle removal, thermal spiking anneal to reduce the crystal defects, diffusion or ion implantation for doping elements into specific layers). In some embodiments, patterning is planarization by chemical polishing, mechanical polishing, or chemical mechanical polishing.

In some other embodiments, the methods further include removal of a stack of multiple layers of materials by wet etch, plasma etch, or by vapor etch.

In some embodiments, the micro-device can move in any direction. For instance, two micro-devices can move in opposite directions.

In some embodiments, the micro-device thus fabricated is so patterned that it is capable of trapping, sorting, probing, measuring, or modifying a biological subject; or that it can pierce through the membrane of a cell.

Still another aspect of the invention relates to methods for fabricating a device or apparatus for detecting disease in a biological subject, which include providing a substrate, sequentially depositing a first material and a second material as two different layers onto the substrate to form a material stack, patterning the second material by microelectronic processes to form a first desired feature, depositing a third material onto the material stack, optionally patterning the first and third materials by microelectronic processes to form a second desired feature, and optionally depositing a fourth material onto the material stack.

In some embodiments, the methods further include steps of fabricating (utilizing processes including but not limited to depositing, patterning, polishing, and cleaning) additional components onto the substrate before sequentially depositing the first material and the second material as layers onto the substrate, wherein the additional components comprise a data storage component, a signal processing component, a memory storage component, a signal transmitting component, a logic processing component, or an RF (radio-frequency) component.

In some other embodiments, the methods further include steps of fabricating at least a circuit onto the substrate before sequentially depositing the first material and the second material as layers onto the substrate, wherein the circuit comprises a data storage circuit, a signal processing circuit, a memory storage circuit, a signal transmitting circuit, or a logic processing circuit.

In still some other embodiments, the methods of this invention further include a step of planarizing the third material using chemical mechanical polishing process or an etch back process, after the step of depositing the third material onto the material stack and before the step of patterning the first and the third materials.

Examples of the suitable microelectronic processes include, but are not limited to, thin film deposition, lithography, etch, polishing, cleaning, ion implantation, diffusion, and packaging as typically used in microelectronics.

The first and third materials can be the same or different. They can be, for example, electrically insulating material, such as oxide, doped oxide, silicon nitride, or a polymer.

The second material can be an electrically conductive material, a piezo-electric material, a semiconductor material, a thermal sensitive material, an optical material, a pressure sensitive material, an ion emission sensitive material, or any combination thereof. For example, the second material can be copper, aluminum, tungsten, gold, silver, glass, an aluminum alloy, a copper alloy, a tungsten alloy, a gold alloy, a silver alloy, quartz, berlinite, gallium, orthophosphate, $GaPO_4$, tourmaline, ceramics, barium, titanate, $BaTiO_3$, lead zirconate, titanate PZT, zinc oxide, aluminum nitride, and a polyvinylidene fluoride.

In some embodiments, the first desired feature can be a probe, whereas the second desired feature can be a recessed form, or a trench form in the layers of the first and third materials.

In yet some other embodiment, the methods of this invention further comprise depositing a fourth material onto the material stack and then patterning the fourth material to form a recessed area such as a hole at a selected location.

In still another embodiment, the methods of this invention further comprise a step of removing the third material from the material stack by wet or vapor etch to form a detection chamber between the fourth material and the substrate. Furthermore, they may also include a step of removing the first material from the material stack by wet or vapor etch to form a channel. The channel can connect the formed detection chamber with additional chambers.

In yet still another embodiment, the methods of this invention further include a step of sealing or capping the top of the material stack to form an enclosed trench. In one example of this step, the top of the material stack is sealed or capped with an additional device onto the material stack. Examples of such an additional device include, but are not limited to, an imaging device and a detecting probe. The above said device on top of the material stack comprises of optical device, imaging device, camera, viewing station, acoustic detector, thermal detector, ion emission detector, and thermal recorder.

In yet another aspect, the present invention provides methods for fabricating a device for detecting disease in a biological subject, which include providing a substrate, sequentially depositing a first and a second materials as layers onto the substrate to form a material stack, patterning the second material by lithography and etch process to form a recessed area in the layer of the second material, depositing a third material onto the material stack, removing a portion of the third material above the second material by etch back or polishing process, patterning the third material by lithography and etch to form at least a portion of recessed area in the layer of the third material, depositing a fourth material onto the material stack, and removing the portion of the fourth material above the third material by etch back or polishing process to keep at least a portion of the second and fourth material in the same layer.

The first and third materials used in the methods of this invention can be the same or different. In some embodiments, they are the same. They can be, e.g., an electrically insulating material. Examples of the first and third materials include, but are not limited to, oxide, doped oxide, silicon nitride, or a polymer.

In some embodiments, following the deposition and processing of the third or fourth material, at least one more material is deposited and processed to form a top layer with a detection chamber or channels formed underneath.

Examples of the second material include, but are not limited to, electrically conductive materials, piezo-electric materials, semiconductor materials, thermal sensitive materials, a pressure sensitive material, an ion emission sensitive material, optical materials, or any combinations thereof.

In some embodiments, a novel detection apparatus comprising a detection chamber and/or channels for test sample transport is formed by methods that include the steps of: depositing a first material, patterning the first material ("material A") to form at least a recessed area, depositing a second material ("material B"), removing the second material ("material B") from areas above the first material ("material A") by using polishing and/or etch back processes, leaving the second material ("material B") in the recessed area in the first material layer, depositing a third material ("material C") to cover the first material ("material A") and the second material ("material B"), patterning the third material ("material C") to form at least a hole smaller than the recessed area(s) in the third material layer and above it, removing the second material ("material B") optionally by using vapor etch or wet etch, forming an enclosed cavity in the first material layer.

In yet some other embodiments, a novel detection apparatus can be integrated with at least one micro-injector and at least one detector, in which the micro-injector can inject a desired object into the biological subject to be tested to generate a response by the biological subject and the detector detects the response thus generated by the biological subject.

The invention further provides methods for detecting a biological subject's dynamic response to a signal. These methods include providing an apparatus comprising two micro-devices of which one is a probing micro-device and the other is a detecting micro-device and positioned with a distance from the probing micro-device; contacting the biological subject with the probing micro-device whereby the probing micro-device measures a property of the biological subject at the microscopic level or sends a stimulating signal to the biological subject; and the detecting micro-device measures the response of the biological subject through measuring properties of the biological subject at the microscopic level. Optionally, the detecting micro-device contacts the biological subject during the measurements.

In some embodiments, the signal is an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical signal.

In some other embodiments, the property at the microscopic level is an electric, magnetic, electromagnetic, thermal, optical, acoustical, biological, chemical, electro-mechanical, electro-chemical, electro-chemical-mechanical, bio-chemical, bio-chemical-physical, bio-mechanical, bio-electro-mechanical, bio-electro-chemical, bio-electro-chemical-mechanical, physical, or mechanical property.

Examples of the electrical properties include, but are not limited to, surface charge, surface potential, resting potential, electrical current, electrical field distribution, electric dipole, electric quadruple, three-dimensional electrical and/or charge cloud distribution, electrical properties at telomere of DNA and chromosome (also called sticky end or DNA end) or impedance. Examples of the thermal properties include temperature, and vibrational frequency of biological item and molecules. Examples of the optical properties include optical absorption, optical transmission, optical reflection, optical-electrical properties, brightness, and fluorescent emission. Examples of the chemical properties include pH value, chemical reaction, bio-chemical reaction, bio-electro-chemical reaction, reaction speed, reaction energy, speed of reaction, oxygen concentration, oxygen consumption rate, ionic strength, catalytic behavior, and bonding strength. Examples of the physical properties include density and geometric size. Examples of the acoustic properties include frequency, speed of acoustic waves, acoustic frequency and intensity spectrum distribution, acoustic intensity, acoustical absorption, and acoustical resonance. Examples of the mechanical property include internal pressure, hardness, shear strength, elongation strength, fracture stress, adhesion, mechanical resonance frequency, elasticity, plasticity, and compressibility. The date from measuring one or more of the properties at the microscopic level can be used for detecting diseases, e.g., cancer at its early stage, or for estimating the life expectancy of the carrier of the biological subject.

In some other embodiments, the apparatus further includes a third micro-device that is different from the probing micro-device and the detecting micro-device; and the third micro-device measures the same or a different property of the biological subject as the probing micro-device and the detecting micro-device do.

In still some other embodiments, the apparatus further includes a clock micro-device that is different from the probing micro-device and the detecting micro-device; and the type of clock micro-device is placed at a fixed distance before the probing micro-devices and detecting micro-devices with a distinctive signal when a biological subject passes it and acts as a clock device.

Yet still in some embodiments, the data recorded by the detecting micro-device is filtered by a phase lock-in technology to remove noise unsynchronized to the clock signal in order to enhance signal to noise ratio and improve measurement sensitivity.

Another aspect of this invention relates to methods for detecting disease in a biological subject, comprising providing an apparatus comprising a channel, a detection probe, imaging device, a memory storage component, a signal transmitting component, or a logic processing component, pre-processing the biological subject to enhance its concentration, measuring the properties of the biological subject, optionally contacting the biological subject with the detection probe through the channel to give a response signal, using the detection probe to detect the response signal from the biological subject, optionally separating diseased biological subject from healthy biological subject based on the response signal, optionally sending the separated, suspected diseased biological subject on for further tests, and analyzing the response signal and reaching a diagnosis conclusion. The biological subject can be a DNA, a sub-structure in a cell, a cell, or a protein.

In some embodiments, the methods of this invention further include detection of the response signal and behaviors of interaction or events occurred between at least two biological subjects or at least one biological subject with at least one non-biological subject. The at least two biological subject can be different or identical, in type of composition. Examples of interactions or events occurred between at least two biological subjects include, but are not limited to, a DNA colliding with another DNA, a cell smashing into another cell, a DNA crashing into a cell, a protein colliding with another protein, or a DNA crashing into a protein. Examples of interactions or events occurred between at least one biological subject with at least one non-biological subject include, but not limited to, an inorganic particle colliding with a biological subject, an organic particle colliding with a biological subject, or a composite particle colliding with a biological subject.

Examples of the response signals include, but are not limited to, an electric, magnetic, electromagnetic, thermal, optical, acoustical, biological, chemical, electro-mechanical, electro-chemical, electro-chemical-mechanical, bio-chemical, bio-chemical-physical, bio-mechanical, bio-electro-mechanical, bio-electro-chemical, bio-electro-chemical-mechanical, physical, and mechanical signal.

Anther aspect of the current invention relates to methods for detecting disease in a biological subject. The methods include providing an apparatus comprising a pre-processing unit, at least one detection device, a partitioned chamber with channels connecting them, and an injection device (for, e.g., injecting a probe material into the biological subject to be tested), and measuring response signals from the biological subject, wherein the probe material comprises an organic particle, an inorganic particle, a biological subject, or a composite-based object.

Yet another aspect of the current invention relates to methods for detecting a disease in a biological subject by interacting it with a probe object, comprising providing an apparatus comprising a launching chamber, a detection unit, and channels, launching a probe object onto the biological subject, causing a collision between the probe object and the biological subject to give rise to a response signal, recording and detecting the response signal during and after the collision. The probe object may comprise an organic particle, an inorganic particle, a biological subject, or a composite-based object.

Still another aspect of this invention relates to methods for detecting a disease in early stage in a biological subject. These methods include the steps of collecting a first sample (including a cell or a biological molecule) of the biological subject's tissue or organ potentially carrying the disease, collecting a second sample of the same tissue or organ from a second subject free of the disease, separately contacting the first and second samples with a disease detection apparatus of this invention, and comparing the data from the measurements of the first and second samples. As mentioned above, a disease detection apparatus of this invention includes a micro-device and a substrate supporting the micro-device, wherein the micro-device is capable of measuring at the microscopic level the electric, magnetic, electromagnetic, thermal, optical, acoustical, biological, chemical, physical, or mechanical property of a biological sample.

Still a further aspect of this invention relates to a method of cellular communication. The micro-device can generate artificial microscopic calcium (or other elements) oscillations which simulate the intracellular biological communications. This artificial signal can be coded to interact with cellular proteins, nucleus, and eventually regulates cell's determination or fate.

Yet still a further aspect of this invention relates to methods for determining cellular or molecular response to a signal. The methods include the step of contacting a cell or biological molecule with a disease detection apparatus of this invention—which includes a first micro-device, a second micro-device, and a first substrate supporting the first micro-device and second micro-device. The first micro-device in the apparatus is capable of measuring at the microscopic level an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical property of the cell; and the second micro-device contacts the cell or biological molecule and stimulates it with a signal.

In some embodiments of these methods, the apparatus further comprises a third micro-device that is capable of measuring at the microscopic level the same electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical property of the cell or biological molecule as the first micro-device is.

In some other embodiments, the cell contacts the first micro-device, second micro-device, and third micro-device in the order.

In some further embodiments, the signal is an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical signal.

In some embodiments of the apparatus of this invention, the system for delivering the biological subject includes at least one channel inside which the biological subject to be detected travels in a certain direction; the probing and detecting device includes at least one probing micro-device and at least one detecting micro-device, at least one probing micro-device is located before at least one detecting microdevice relative to the direction in which the biological subject travels, and the probing micro-device and the detecting micro-device can be attached to the interior or exterior wall of the channel. In some other embodiments, multiple channels with different geometries are utilized.

In some examples of these embodiments, the probing and detecting device includes at least two detecting micro-devices capable of measuring at the micro-level the same or different properties of the biological subject. Examples of the electrical properties include, but are not limited to, surface charge, surface potential, resting potential, electrical current, electrical field distribution, electric dipole, electric quadruple, three-dimensional electrical and/or charge cloud distribution, electrical properties at telomere of DNA and chromosome or impedance; examples of the thermal properties include temperature, and vibrational frequency of biological item and molecules; examples of the optical properties include optical absorption, optical transmission, optical reflection, optical-electrical properties, brightness, and fluorescent emission; examples of the chemical properties include pH value, chemical reaction, bio-chemical reaction, bio-electro-chemical reaction, reaction speed, reaction energy, speed of reaction, oxygen concentration, oxygen consumption rate, ionic strength, catalytic behavior, and bonding strength; examples of the physical properties include density and geometric size; examples of the acoustic properties include frequency, speed of acoustic waves, acoustic frequency and intensity spectrum distribution, acoustic intensity, acoustical absorption, and acoustical resonance; and examples of the mechanical property include internal pressure, hardness, shear strength, elongation strength, fracture stress, adhesion, mechanical resonance frequency, elasticity, plasticity, and compressibility. For instance, the detecting micro-devices are capable of measuring at the microscopic level the surface charge, electric potential, brightness, fluorescent emission, geometric size, shape, frequency, internal pressure, or temperature of the biological subject.

In some other embodiments, the shapes and sizes of different sections of the channel can be the same or different; the width of the channel can be about 1 nm~1 mm (e.g., 1~750 nm, 1~600 nm; 100~800 nm, 200~750 nm, or 400~650 nm); the channel can be straight, curved, or angled; the interior wall of the channel defines a circular, oval, or polygon (e.g., rectangular) space.

An example of a suitable channel is a circular carbon nano-tube, which can have a diameter of, e.g., about 0.5~100 nm, or a length of, e.g., about 5.0 nm~10 mm.

In some embodiments, the interior wall of the channel has at least one concave that may be in the same section as a probing or detecting micro-device. The concave groove can be, e.g., a cubic space or an angled space. It can have a depth of, e.g., about 10 nm~1 mm.

In some other embodiments, a distribution fluid can be injected into the channel, either before or after the biological subject passes a probing micro-device, to aid the traveling or separation of the biological subject inside the channel. A suitable distribution fluid is a biocompatible liquid or solution, e.g., water or saline. The distribution fluid can be injected into the channel through a distribution fluid channel connected to an opening in the channel wall. Utilizing such a distribution fluid allows, among others, preparation of the surface of the channel (in which the biological subject travels), cleaning of the channel, disinfection of the apparatus, and enhancing the measurement sensitivity of the apparatus.

In still some other embodiments, the apparatus of this invention can be for detecting the diseases of more than one biological subject, and the channel comprises a device located therein for separating or dividing the biological subjects based on different levels of a same property of the biological subjects. An example of such a separating or dividing device is a slit that can, e.g., separate or divide biological subjects based on their surface charges, their density, their size, or other properties such as electrical, thermal, optical, chemical, physical, magnetic, electromagnetic, and mechanical properties. Examples of the electrical properties include, but are not limited to, surface charge, surface potential, resting potential, electrical current, electrical field distribution, electric dipole, electric quadruple, three-dimensional electrical and/or charge cloud distribution, electrical properties at telomere of DNA and chromosome or impedance; examples of the thermal properties include temperature, and vibrational frequency of biological item and molecules; examples of the optical properties include optical absorption, optical transmission, optical reflection, optical-electrical properties, brightness, and fluorescent emission; examples of the chemical properties include pH value, chemical reaction, bio-chemical reaction, bio-electro-chemical reaction, reaction speed, reaction energy, speed of reaction, oxygen concentration, oxygen consumption rate, ionic strength, catalytic behavior, and bonding strength; examples of the physical properties include density and geometric size; examples of the acoustic properties include frequency, speed of acoustic waves, acoustic frequency and intensity spectrum distribution, acoustic intensity, acoustical absorption, and acoustical resonance; and examples of the mechanical property include internal pressure, hardness, shear strength, elongation strength, fracture stress, adhesion, mechanical resonance frequency, elasticity, plasticity, and compressibility.

In yet still some other embodiments, the apparatus of this invention can further include a filtering device for removing irrelevant objects from the biologic subject for detection.

In another aspect, the invention provides methods for obtaining dynamic information of a biologic material, each comprising contacting the biological subject (e.g., including but not limited to a cell, substructure of a cell such as cell membrane, a DNA, a RNA, a protein, or a virus) with an apparatus comprising a first micro-device, a second micro-device, and a first substrate supporting the first micro-device and second micro-device, wherein the first micro-device is capable of measuring at the microscopic level an electric, magnetic, electromagnetic, thermal, optical, acoustical, biological, chemical, physical, or mechanical property of the biological subject, and the second micro-device contacts the biological subjects and stimulates it with a signal.

In yet another embodiment, the micro-device in the detection apparatus can communicate with biological subjects such as cells, DNA, RNA, virus, or protein. Further, the micro-device can trap, sort, analyze, treat, and modify biological subjects such as cells, DNA, RNA, blood cells, protein, or virus. Specifically, an array of micro-devices arranged in a desired manner can trap, sort, detect, and modify DNA structures.

In some embodiments, the apparatus further comprising a third micro-device that is capable of measuring at the microscopic level the same electric, magnetic, electromagnetic, thermal, optical, acoustical, biological, chemical, biochemical, physical, or mechanical property of the cell as the first micro-device is. In some other embodiments, the cell contacts the first micro-device, second micro-device, and third micro-device in the order. In still some other embodiments, the signal is an electric signal, a magnetic signal, an electromagnetic signal, a thermal signal, an optical signal, an acoustical signal, a biological signal, a chemical signal, a physical signal, or a mechanical electric signal.

In another aspect, this invention provides alternative methods for detecting a biological subject's dynamic information. The methods each include providing an apparatus comprising a clock micro-device, a probing micro-device, and a first detection micro-device, with the probing micro-device being placed between the clock micro-device and the detection micro-device; contacting the biological subject with the clock micro-device whereby the clock micro-device registers the arrival of the biological subject, and optionally measures a property of the biological subject at the microscopic level; contacting the biological subject with the probe device with a periodic probe signal delivered onto the biological subject; using the detecting micro-device to detect response signal from the biological subject; and processing the detected signal by the detection micro-device using phase lock-in technology to filter out signal components un-synchronized to the frequency of the probe signal, and amplify the signal synchronized to the probe signal.

In some embodiments of these methods, there is a distance of at least 10 angstroms between the clock micro-device and the first detecting micro-device.

In some other embodiments, the response signal is an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical signal.

In some other embodiments, the first probing micro-device optionally measures the same property of the biological subject at the microscopic level as the first detecting micro-device does.

In still some other embodiments, the apparatus used in the methods further comprises a second probing micro-device capable of sending a stimulating signal to the biological subject that is different from the signal sent by the first probing micro-device.

In still some other embodiments, the apparatus used in the methods further comprise a second detecting micro-device capable of measuring the same property of the biological subject at the microscopic level as the first detecting micro-device does.

In yet still some other embodiments, the electrical property is surface charge, surface potential, resting potential, electrical current, electrical field distribution, electric dipole, electric quadruple, three-dimensional electrical or charge cloud distribution, electrical properties at telomere of DNA and chromosome, or impedance; the thermal property is temperature, or vibrational frequency of biological item or molecules; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, oxygen concentration, oxygen consumption rate, ionic strength, catalytic behavior, or bonding strength; the physical property is density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

In some embodiments, the data recorded by the first detecting micro-device is filtered by a phase lock-in technology to remove noise unsynchronized to the data recorded by the first probing micro-device or the clock micro-device. The filtered data may have a higher signal to noise data ratio.

Another innovative aspect of the present invention is the use of micro-devices for obtaining real time data and information at the cellular structure level, such as using a micro voltage comparator, four-point probe and other circuitry designs to measure cell surface or bulk electrical properties including resting potential and surface charge for differentiating normal cells and cancer cells. The cell surface charge differentiation can be an important factor in deciding the healthy or unhealthy status of a cell and, accordingly, the proper treatment thereof.

For example, in a time of flight approach to obtain dynamic information on a biological subject (e.g., a cell, a substructure of a cell, a DNA or RNA molecule, or a virus), a first micro-device is first used to send a signal to perturb the biological subject to be diagnosed, and then a second micro-device is employed to accurately measure the response from the biological subject. In one arrangement, the first micro-device and the second device are positioned at a desired distance L apart, with a biological subject to be measured flowing from the first micro-device towards the second micro-device. When the biological subject sample passes the first micro-device, the micro-device sends a signal to the passing biological sample, and then the second micro-device detects the response or retention of the perturbation signal on the entity. From the distance between the two micro-devices, time interval, the nature of perturbation by the first micro-device, and measured changes on the biological subject during the time of flight, microscopic and dynamic properties of the biological subject can be measured and data obtained. In another arrangement, a first micro-device is used to probe the biological subject by first applying a signal (such as a charge) and then detecting the response from the biological subject with a second micro-device as a function of time.

Another novel area of this application is the invention of micro-indentation probes and micro-probes for measuring a range of physical properties (such as mechanical properties) of biological subjects. Examples of such physical properties include but not limited to hardness, shear strength, elongation strength, fracture stress, and properties related to cell membranes as the membranes may be a critical component in disease diagnosis.

Still yet another aspect of this invention is the design, fabrication, and integration of the various components in the disease detection apparatus. These components include, e.g., a sample containment and delivery unit; an array of sample delivery channels; a central disease detection unit comprising multiple detection probes, a central control unit comprising a logic processing unit, a memory unit, a sensor, a signal transmitter, a signal receiver, and an application specific chip; and a waste sample treatment unit in which used sample can be treated, recycled, processed for reuse, or disposed.

Another key novel aspect of the current application is the design, integration, and fabrication process flow of micro-devices capable of making highly sensitive and advanced measurements on very weak signals in biological systems for disease detection under complicated environment with very weak signal and relatively high noise background.

Those novel capabilities using the class of micro-devices disclosed in this invention for disease detection include, e.g., making dynamic measurements, real time measurements (such as time of flight measurements, and combination of using probe signal and detecting response signal), phase lock-in technique to reduce background noise, and 4-point probe techniques to measure very weak signals, and unique and novel probes to measure various electronic, electromagnetic and magnetic properties of biological samples at the single cell, biological subject (e.g., virus) or molecule (e.g., DNA or RNA) level.

Finally, another aspect of this invention relates to apparatus for detecting disease in a biological subject. The apparatus includes a detection device fabricated by a method comprising: providing a substrate; sequentially depositing a first material and a second material as two layers onto the substrate to form a material stack; patterning the second material by microelectronic processes to form a first desired feature; depositing a third material onto the material stack to cover the second material; optionally patterning the first and third materials by microelectronic processes to form a second desired feature; and optionally depositing a fourth material onto the material stack. The first material and third material can be the same or different. The detection device is capable of probing the biological subject to be detected and giving rise to a response signal.

In some embodiments, the fabrication method further comprises capping the top of the material stack to form an enclosed trench.

In some other embodiments, the capping comprises sealing or capping the top of the material stack with an imaging device onto the material stack.

In still some other embodiments, the apparatus further includes a pre-processing unit (chambers) for pre-screening and enhancing a diseased biological subject for further testing, channels for carrying fluidic sample to flow through, probes for probing and disturbing the biological subject being tested for generating response signals, detection probes for measuring properties and response signals of the biological subject, or an imaging device for observing and recording properties and behaviors of the biological subject.

In yet some other embodiments, the detection device has typical channel dimensions ranging from about 2 microns×2 microns to about 100 microns×100 microns in cross sectional area for a square-shaped channel, a radius ranging from about 1 micron to about 20 microns in cross sectional area for a circular shaped channel, and a typical probe dimension ranging from about 0.5 micron×0.5 micron to about 20 microns×20 microns in cross sectional area for a square-shaped probe. Alternatively, the detection device has typical channel dimensions ranging from about 6 microns×6 microns to about 14 microns×14 microns in cross sectional area for a square-shaped channel, a radius ranging from about 3 microns to about 8 microns in cross sectional area for a circular shaped channel, and a typical probe dimension ranging from about 0.5 micron×0.5 micron to about 10 microns×10 microns in cross sectional area for a square shaped probe.

In yet still some embodiments, the first and the fourth materials each comprise un-doped oxide ($SiO_2$), doped oxide, silicon nitride, a polymer material, glass, or an electrically insulating material; the second and third materials each comprise an electrically conductive material, aluminum, an aluminum alloy, copper, a copper alloy, tungsten, a tungsten alloy, gold, a gold alloy, silver, a silver alloy, an optical material, an thermal sensitive material, a magnetic material, a pressure sensitive material, a mechanical stress sensitive material, an ion emission sensitive material, and a piezo-electric material.

In yet still some other embodiments, where the second and fourth materials can be fabricated at the same level as detectors, or as probes and detectors, the first and the third materials each comprise un-doped oxide ($SiO_2$), doped oxide, silicon nitride, a polymer material, glass, or an electrically insulating material; the second and fourth materials each comprise an electrically conductive material (e.g., aluminum, an aluminum alloy, copper, a copper alloy, tungsten, a tungsten alloy, gold, a gold alloy, silver, or a silver alloy), an optical material (e.g., anisotropic optical material, glass, glass-ceramic, laser gain media, nonlinear optical material, phosphor and scintillator, transparent material), an thermal sensitive material, a magnetic material, a pressure sensitive material, a mechanical stress sensitive material, an ion emission sensitive material, and a piezo-electric material (e.g., quartz, berlinite, gallium, orthophosphate, $GaPO_4$, tourmaline, ceramics, barium, titanate, $BatiO_3$, lead zirconate, titanate PZT, zinc oxide, aluminum nitride, and a polyvinylidene fluoride).

In further embodiments, the detection device comprises at least one probe, at least one detector, at least one pair of probe and detector in which the probe generates a probing or disturbing signal onto the biological subject to give a response signal and the detector measures the response signal thus generated.

As used herein, the term "or" is meant to include both "and" and "or". It may be interchanged with "and/or."

As used herein, a singular noun is meant to include its plural meaning. For instance, a micro device can mean either a single micro device or multiple micro-devices.

As used herein, the term "patterning" means shaping a material into a certain physical form or pattern, including a plane (in which case "patterning" would also mean "planarization.")

As used herein, the term "a biological subject" or "a biological sample" for analysis or test or diagnosis refers to the subject to be analyzed by a disease detection apparatus. It can be a single cell, a single biological molecular (e.g., DNA, RNA, or protein), a single biological subject (e.g., a single cell or virus), any other sufficiently small unit or fundamental biological composition, or a sample of a subject's organ or tissue that may having a disease or disorder.

As used herein, the term "disease" is interchangeable with the term "disorder" and generally refers to any abnormal microscopic property or condition (e.g., a physical condition) of a biological subject (e.g., a mammal or biological species).

As used herein, the term "subject" generally refers to a mammal, e.g., a human person.

As used herein, the term "microscopic level" refers to the subject being analyzed by the disease detection apparatus of this invention is of a microscopic nature and can be a single cell, a single biological molecular (e.g., DNA, RNA, or protein), a single biological subject (e.g., a single cell or virus), and other sufficiently small unit or fundamental biological composition.

As used herein, a "micro-device" or "micro device" can be any of a wide range of materials, properties, shapes, and degree of complexity and integration. The term has a general meaning for an application from a single material to a very complex device comprising multiple materials with multiple sub units and multiple functions. The complexity contemplated in the present invention ranges from a very small, single particle with a set of desired properties to a fairly complicated, integrated unit with various functional units contained therein. For example, a simple micro-device could be a single spherical article of manufacture of a diameter as small as 100 angstroms with a desired hardness, a desired surface charge, or a desired organic chemistry absorbed on its surface. A more complex micro device could be a 1 millimeter device with a sensor, a simple calculator, a memory unit, a logic unit, and a cutter all integrated onto it. In the former case, the particle can be formed via a fumed or colloidal precipitation process, while the device with various components integrated onto it can be fabricated using various integrated circuit manufacturing processes.

A micro device used in the present invention can range in size (e.g., diameter) from on the order of about 1 angstrom to on the order of about 5 millimeters. For instance, a micro-device ranging in size from on the order of about 10 angstroms to on the order of 100 microns can be used in this invention for targeting biological molecules, entities or compositions of small sizes such as cell structures, DNA, and bacteria. Or, a micro-device ranging in size from on the order of about one micron to the order of about 5 millimeters can be used in the present invention for targeting relatively large biological matters such as a portion of a human organ. As an example, a simple micro device defined in the present application can be a single particle of a diameter less than 100 angstroms, with desired surface properties (e.g., with surface charge or a chemical coating) for preferential absorption or adsorption into a targeted type of cell.

The present invention further provides an apparatus for detecting a disease in a biological subject, which comprises a pre-processing unit, a probing and detecting unit, a signal processing unit, and a disposal processing unit.

In some embodiments of the apparatus, the pre-processing unit includes a sample filtration unit, a recharging unit, a constant pressure delivery unit, and a sample pre-probing disturbing unit. This increases the contraction ratio of certain substance of interests (such as cancer cells) and therefore makes the apparatus more effective and efficient in detecting the targeted biological subject (such as cancer cells).

In some embodiments, the filtration unit can filter off unwanted substance by physical filtration (e.g., based on the electronic charge or size of the substance) or separation by chemical reaction (thereby completely removing the undesirable substances), biochemical reaction, electro-mechanical reaction, electro-chemical reaction, or biological reaction.

In some embodiments, the sample filtration unit can include an entrance channel, a disturbing fluid channel, an accelerating chamber, and a slit. The slit and the interior walls of the entrance channel define two channels (e.g., a top channel and a bottom channel) wherein the biological subject can be separated due to the differences in its property (e.g., electric or physical property).

In some embodiments, a bio-compatible fluid can be injected into the disturbing fluid channel to separate the biological subject. For example, the bio-compatible fluid can be injected from the entrance of the disturbing fluid channel and deliver to an opening in the entrance channel wall. The bio-compatible fluid can be liquid or semi-liquid, and can include saline, water, plasma, an oxygen-rich liquid, or any combination thereof.

In some other embodiments, the angle between the entrance channel and the disturbing fluid channel ranges from about 0° to about 180° (e.g., from about 30° to about 150°, from about 60° to about 120°, or from about 75° to about 105°, or about 90°).

In some other embodiments, the width of each channel can range from about 1 nm to about 1 mm (e.g., from about 2 nm to about 0.6 mm or from about 10 nm to about 0.2 mm).

In some other embodiments, at least one of the channels comprises one probing device attached to the channel's sidewall, and the probing device is capable of measuring at the microscopic level an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property of the biological subject. Examples of the electrical property include surface charge, surface potential, resting potential, electrical current, electrical field distribution, electric dipole, electric quadruple, three-dimensional electrical or charge cloud distribution, electrical properties at telomere of DNA and chromosome, and impedance. Examples of the thermal property include temperature and vibrational frequency. Examples of the optical property include optical absorption, optical transmission, optical reflection, optical-electrical property, brightness, and fluorescent emission. Examples of the chemical property include pH value, chemical reaction, bio-chemical reaction, bio-electro-chemical reaction, reaction speed, reaction energy, speed of reaction, oxygen concentration, oxygen consumption rate, ionic strength, catalytic behavior, and bonding strength. Examples of the physical property include density and geometric size. Examples of the acoustic property include frequency, speed of acoustic waves, acoustic frequency and intensity spectrum distribution, acoustic intensity, acoustical absorption, and acoustical resonance. Examples of the mechanical property include internal pressure, hardness, shear strength, elongation strength, fracture stress, adhesion, mechanical resonance frequency, elasticity, plasticity, and compressibility.

In some embodiments, at least one of the channels comprises at least two probing devices attached to the channel's sidewalls, and the probing devices are capable of measuring at the microscopic level an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property of the biological subject. The probing devices measure the same or different properties at the same time or different times.

The two or more probing devices can be placed with a desired distance between each other (at least 10 angstroms). Examples of the desired distance include from about 10 nm to about 100 mm, from about 100 nm to about 10 mm, from about 1 mm to about 10 mm.

In some embodiments, the sample filtration unit can include an entrance channel, a biocompatible filter, an exit channel, or any combination thereof. When a biological subject passes through the entrance channel toward the exit channel, the biological subject of a size larger than the filter hole will be blocked against the exit channel, resulting in the smaller biological subject being flushed out through the exit channel. A biocompatible fluid is injected from the exit to carry the biological subject accumulated around the filter and flush out from the channel. The biological subject with a large size is then filtered for further analysis and detection in the detecting component or unit of the apparatus.

In some embodiments, the sample pre-probing disturbing unit can include one micro-device with a channel, a slit located inside the channel, and optionally two plates outside the channel. The two plates can apply a signal, e.g., an electronic voltage, to the biological subject traveling through the channel and separates it based on the electronic charge the biological subject carries. The slit and the interior channels of the channel define two channels where the separated biological subjects enter and optionally are detected for its property at the microscopic level.

In some embodiments, the sample pre-probing disturbing unit applies to the biological subject an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical signal. The signal can be applied, e.g., with the two plates described above or in other means (depending on the nature of the signal). The signal as applied can be pulsed or constant.

In some embodiments, the recharging unit recharges nutrient or respiring gas (such as oxygen) to the biological subject. Alternatively, it can also clean up the metabolite of the biological subject. With such a recharging unit, the life stability of the biological subject in the sample is sustained and its use is extended, thereby giving more accurate and reliable detecting results. Examples of nutrient include biocompatible strong or weak electrolyte, amino acid, mineral, ions, oxygen, oxygen-rich liquid, intravenous drip, glucose, and protein. Another example of the nutrient is a solution containing nano-particles that can be selectively absorbed by certain biological subjects (e.g., cells or viruses).

The recharging system can be separate from and outside of the other components of the apparatus. Alternatively, it can also be installed within one of the other components, e.g., the probing and detecting unit or the disposal processing unit.

In some other embodiments, the signal processing unit comprises an amplifier (e.g., a lock-in amplifier), an A/D (alternate/direct electric current or analog to digital) converter, a micro-computer, a manipulator, a display, and network connections.

In some instance, the signal processing unit collects more than one signal (i.e., multiple signals), and the multiple signals can be integrated to cancel out noise or to enhance the signal to noise ratio. The multiple signals can be signals from multiple locations or from multiple times.

Biological subjects that can be detected by the apparatus include, e.g., blood, urine, saliva, tear, and sweat. The detection results can indicate the possible occurrence or presence of a disease (e.g., one in its early stage) in the biological subject.

As used herein, the term "absorption" typically means a physical bonding between the surface and the material attached to it (absorbed onto it, in this case). On the other hand, the word "adsorption" generally means a stronger, chemical bonding between the two. These properties are very important for the present invention as they can be effectively used for targeted attachment by desired micro devices for measurement at the microscopic level.

As used herein, the term "contact" (as in "the first micro-device contacts a biologic entity") is meant to include both "direct" (or physical) contact and "non-direct" (or indirect or non-physical) contact. When two subjects are in "direct" contact, there is generally no measurable space or distance between the contact points of these two subjects; whereas when they are in "indirect" contact, there is a measurable space or distance between the contact points of these two subjects.

As used herein, the term "probe" or "probing," in addition to its dictionary meaning, could mean applying a signal (e.g., an electrical, acoustic, magnetic or thermal signal) to a subject and thereby stimulating the subject and causing it to have some kind of intrinsic response.

As used herein, the term "electric property" refers to surface charge, surface potential, electrical field, charge distribution, electrical field distribution, resting potential, action potential, or impedance of a biological subject to be analyzed.

As used herein, the term "magnetic property" refers to diamagnetic, paramagnetic, or ferromagnetic.

As used herein, the term "electromagnetic property" refers to property that has both electric and magnetic dimensions.

As used herein, the term "thermal property" refers to temperature, freezing point, melting point, evaporation temperature, glass transition temperature, or thermal conductivity.

As used herein, the term "optical property" refers to reflection, optical absorption, optical scattering, wave length dependent properties, color, luster, brilliance, scintillation, or dispersion.

As used herein, the term "acoustical property" refers to the characteristics found within a structure that determine the quality of sound in its relevance to hearing. It can generally be measured by the acoustic absorption coefficient. See, e.g., U.S. Pat. No. 3,915,016, for means and methods for determining an acoustical property of a material; T. J. Cox et al., *Acoustic Absorbers and Diffusers*, 2004, Spon Press.

As used herein, the term "biological property" is meant to generally include chemical and physical properties of a biological subject.

As used herein, the term "chemical property" refers to pH value, ionic strength, or bonding strength within the biological sample.

As used herein, the term "physical property" refers to any measurable property the value of which describes a physical system's state at any given moment in time. The physical properties of a biological sample may include, but are not limited to absorption, albedo, area, brittleness, boiling point, capacitance, color, concentration, density, dielectric, electric charge, electrical conductivity, electrical impedance, electric field, electric potential, emission, flow rate, fluidity, frequency, inductance, intrinsic impedance, intensity, irradiance, luminance, luster, malleability, magnetic field, magnetic flux, mass, melting point, momentum, permeability, permittivity, pressure, radiance, solubility, specific heat, strength, temperature, tension, thermal conductivity, velocity, viscosity, volume, and wave impedance.

As used herein, the term "mechanical property" refers to strength, hardness, toughness, elasticity, plasticity, brittleness, ductility, shear strength, elongation strength, fracture stress, or adhesion of the biological sample.

As used herein, the term "conductive material" (or its equivalent "electric conductor") is a material which contains movable electric charges. A conductive material can be a metal (e.g., copper, silver, or gold) or non-metallic (e.g., graphite, solutions of salts, plasmas, or conductive polymers). In metallic conductors, such as copper or aluminum, the movable charged particles are electrons (see electrical conduction). Positive charges may also be mobile in the form of atoms in a lattice that are missing electrons (known as holes), or in the form of ions, such as in the electrolyte of a battery.

As used herein, the term "electrically insulating material" (also known as "insulator" or "dielectric") refers to a material that resists the flow of electric current. An insulating material has atoms with tightly bonded valence electrons. Examples of electrically insulating materials include glass or organic polymers (e.g., rubber, plastics, or Teflon).

As used herein, the term "semiconductor" (also known as "semiconducting material") refers to a material with electrical conductivity due to electron flow (as opposed to ionic conductivity) intermediate in magnitude between that of a conductor and an insulator. Examples of inorganic semiconductors include silicon, silicon-based materials, and germanium. Examples of organic semiconductors include such aromatic hydrocarbons as the polycyclic aromatic compounds pentacene, anthracene, and rubrene; and polymeric organic semiconductors such as poly(3-hexylthiophene), poly(p-phenylene vinylene), polyacetylene and its derivatives. Semiconducting materials can be crystalline solids (e.g., silicon), amorphous (e.g., hydrogenated amorphous silicon and mixtures of arsenic, selenium and tellurium in a variety of proportions), or even liquid.

As used herein, the term "biological material" has the same meaning of "biomaterial" as understood by a person skilled in the art. Without limiting its meaning, biological materials or biomaterials can generally be produced either in nature or synthesized in the laboratory using a variety of chemical approaches utilizing organic compounds (e.g., small organic molecules or polymers) or inorganic compounds (e.g., metallic components or ceramics). They generally can be used or adapted for a medical application, and thus comprise whole or part of a living structure or biomedical device which performs, augments, or replaces a natural function. Such functions may be benign, like being used for a heart valve, or may be bioactive with a more interactive functionality such as hydroxyl-apatite coated hip implants. Biomaterials can also be used every day in dental applications, surgery, and drug delivery. For instance, a construct with impregnated pharmaceutical products can be placed into the body, which permits the prolonged release of a drug over an extended period of time. A biomaterial may also be an autograft, allograft, or xenograft which can be used as a transplant material. All these materials that have found applications in other medical or biomedical fields can also be used in the present invention.

As used herein, the term "microelectronic technology or process" generally encompasses the technologies or processes used for fabricating micro-electronic and optical-electronic components. Examples include lithography, etching (e.g., wet etching, dry etching, or vapor etching), oxidation, diffusion, implantation, annealing, film deposition, cleaning, direct-writing, polishing, planarization (e.g., by chemical mechanical polishing), epitaxial growth, metallization, process integration, simulation, or any combinations thereof. Additional descriptions on microelectronic technologies or processes can be found in, e.g., Jaeger, Introduction to Microelectronic Fabrication, $2^{nd}$ Ed., Prentice Hall, 2002; Ralph E. Williams, Modern GaAs Processing Methods, $2^{nd}$ Ed., Artech House, 1990; Robert F. Pierret, Advanced Semiconductor Fundamentals, $2^{nd}$ Ed., Prentice Hall, 2002; S. Campbell, The Science and Engineering of Microelectronic Fabrication, $2^{nd}$ Ed., Oxford University Press, 2001, the contents of all of which are incorporated herein by reference in their entireties.

As used herein, the term "selective" as included in, e.g., "patterning material B using a microelectronics process selective to material A", means that the microelectronics process is effective on material B but not on material A, or is substantially more effective on material B than on material B (e.g., resulting in a much higher removal rate on material B than on material A and thus removing much more material B than material A).

As used herein, the term "carbon nano-tube" generally refers to as allotropes of carbon with a cylindrical nano-structure. See, e.g., Carbon Nanotube Science, by P. J. F. Harris, Cambridge University Press, 2009, for more details about carbon nano-tubes.

Through the use of a single micro-device or a combination of micro-devices integrated into a disease detection apparatus, the disease detection capabilities can be significantly improved in terms of sensitivity, specificity, speed, cost, apparatus size, functionality, and ease of use, along with reduced invasiveness and side-effects. A large number of micro-device types capable of measuring a wide range of microscopic properties of biological sample for disease detection can be integrated and fabricated into a single detection apparatus using microfabrication technologies and novel process flows disclosed herein. While for the purposes of demonstration and illustration, a few novel, detailed examples have been shown herein on how microelectronics or nano-fabrication techniques and associated process flows can be utilized to fabricate highly sensitive, multi-functional, and miniaturized detection devices, the principle and general approaches of employing microelectronics and nano-fabrication technologies in the design and fabrication of high performance detection devices have been contemplated and taught, which can and should be expanded to various combination of fabrication processes including but not limited to thin film deposition, patterning (lithography and etch), planarization (including chemical mechanical polishing), ion implantation, diffusion, cleaning, various materials, and various process sequences and flows and combinations thereof.

BRIEF DESCRIPTIONS OF THE FIGURES

FIG. 1($a$) is a perspective illustration of a disease detection apparatus of this invention in which a biological sample placed in it or moving through it can be tested. FIG. 1($b$) and FIG. 1($c$) illustrate the apparatus which comprises multiple individual detection micro-devices.

FIG. 2($a$) is a perspective, cross-sectional illustration of a disease detection apparatus of this invention with multiple micro-devices. A biological sample is placed in the apparatus or moving through it while one or more microscopic properties of this biological sample are measured with the multiple micro-devices. FIGS. 2($b$)-2($l$) are perspective illustration of the novel process flow for fabricating the micro-device. FIGS. 2($m$)-2($n$) are cross-sectional views of an apparatus comprising multiple individual micro-devices.

Figure 13:
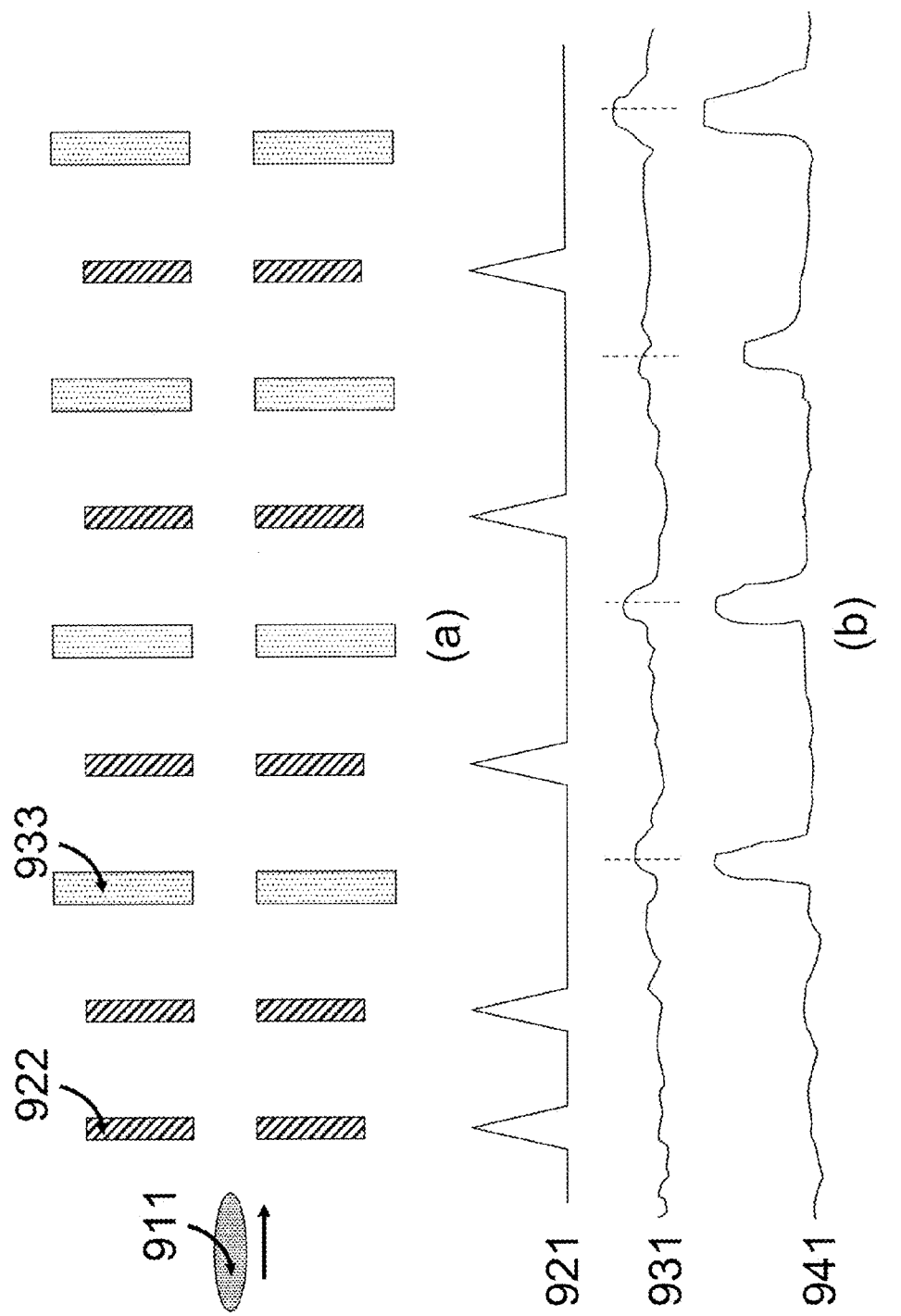

FIG. 13 illustrates a novel time of flight detection arrangement for disease detection applications, in which both clock signal generator and signal detection probes are used, along with schematically recorded clock signal, probe signal (signal detected by probing micro-device), and processed and enhanced signal after signal filtering using phase lock-in processing technique to enhance the detected signal.

Figure 14:
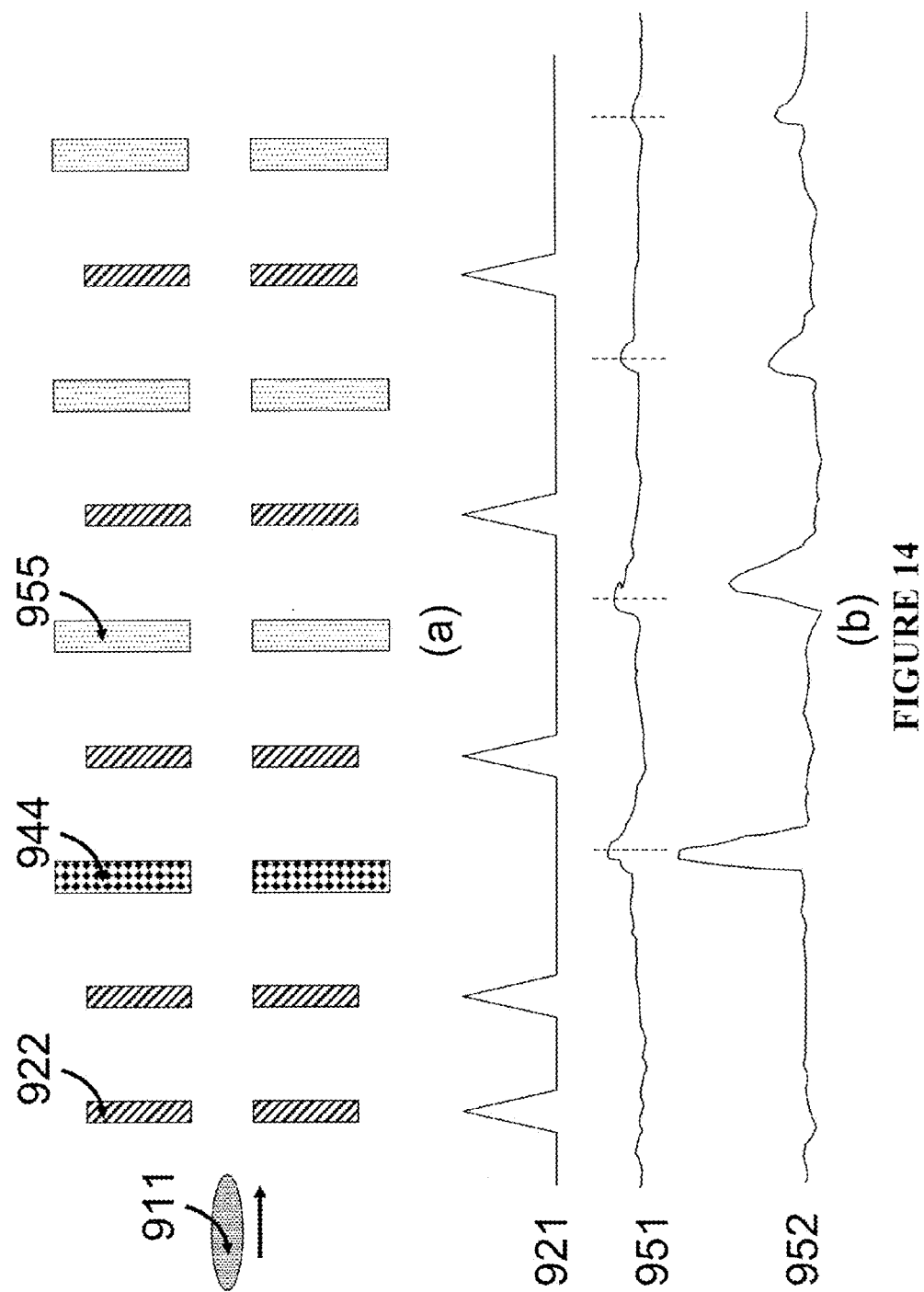

FIG. 14 illustrates yet another time of flight disease detection arrangement in which clock signal generators, a probe signal generator, and signal detection probes are used, along with schematically recorded clock signal, detected signal by probing micro-device in response to probe signal, and processed and enhanced signal after signal filtering using phase lock-in processing technique to enhance the detected signal showing detected response signal as a function of time (response signal delays over time in this case).

Figure 15:
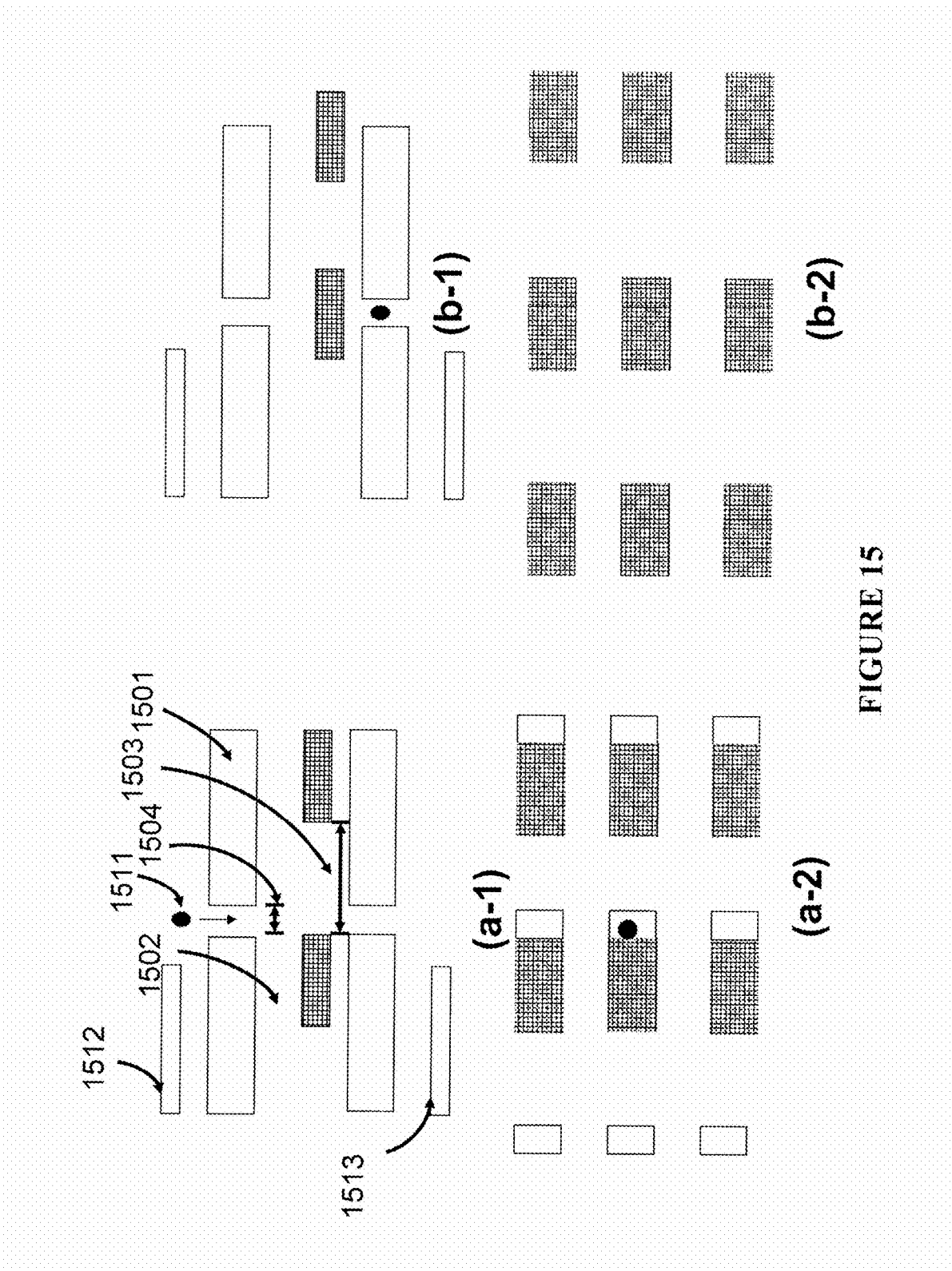
Figure 15:
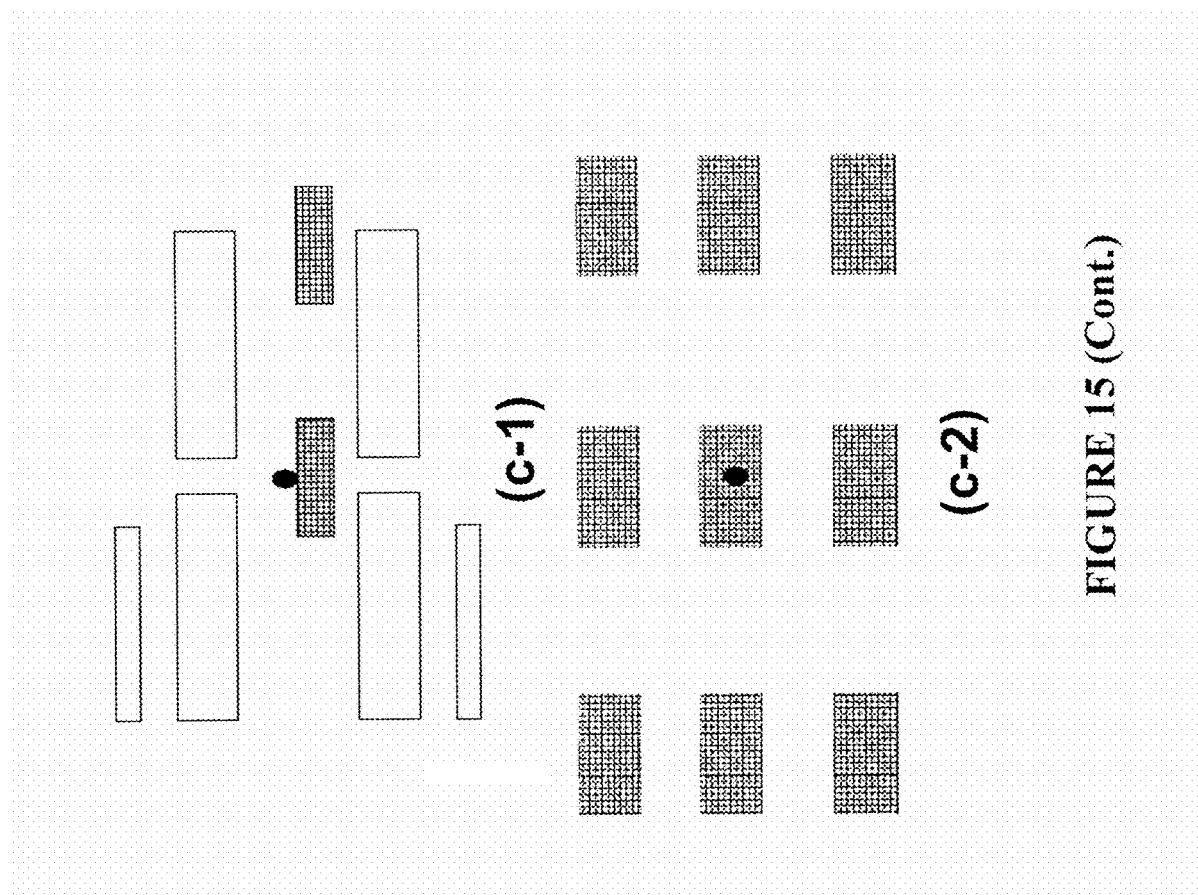

FIG. 15 illustrates another novel time of flight disease detection application, in which a set of novel micro-filters are utilized to detect biological subjects via separation of biological subjects by their various, specific properties such as size, weight, shape, electrical properties, or surface properties.

Figure 16:
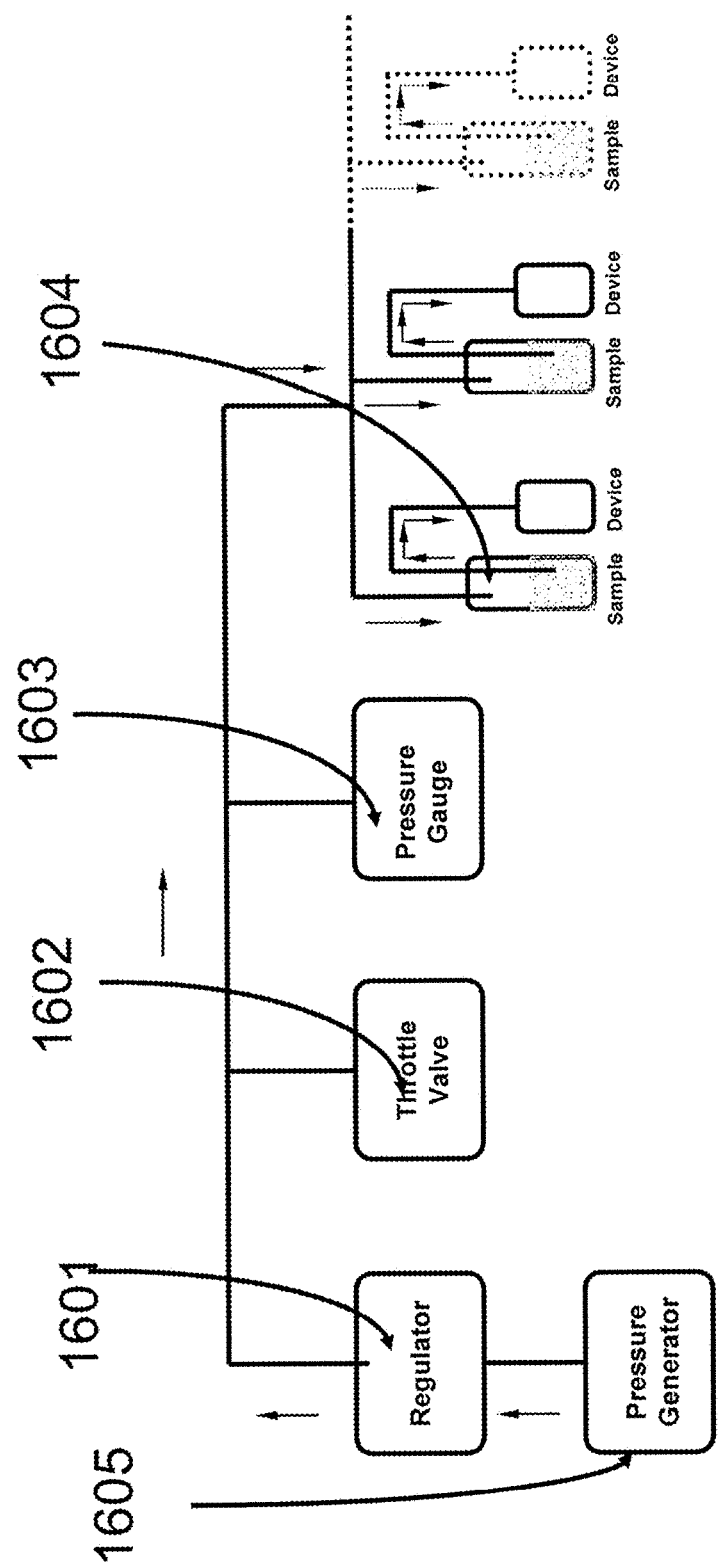

FIG. 16 illustrates a fluid delivery system, which is a pretreatment part for the disease detection apparatus, and it delivers a sample or auxiliary material at a desired pressure and speed into a device.

FIGS. 17(b)-17(c) illustrate a novel device which can engage in cellular communications at the single cell level by simulating cellular signals and receiving the cell's responses which can be a signal of electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical property. FIG. 17(a) illustrates how the signal is processed and responded in a single cell.

Figure 18:
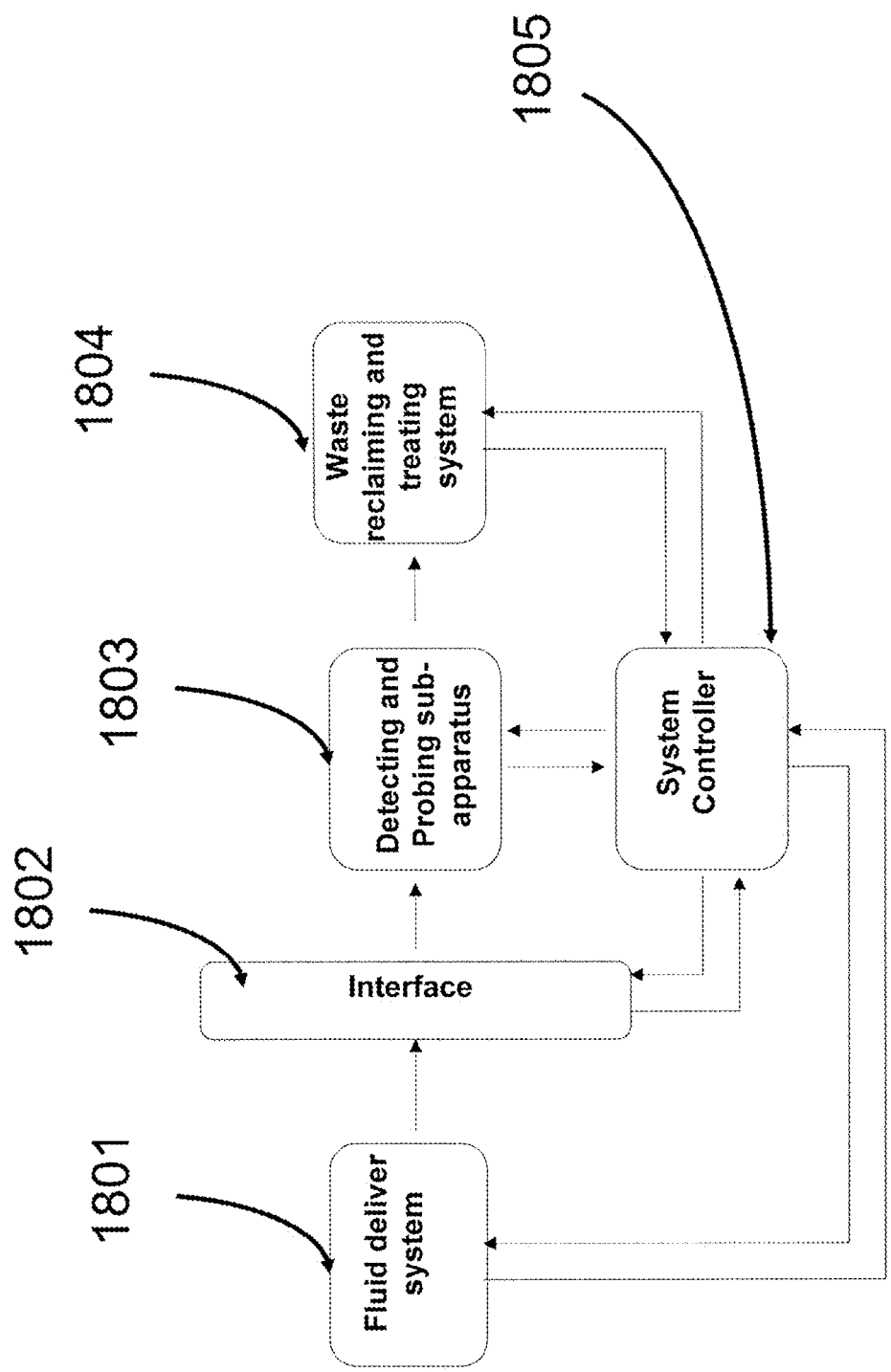

FIG. 18 illustrates a system block diagram of a disease detection apparatus, comprising various functional modules.

Figure 19:
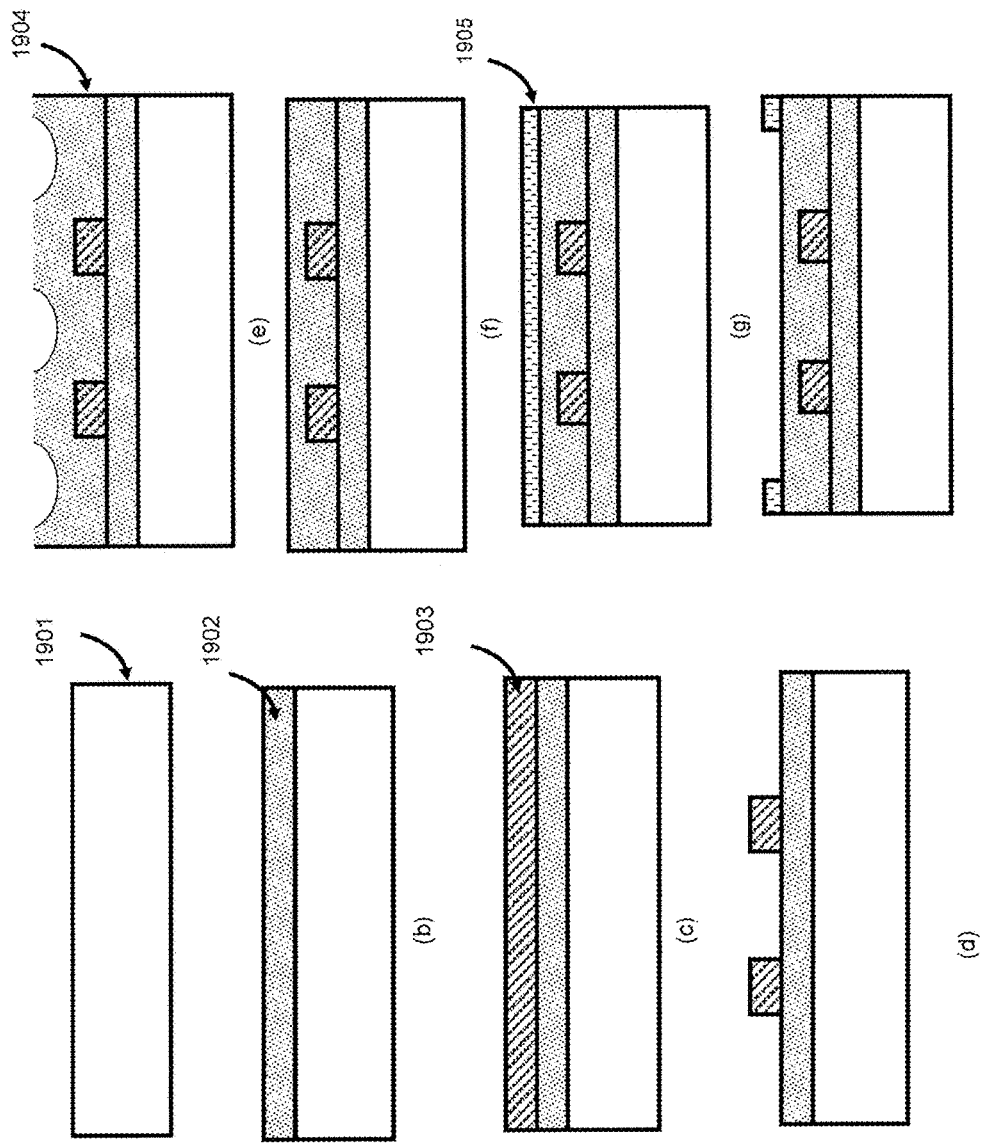
Figure 19:
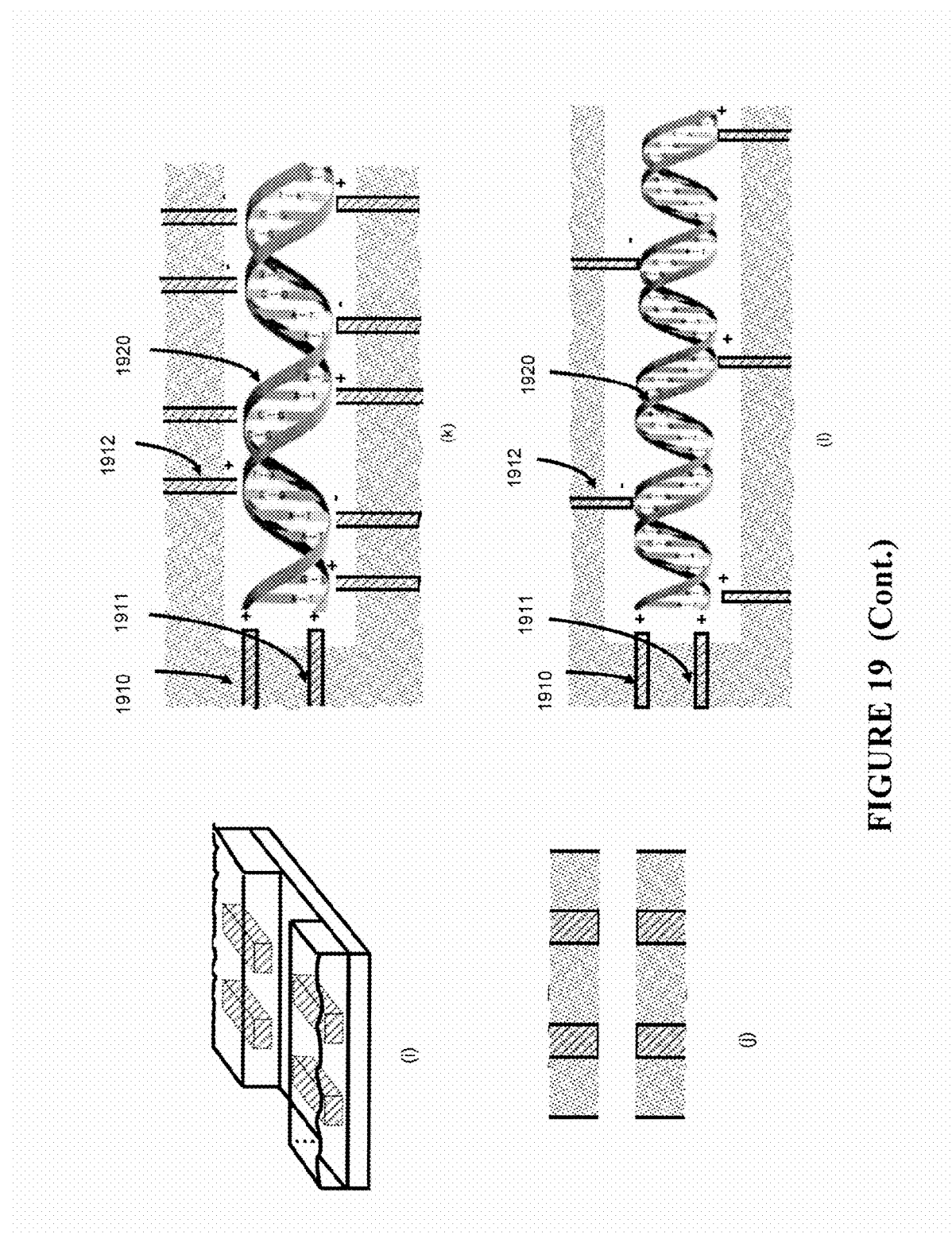

FIG. 19 illustrates a micro-device capable of communicating, trapping, sorting, analyzing, treating, or modifying a DNA and measuring the DNA's various properties (e.g., electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical properties).

Figure 20:
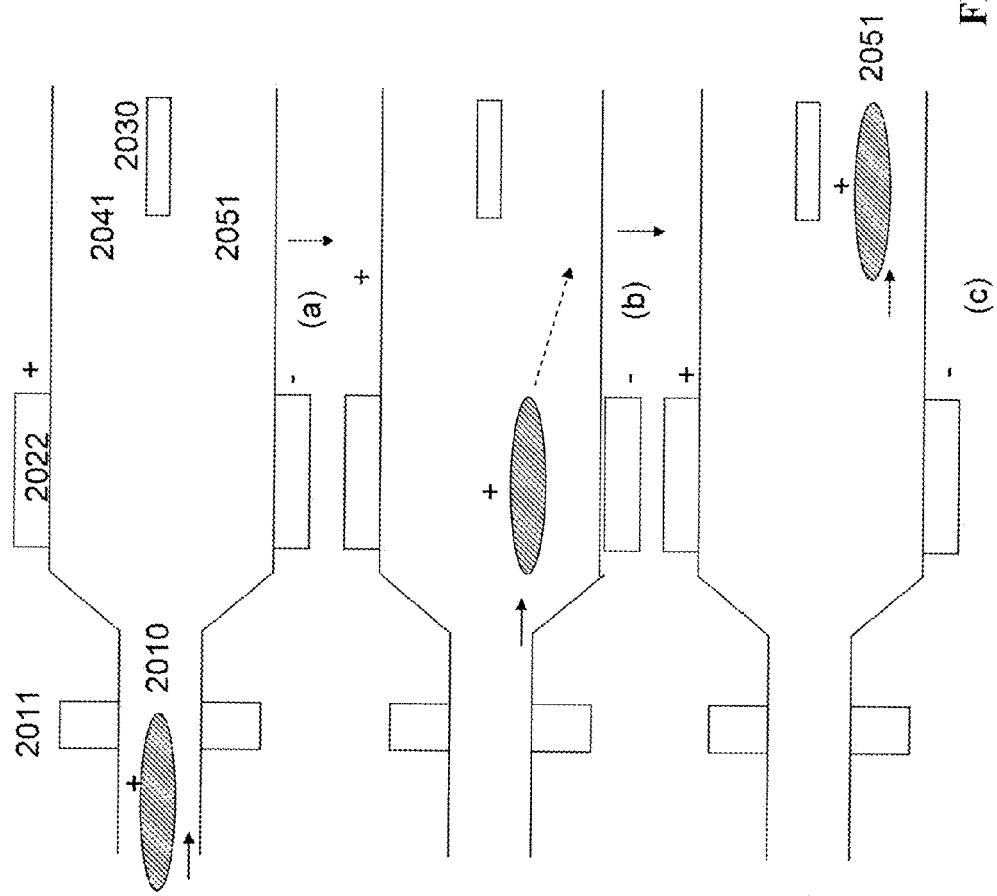

FIG. 20 illustrates an apparatus of this invention that can detect the surface charge on biological subjects and separate them by a slit based on the charge.

Figure 21:
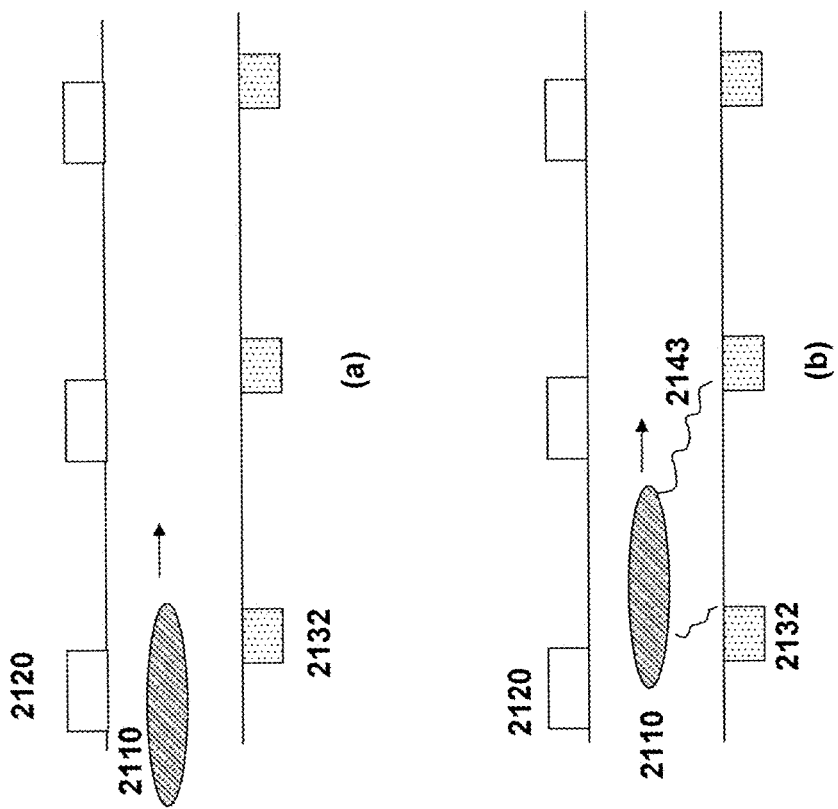

FIG. 21 illustrates another apparatus of this invention that can detect the optical properties of the biological subject with a set of optical sensors.

Figure 22:
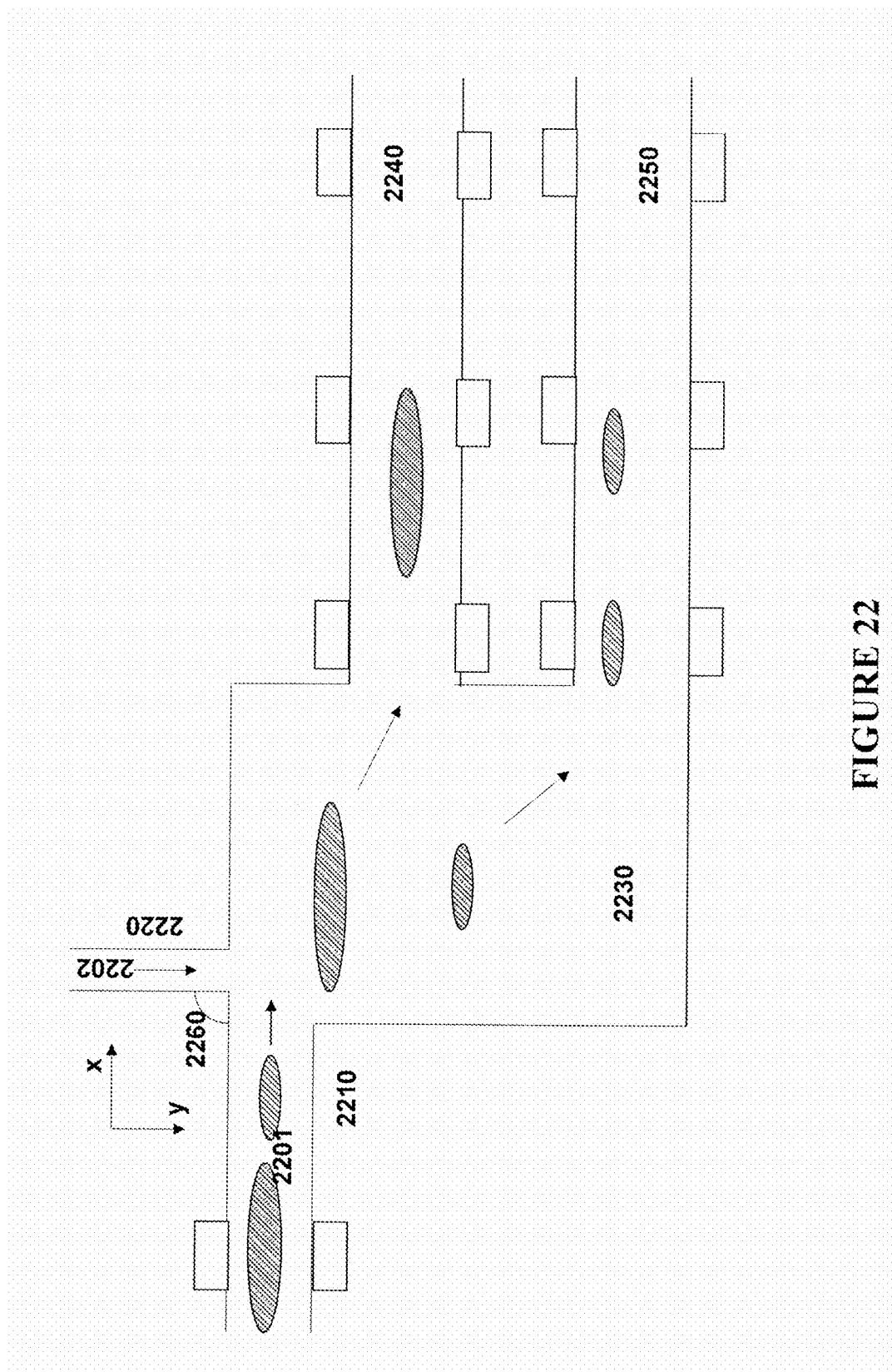

FIG. 22 illustrates another apparatus of this invention that can separate biological subjects of different geometric size and detect their properties respectively.

Figure 23:
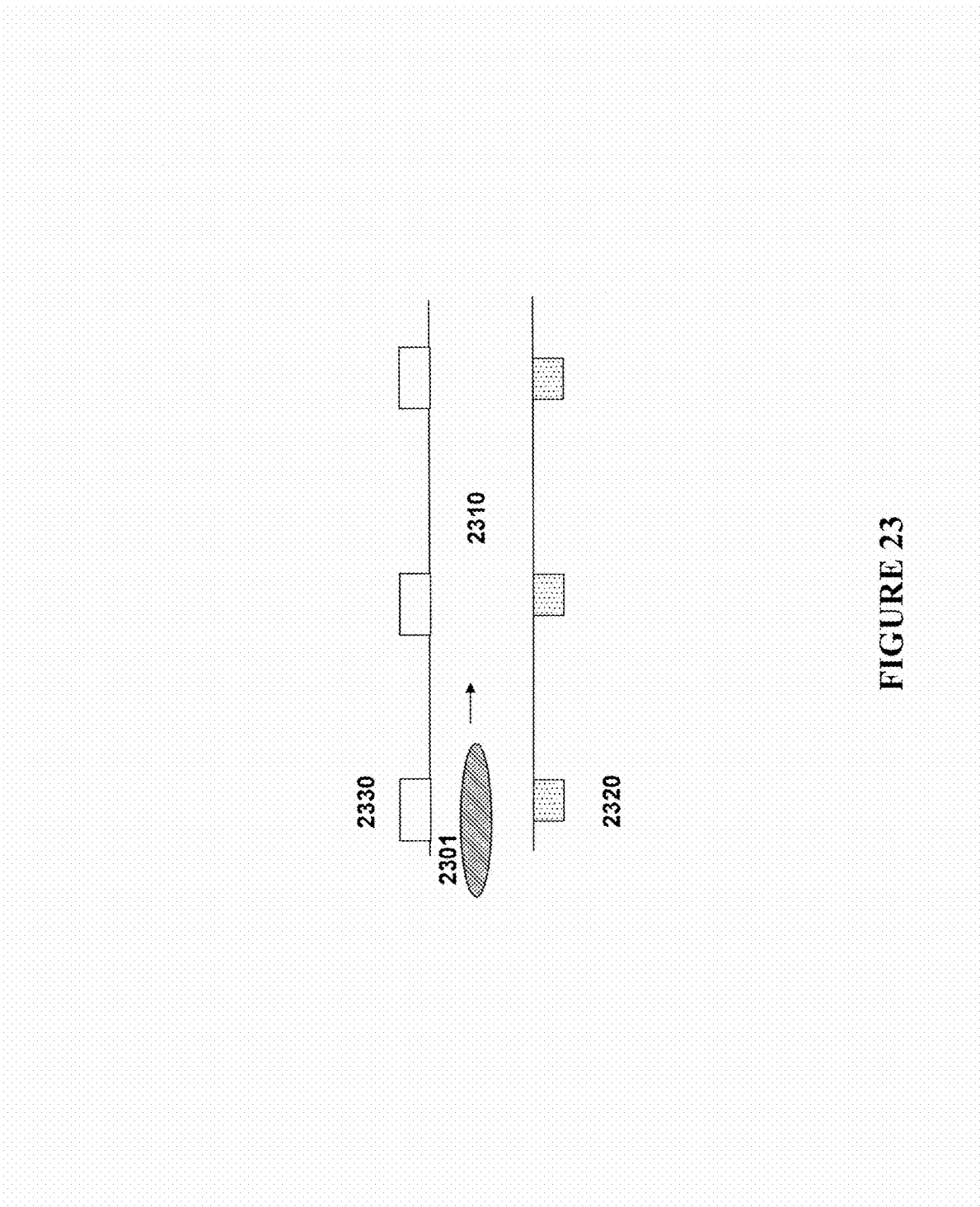

FIG. 23 illustrates an apparatus of this invention that can measure the acoustic property of a biological subject.

Figure 24:
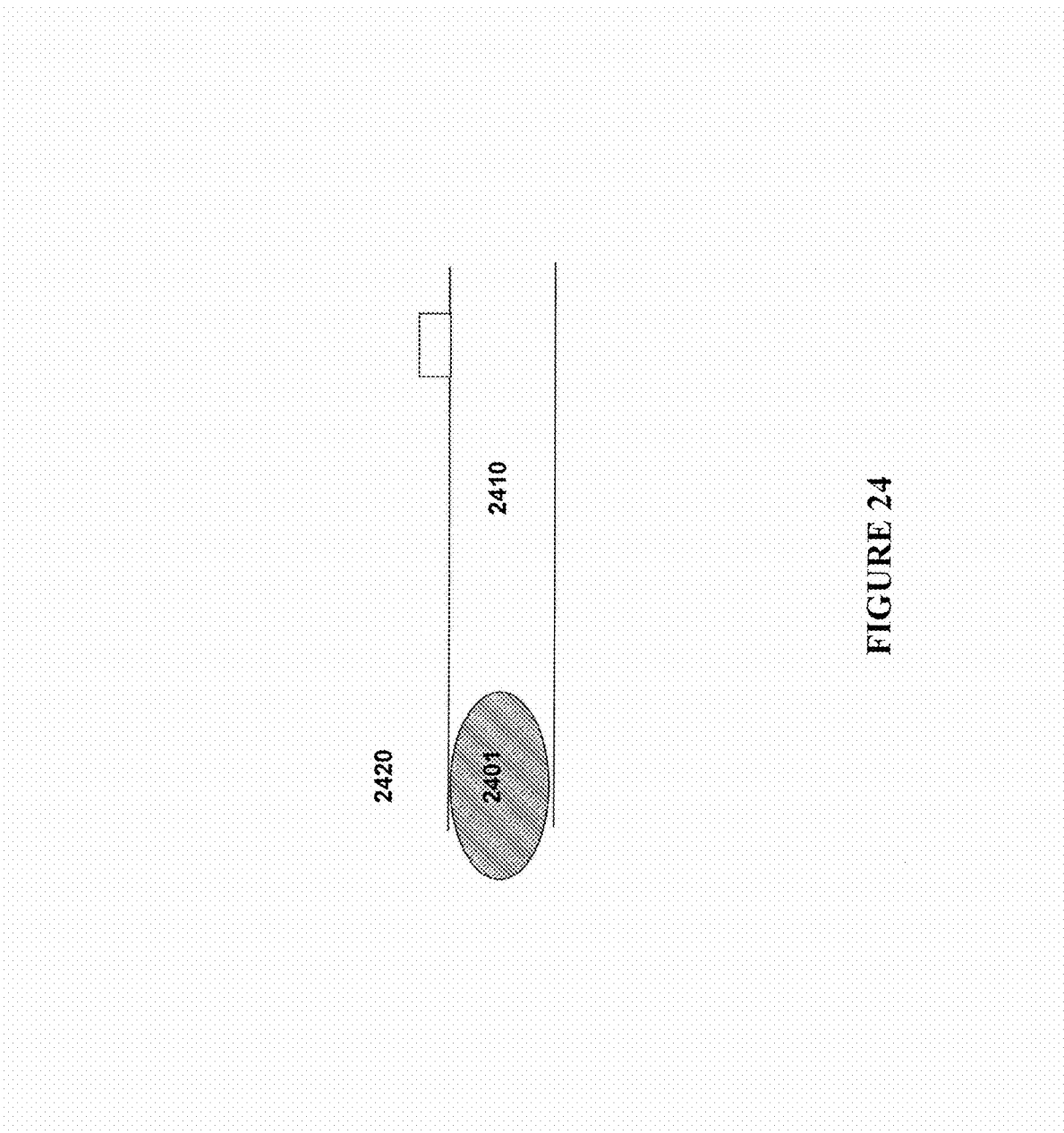

FIG. 24 illustrates an apparatus of this invention that can measure the internal pressure of a biological subject.

Figure 25:
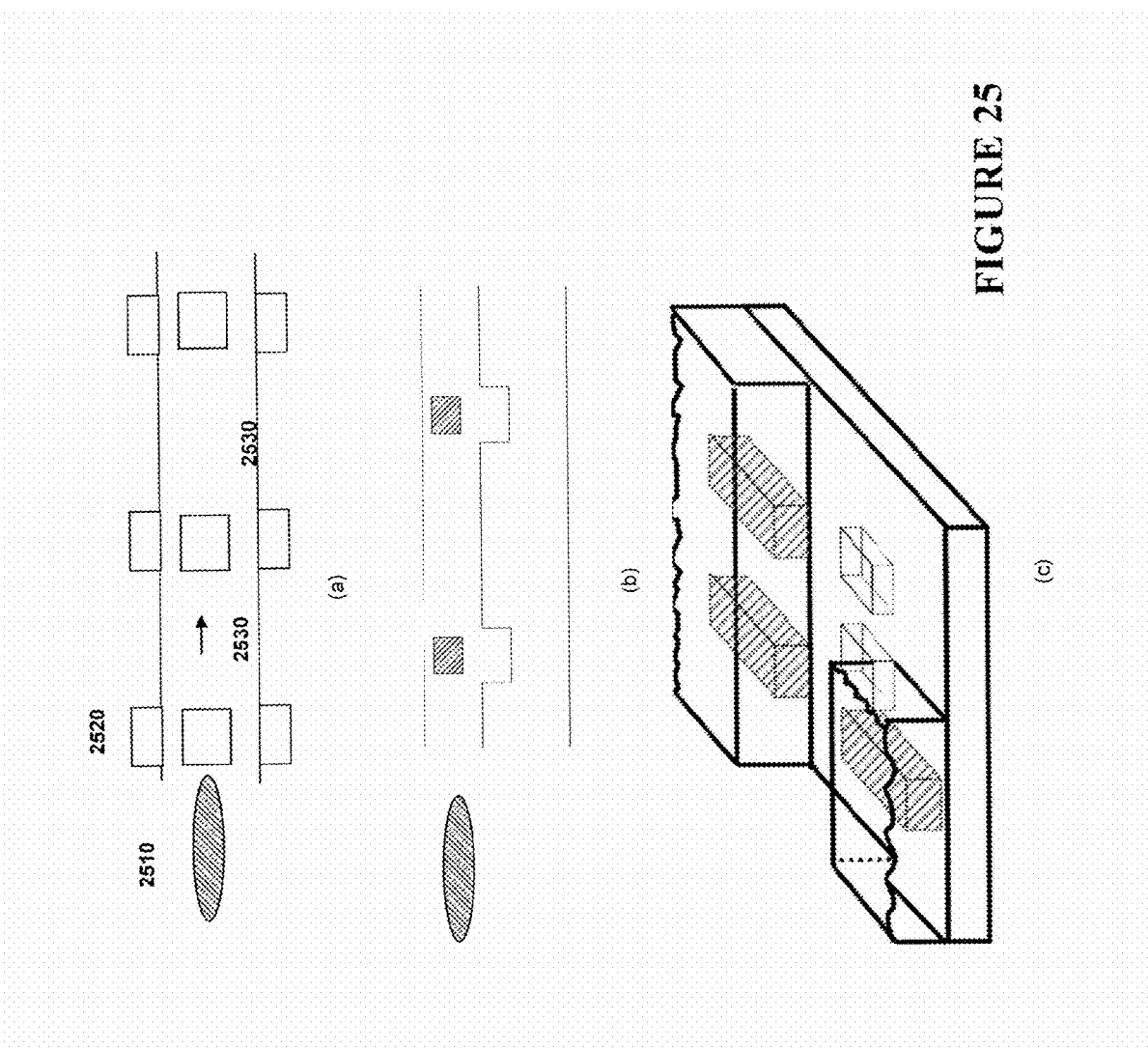

FIG. 25 illustrates an apparatus of this invention that has concaves between the probe couples, in the bottom or ceiling of the channel.

Figure 26:
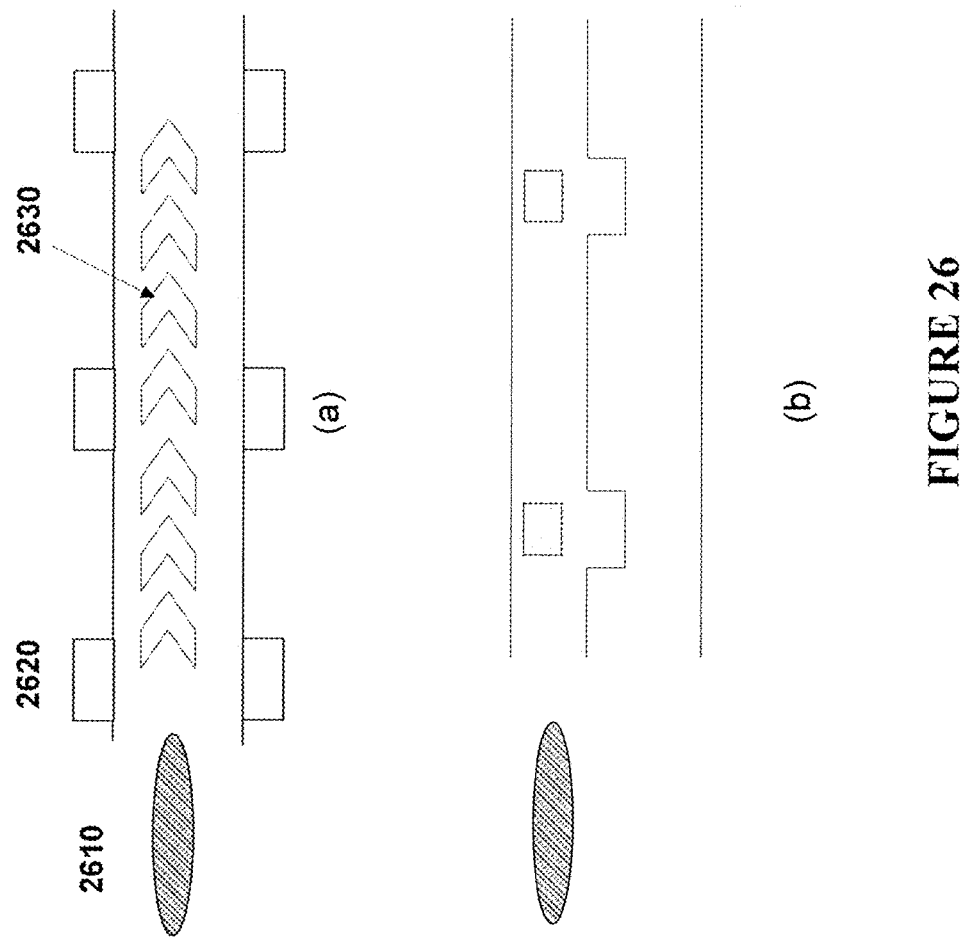

FIG. 26 illustrates another apparatus of this invention that has concaves of a different shape from those illustrated in FIG. 25.

Figure 27:
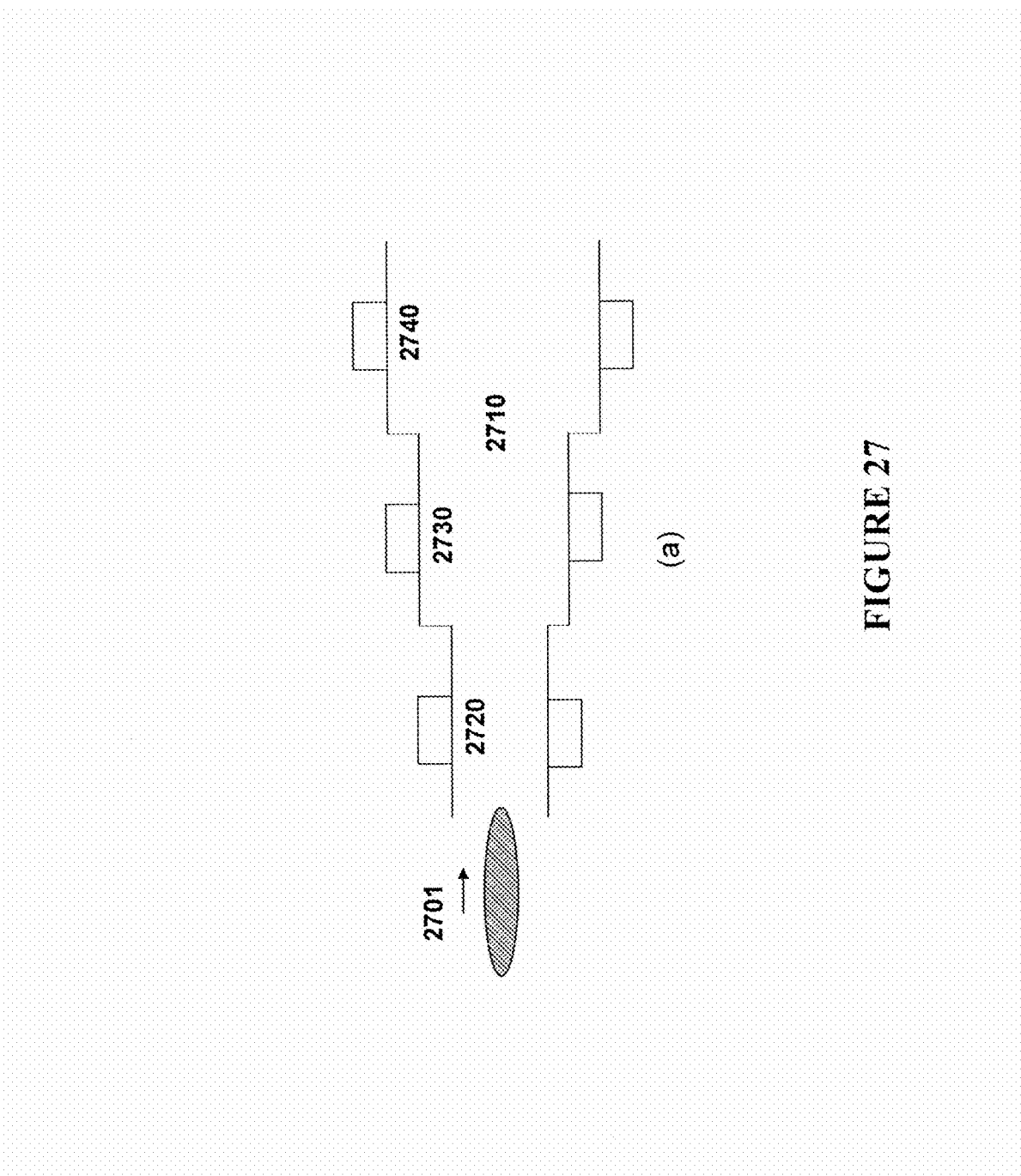

FIG. 27 illustrates an apparatus of this invention that has a stepped channel.

Figure 28:
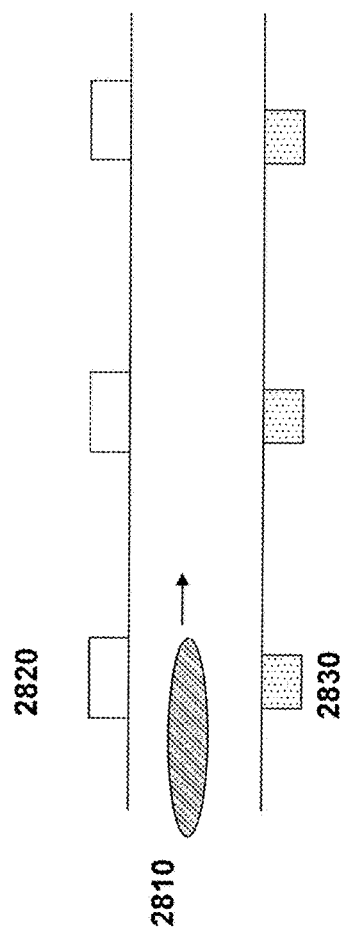

FIG. 28 illustrates an apparatus of this invention that has a set of thermal meters.

Figure 29:
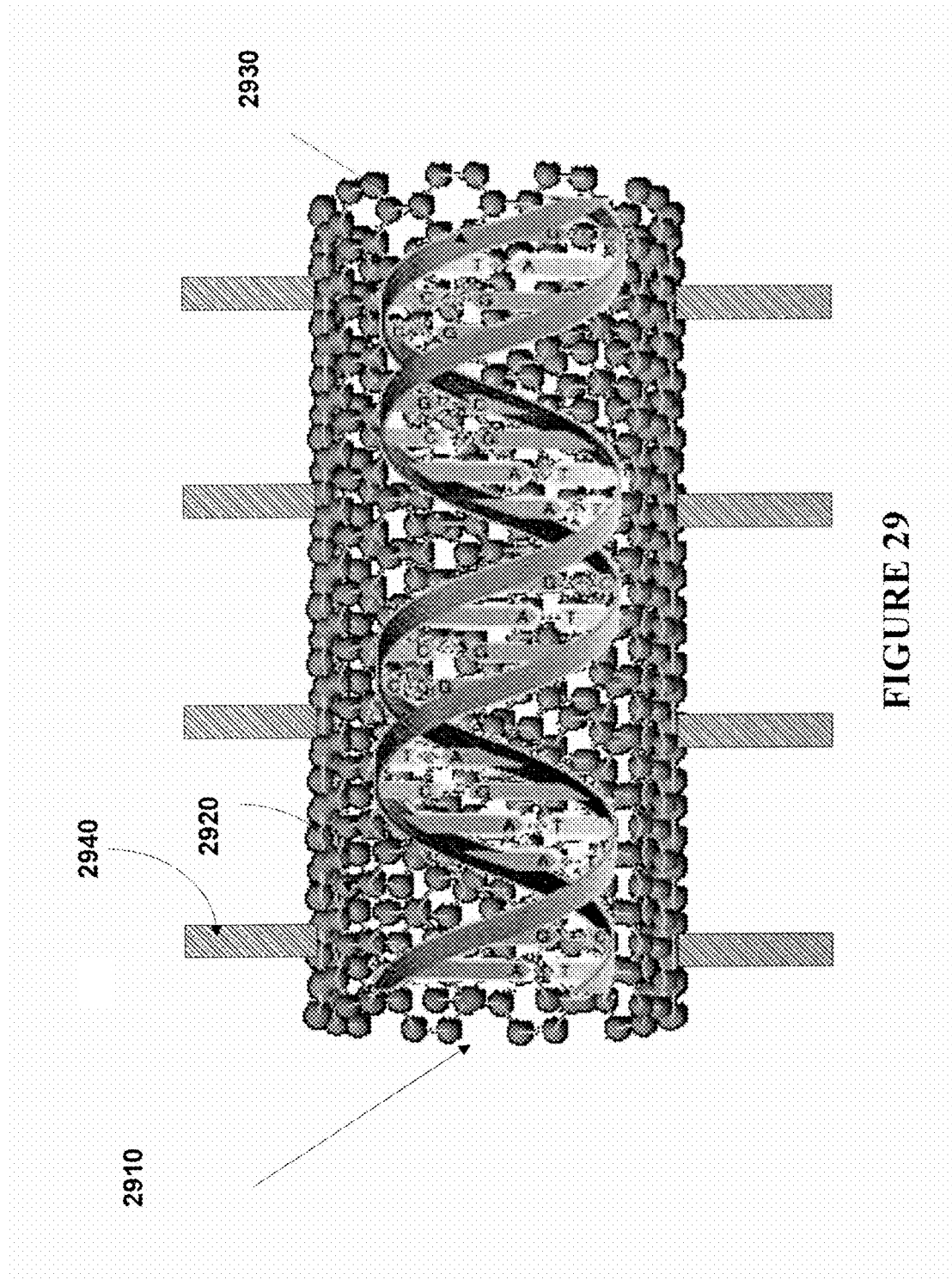

FIG. 29 illustrates an apparatus of this invention that includes a carbon nano-tube as the channel with DNA contained therein.

Figure 30:
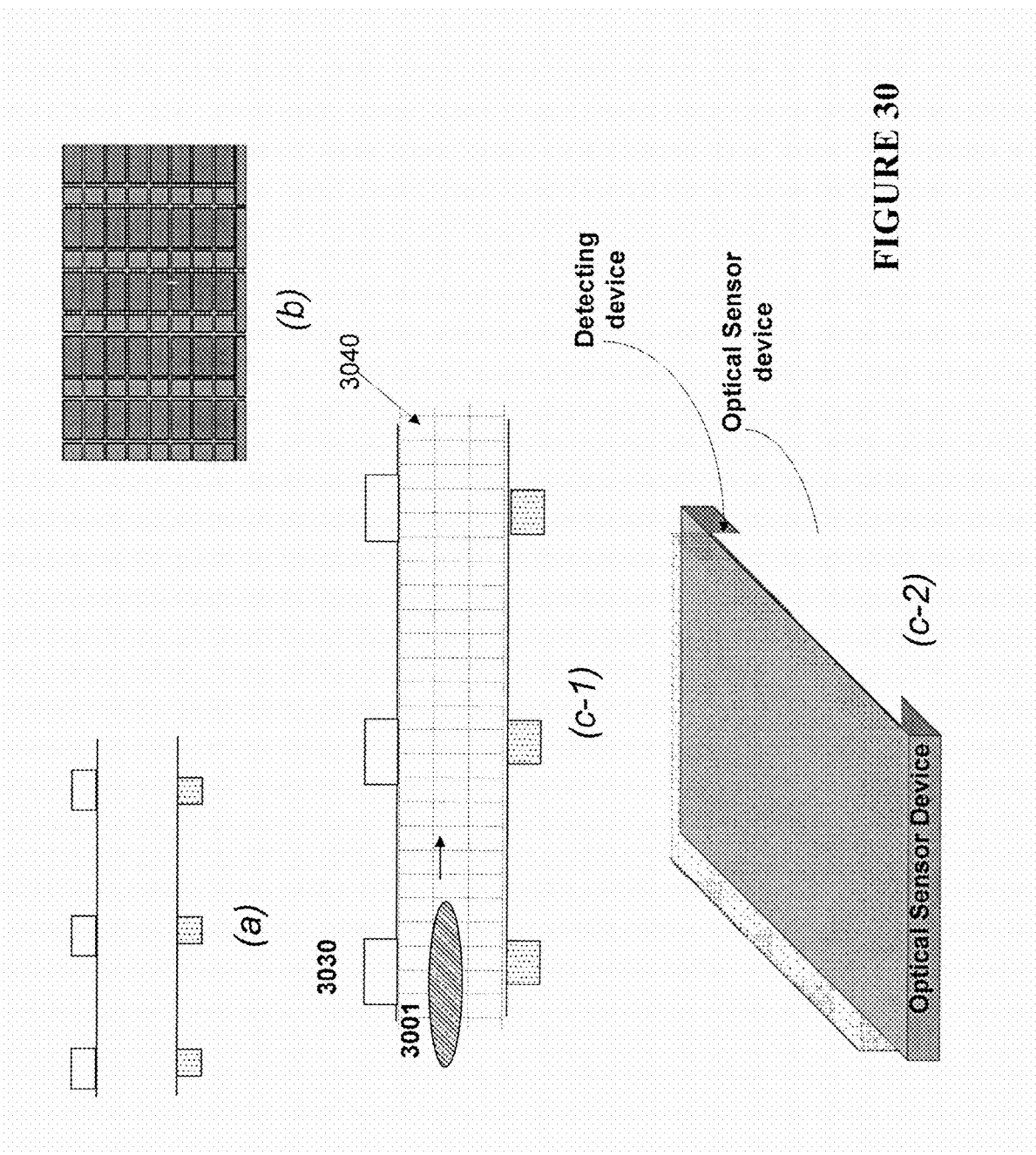
Figure 30:
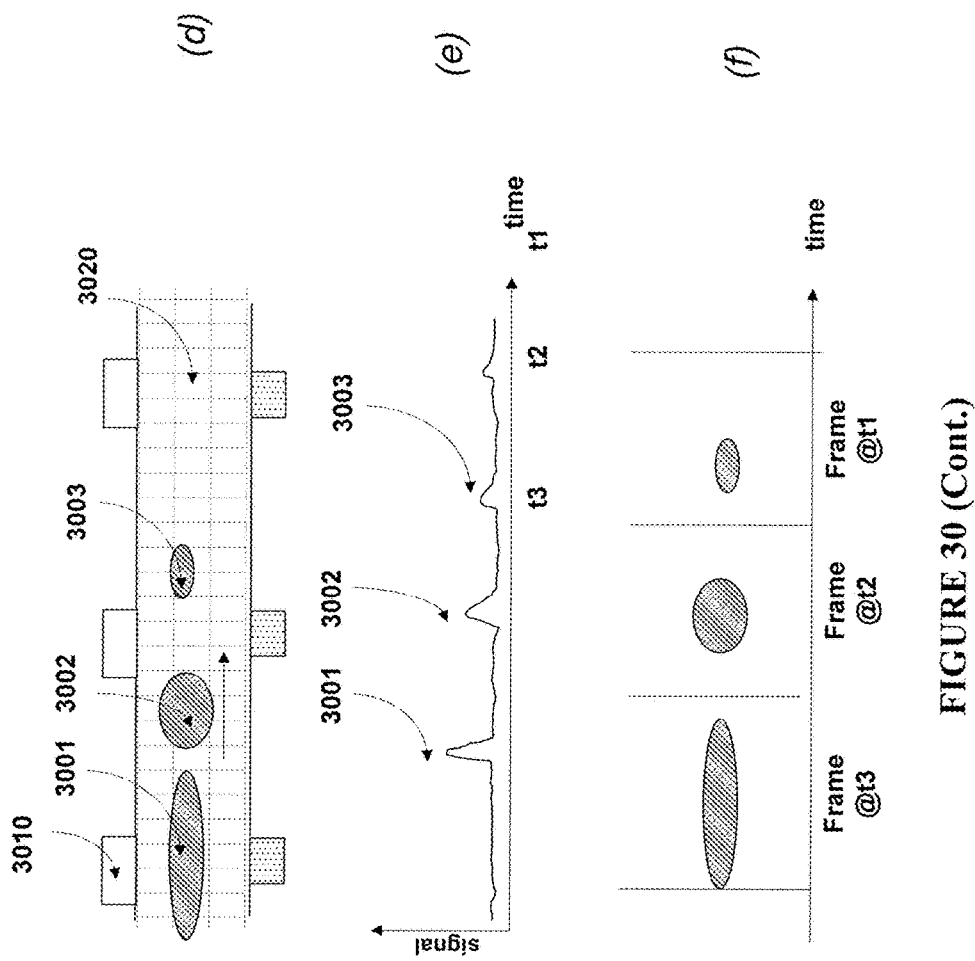

FIG. 30 illustrated an integrated apparatus of this invention that includes a detecting device and an optical sensor.

Figure 31:
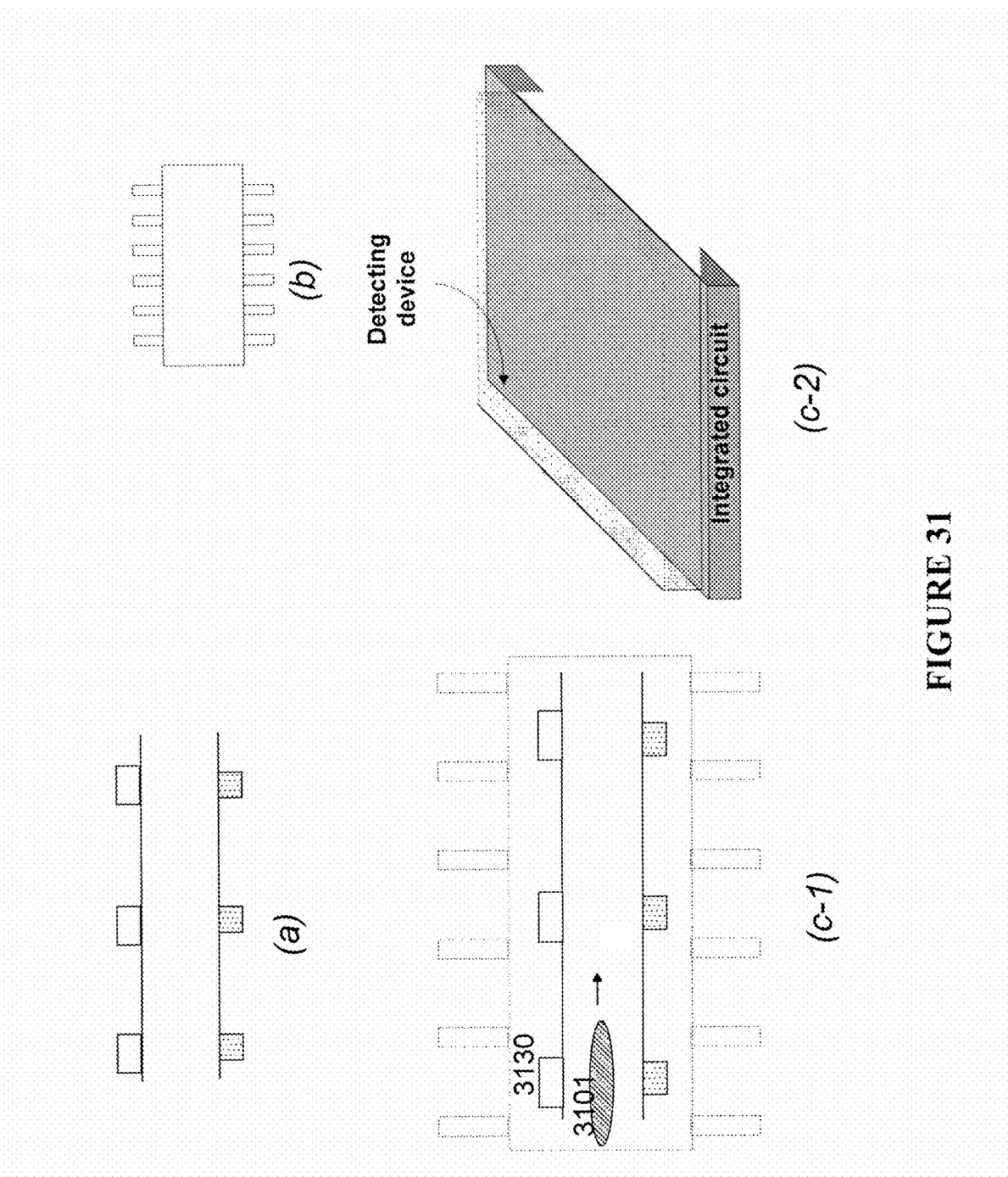

FIG. 31 illustrated an integrated apparatus of this invention that includes a detecting device and a logic circuitry.

Figure 32:
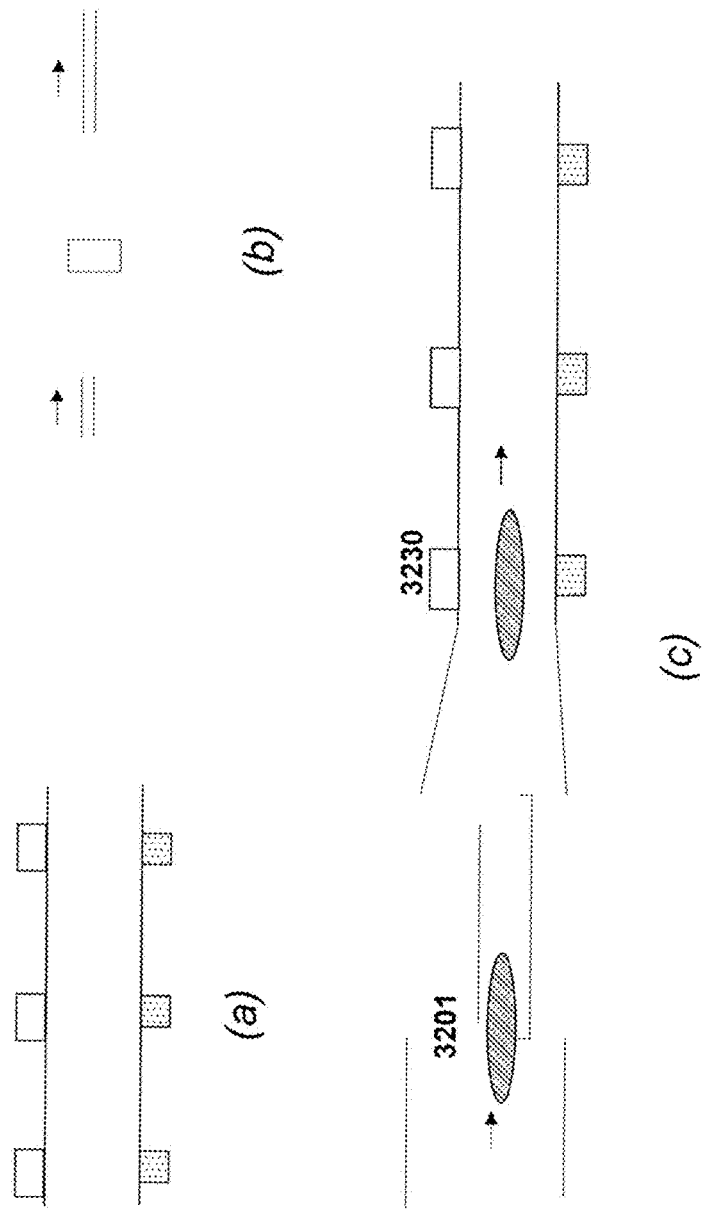

FIG. 32 illustrates an apparatus of this invention that includes a detecting device and a filter.

Figure 33:
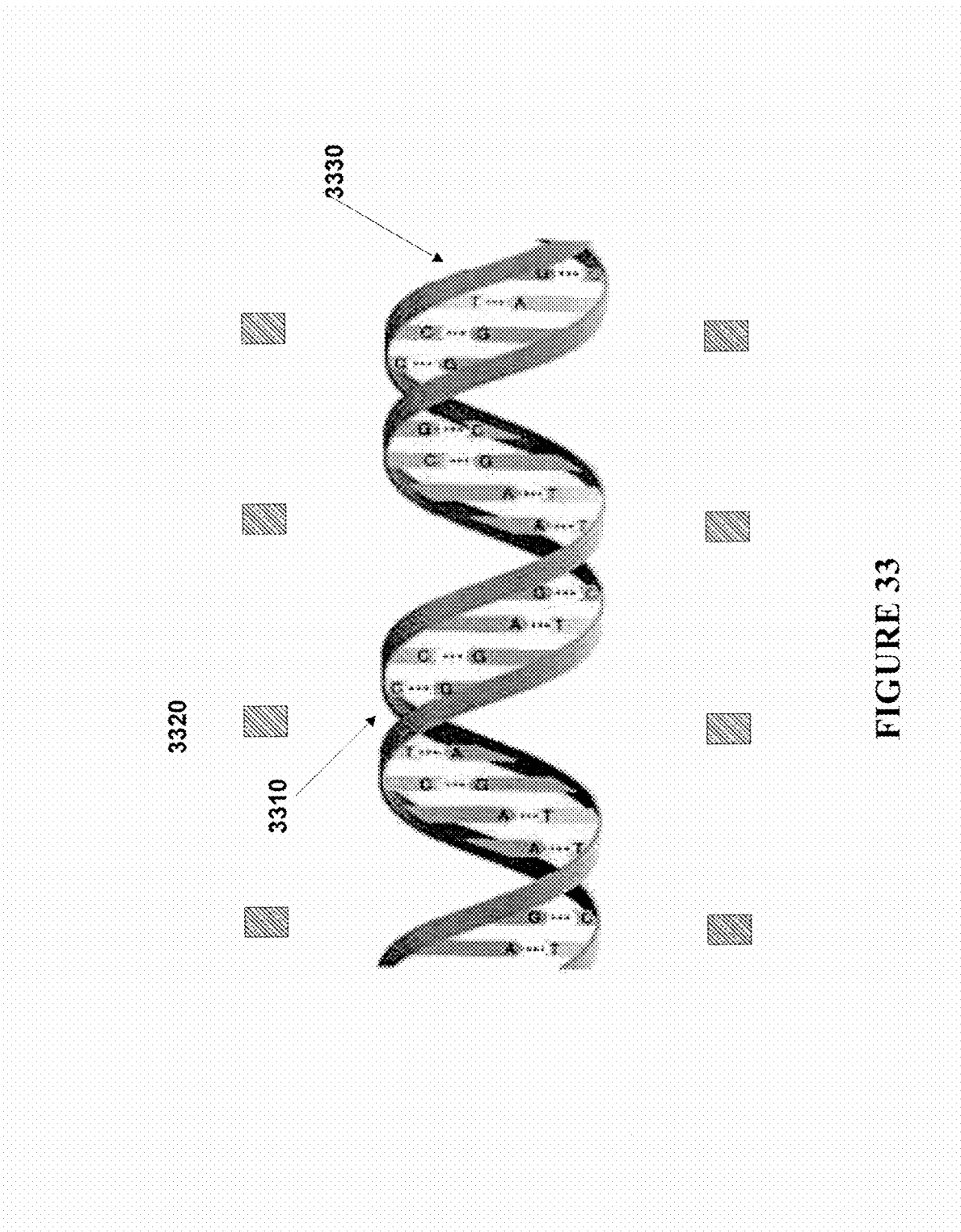

FIG. 33 illustrates how micro-devices of this invention can be used to measure the geometric factors of DNA.

Figure 34:
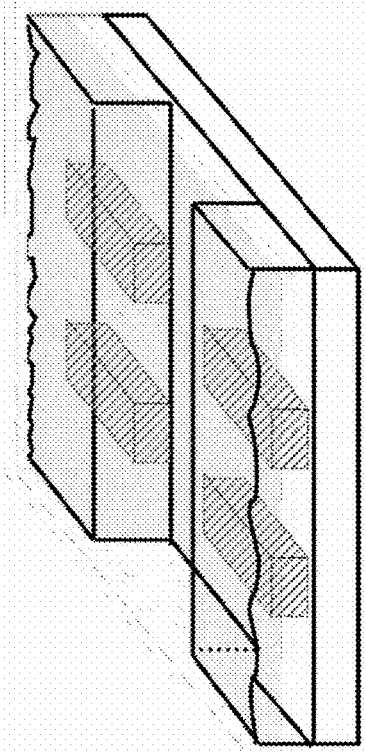

FIG. 34 illustrates a process for fabricating a micro-device of this invention with a cover atop the trench to form a channel.

Figure 35:
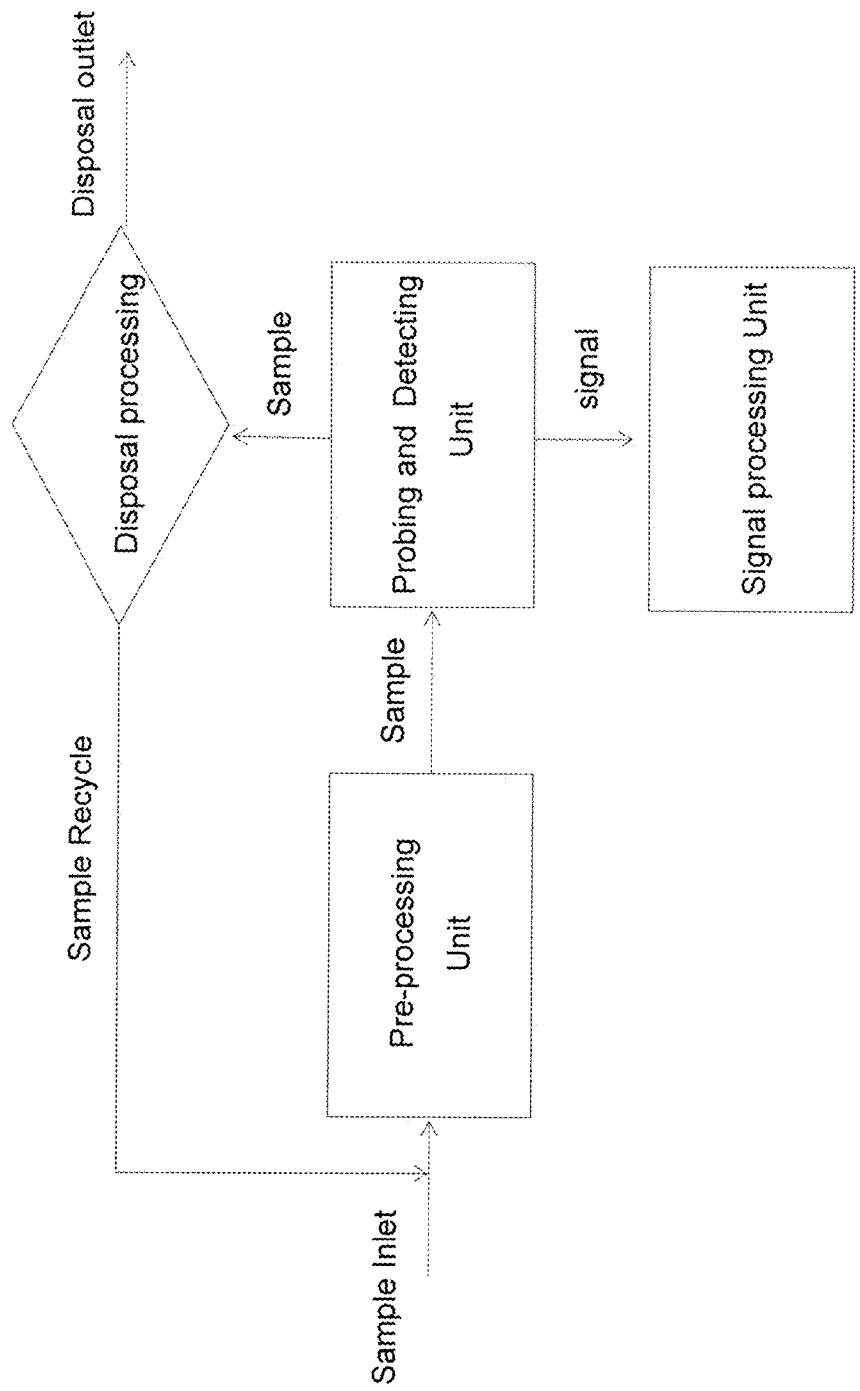

FIG. 35 is a diagram of an apparatus of this invention for detecting a disease in a biological subject.

Figure 36:
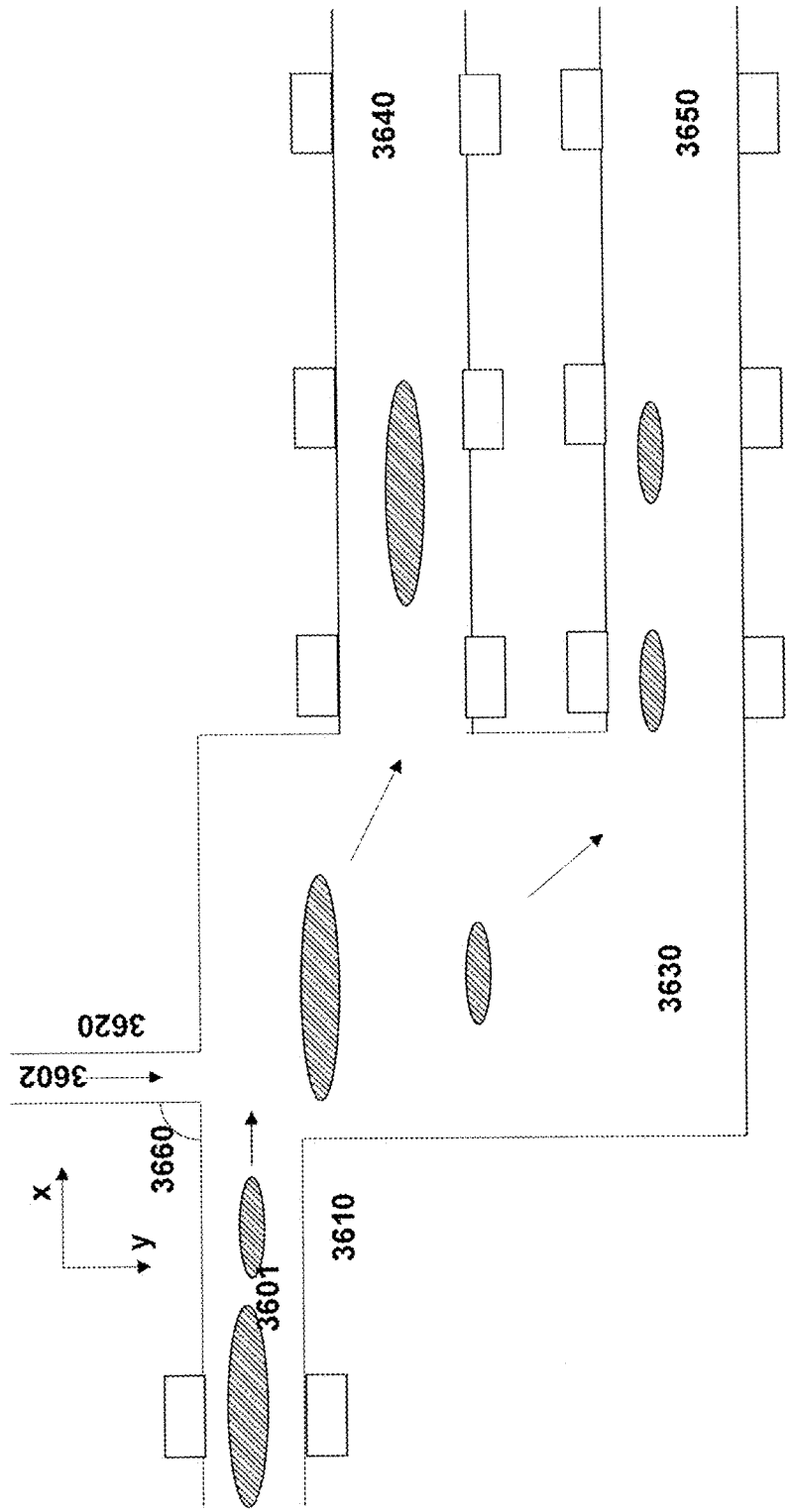

FIG. 36 shows an example of a sample filtration unit.

Figure 37:
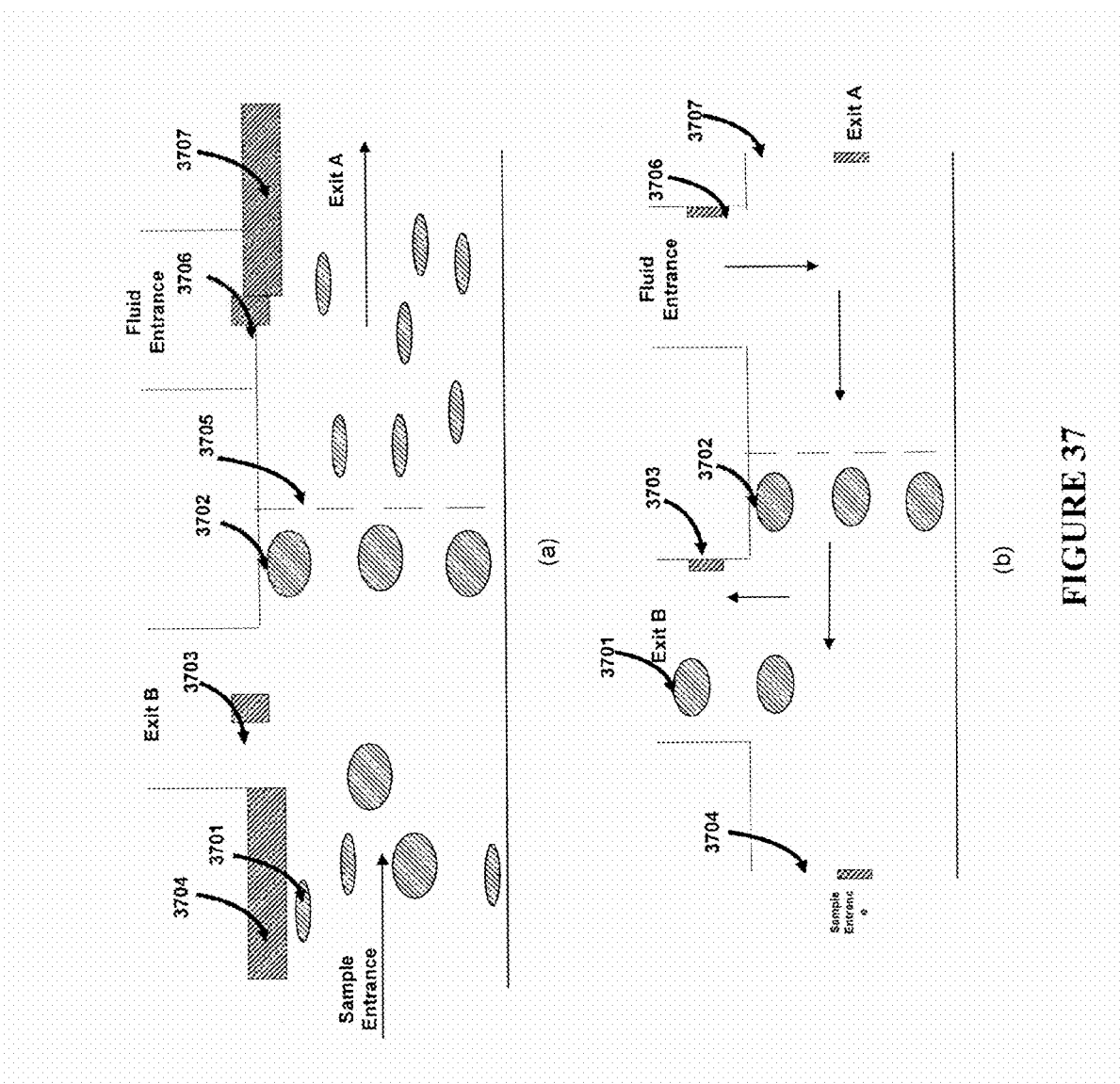

FIG. 37 shows another example of a sample filtration unit.

Figure 38:
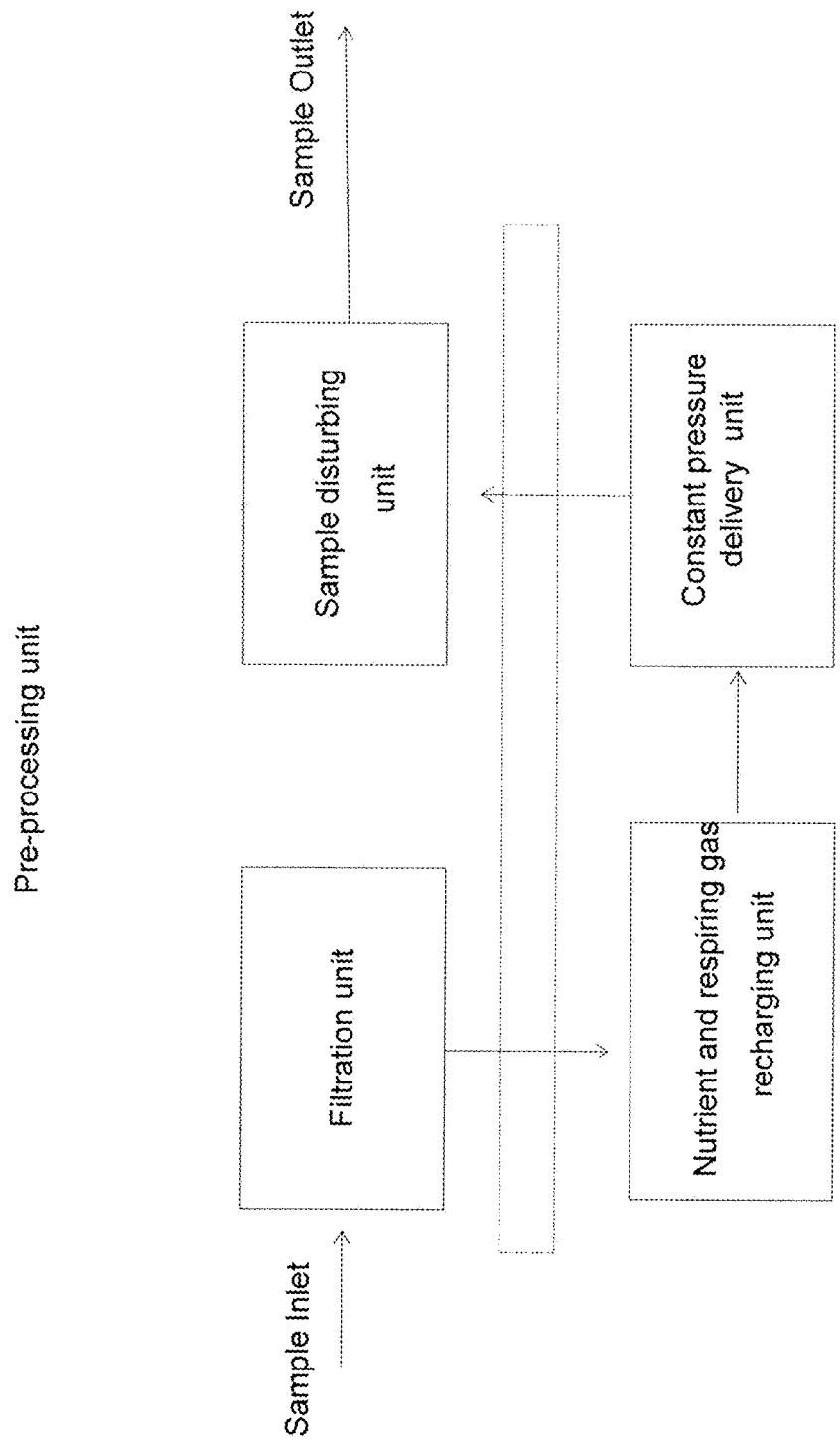

FIG. 38 is a diagram of a pre-processing unit of an apparatus of this invention.

Figure 39:
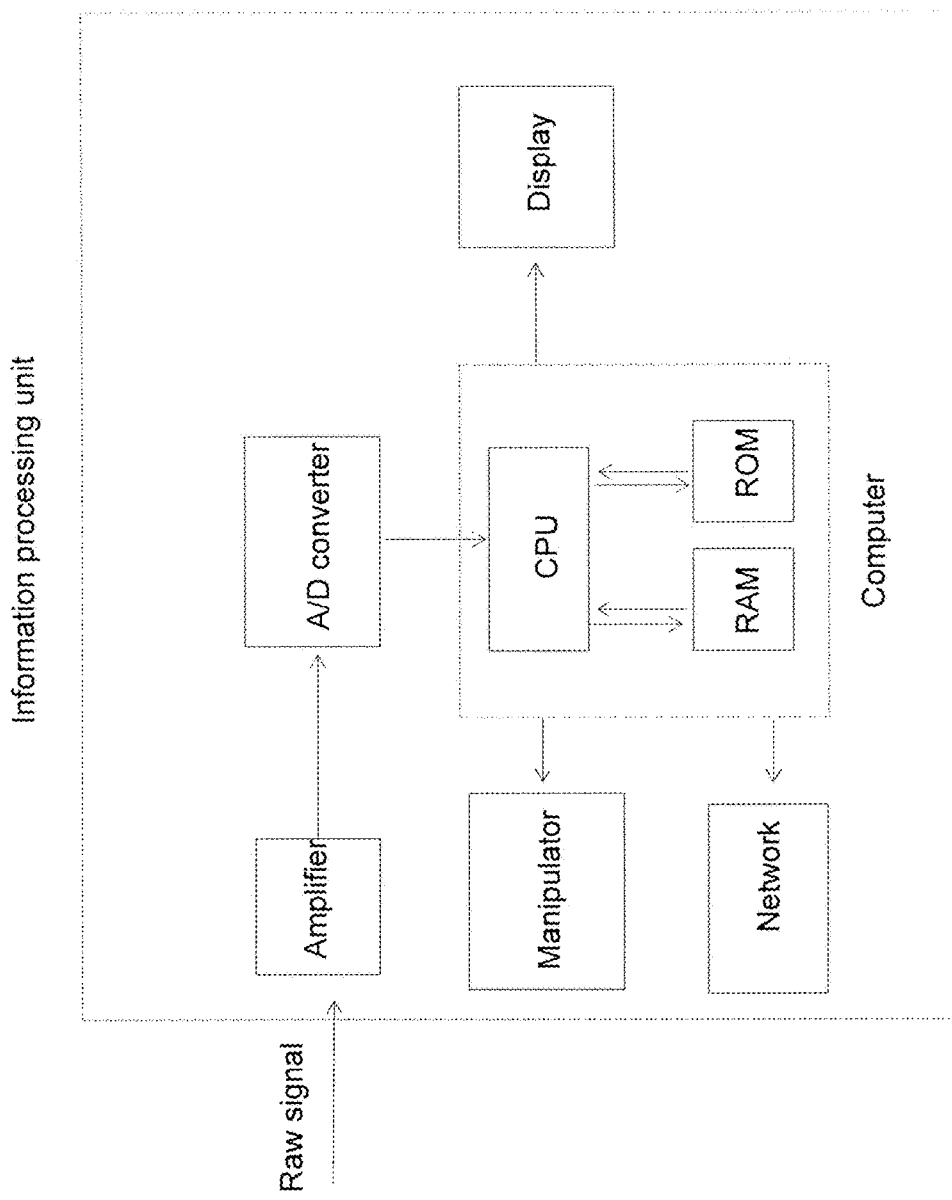

FIG. 39 is a diagram of an information processing unit of an apparatus of this invention.

Figure 40:
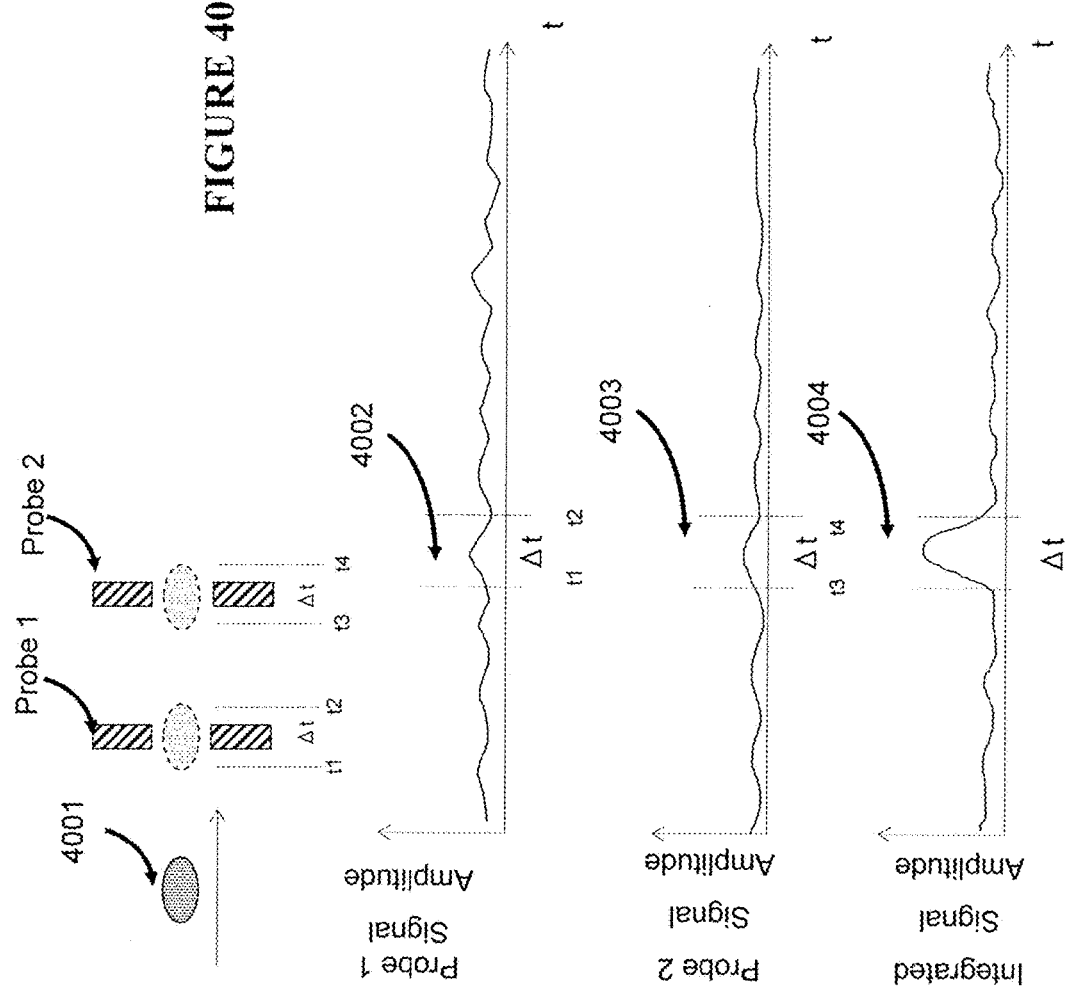

FIG. 40 shows the integration of multiple signals which results in cancellation of noise and enhancement of signal/noise ratio.

Figure 41:
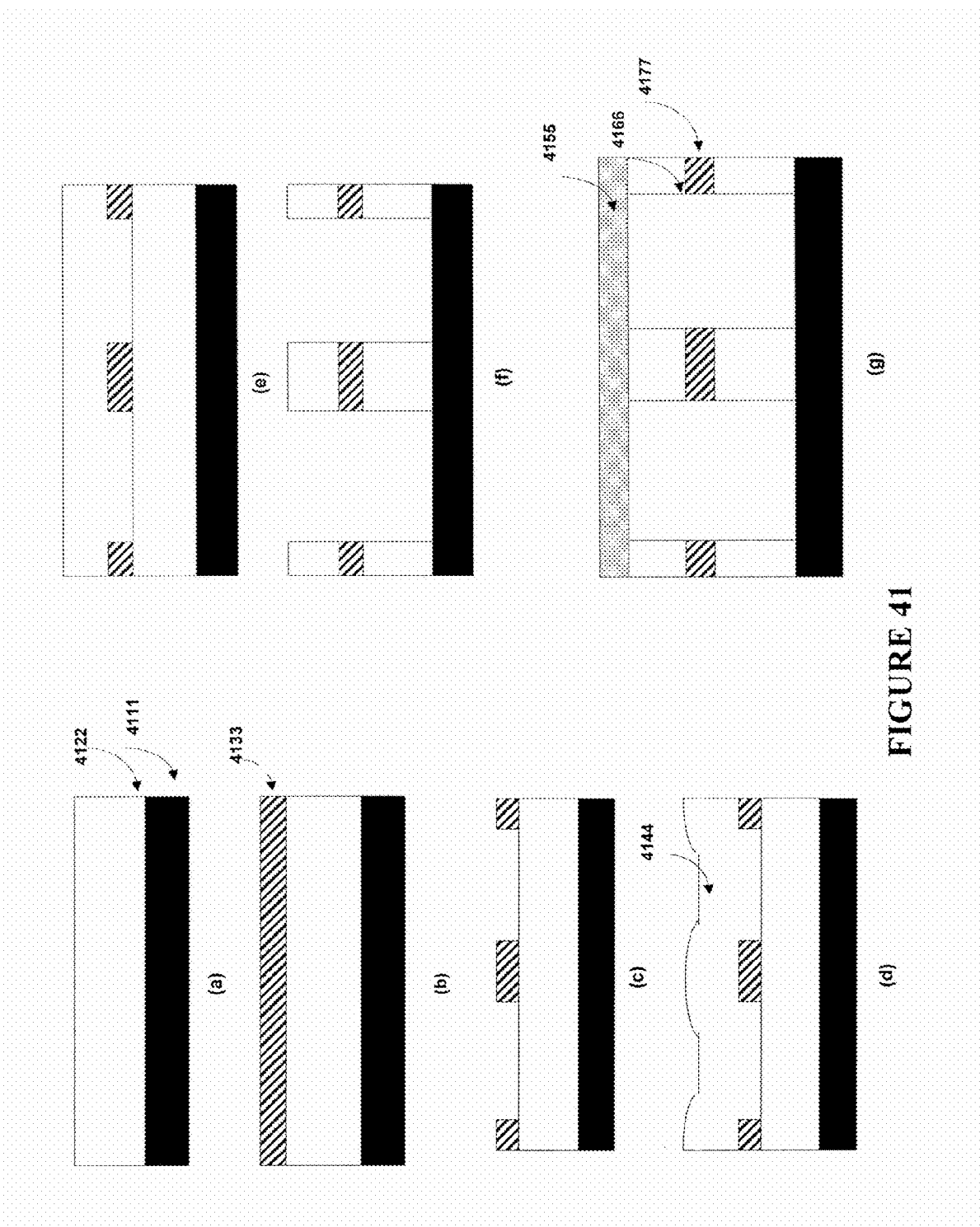

FIG. 41 shows one embodiment of the fabrication process of this invention for manufacturing a detection device with at least one detection chamber and at least one detector.

Figure 42:
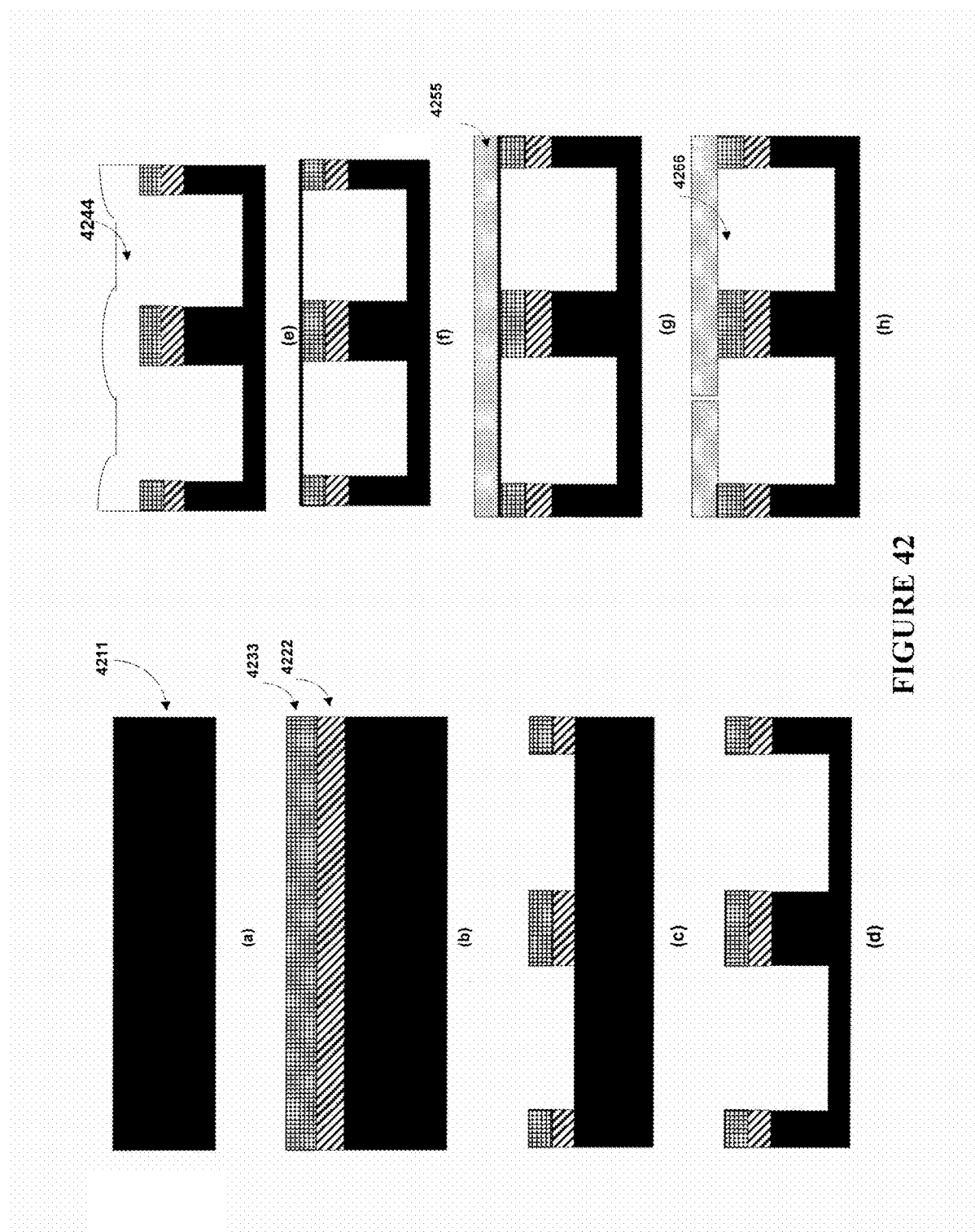
Figure 42:
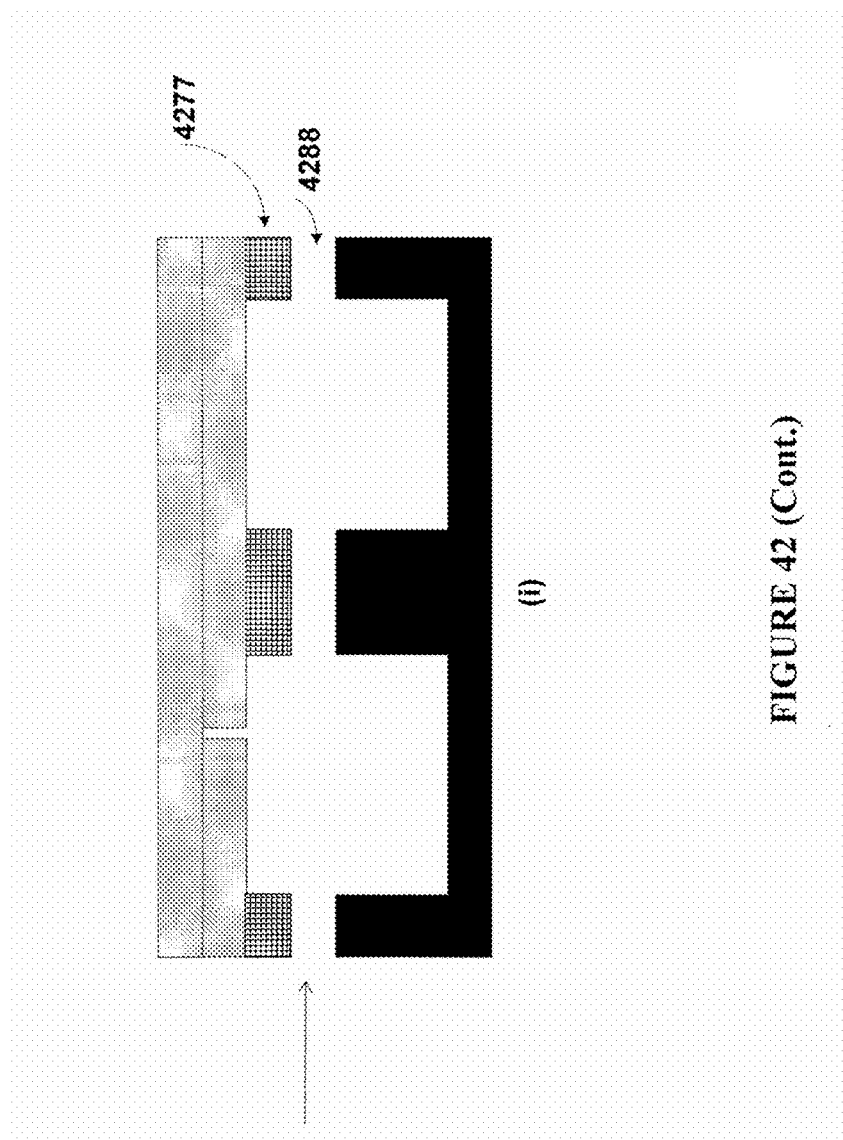

FIG. 42 shows another embodiment of a process of this invention for manufacturing a detection device with enclosed detection chambers, detectors, and channels for transporting biological samples such as fluidic samples.

Figure 43:
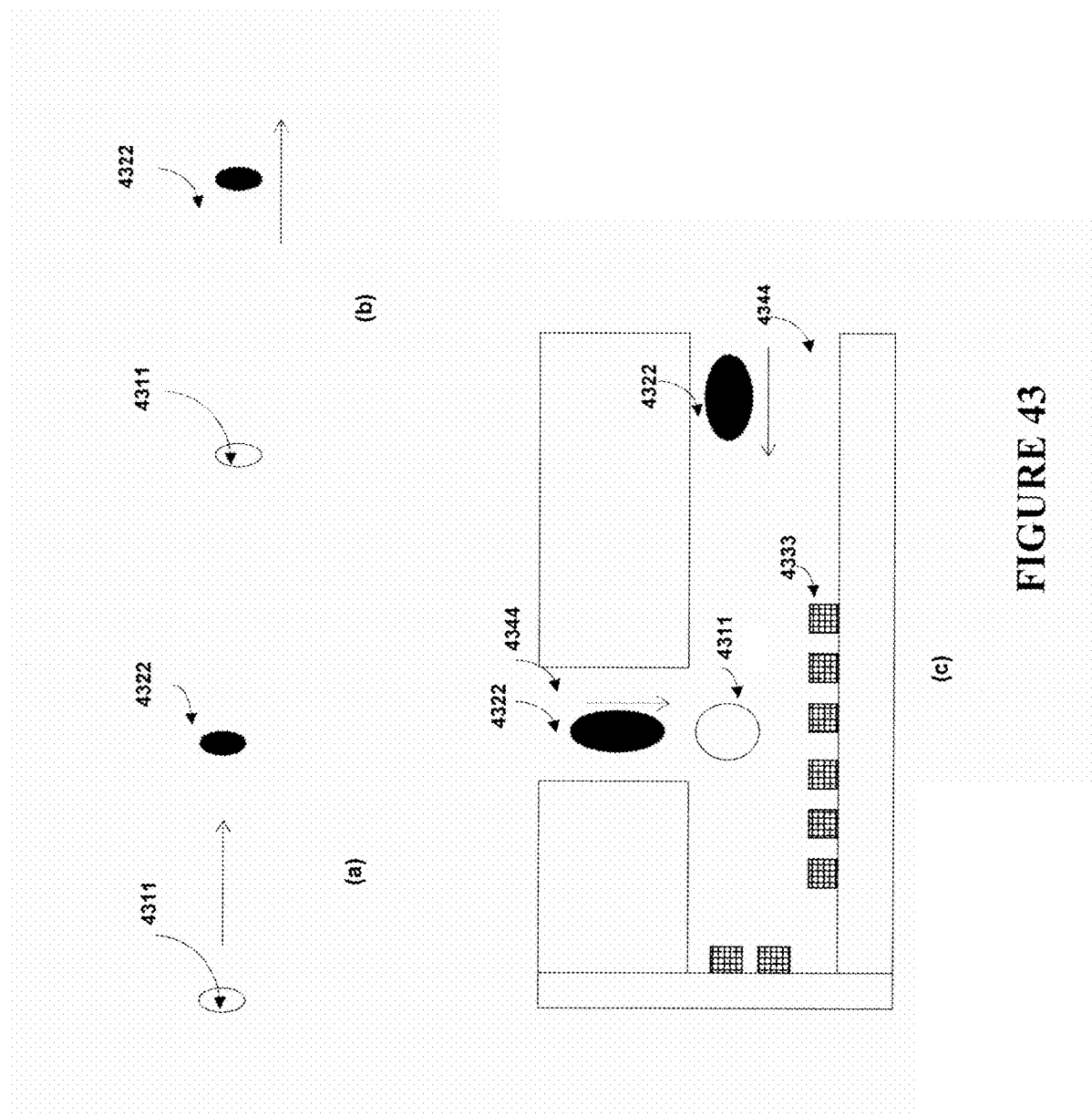

FIG. 43 shows a novel disease detection method in which at least one probe object is launched at a desired speed and direction toward a biological subject, resulting in a collision.

Figure 44:
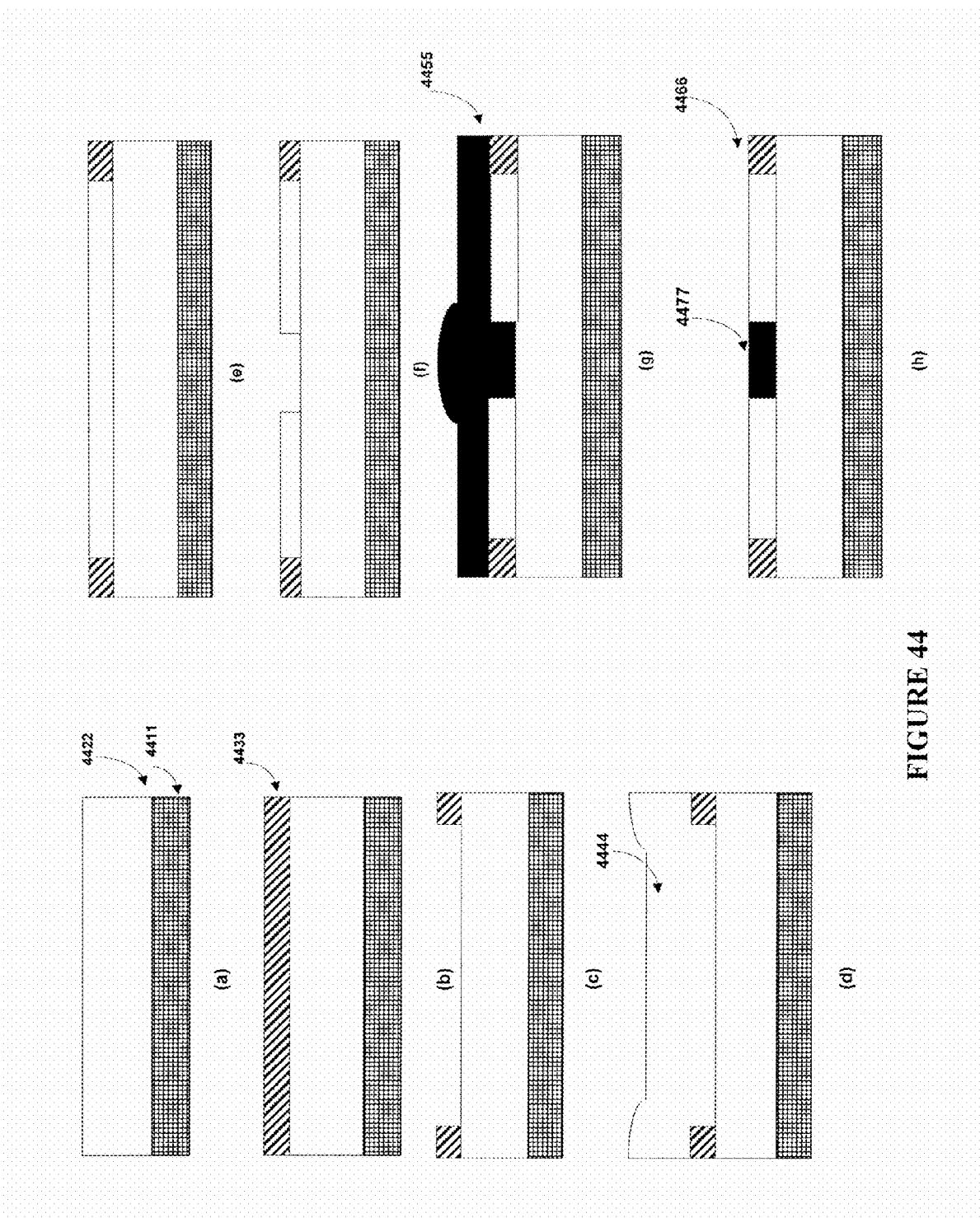

FIG. 44 illustrates a novel fabrication process of this invention for forming multiple components with different materials at the same device level.

Figure 45:
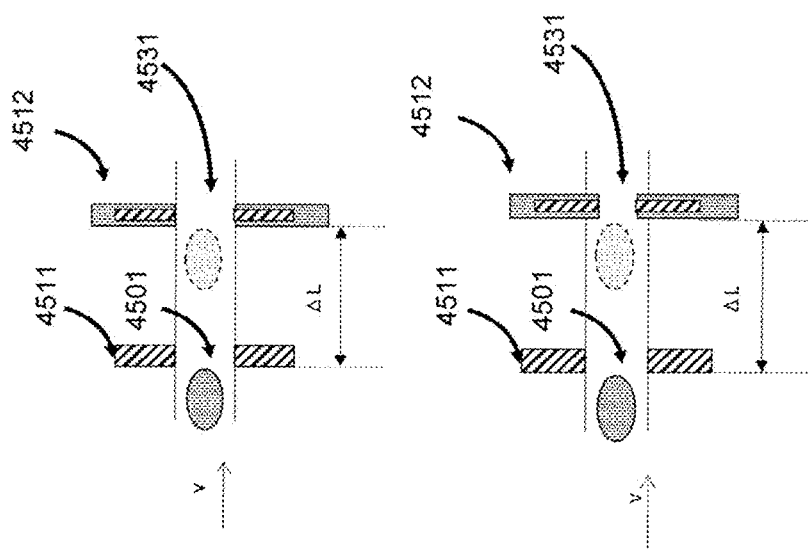

FIG. 45 shows a process of this invention for detecting a biological subject using a disease detection device.

Figure 46:
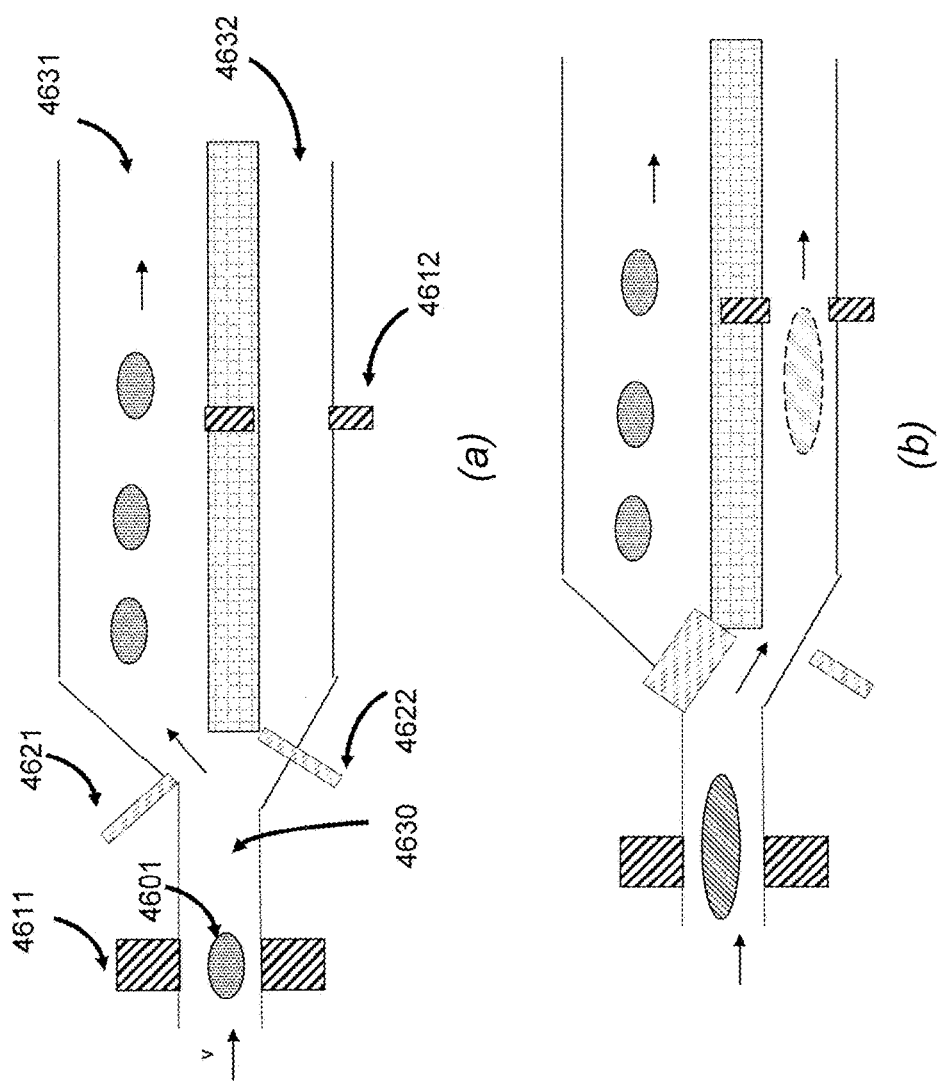

FIG. 46 shows another embodiment of disease detection process wherein diseased and healthy biological subjects are separated and the diseased biological subjects are delivered to further test.

Figure 47:
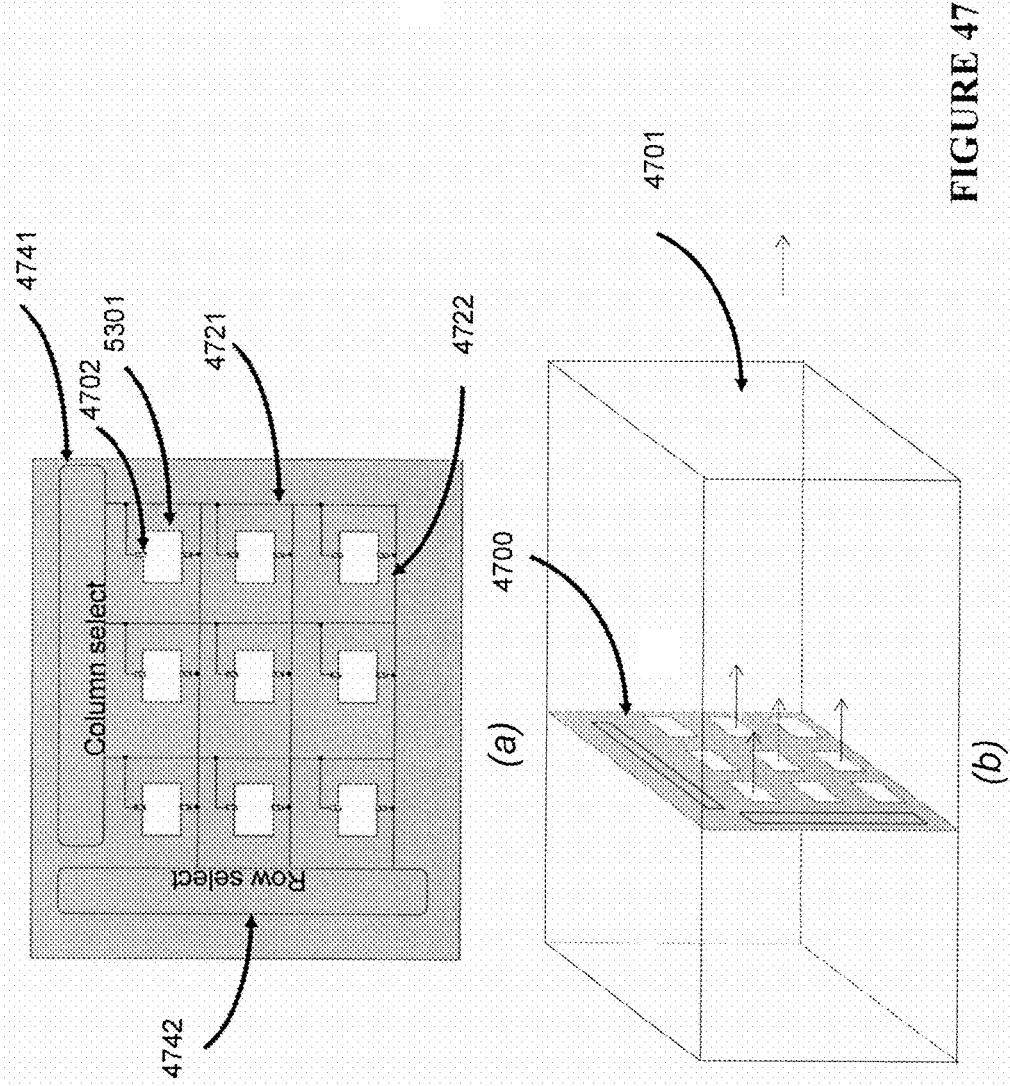

FIG. 47 is an arrayed biological detecting device wherein a series of detecting devices are fabricated into an apparatus.

Figure 48:
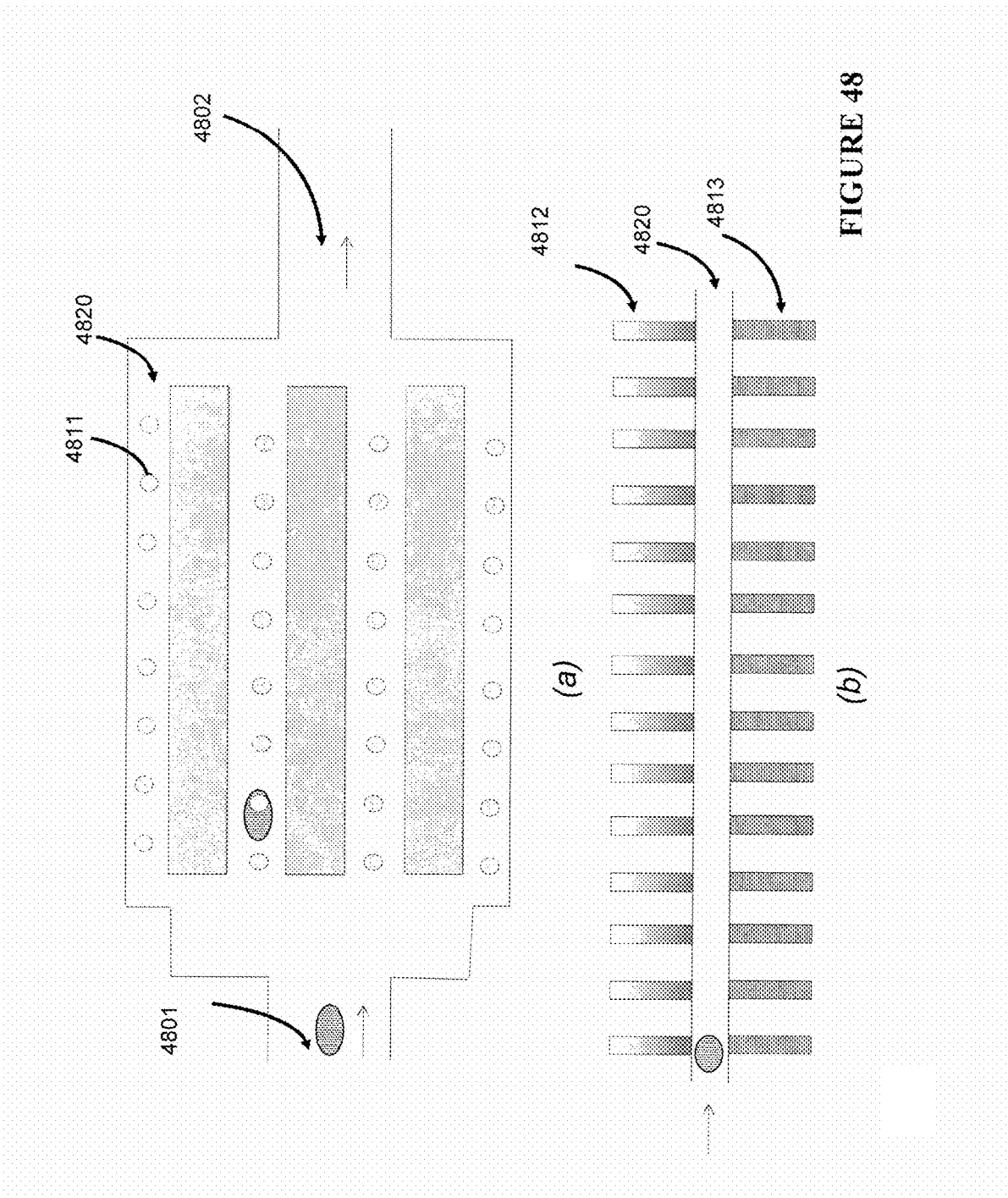

FIG. 48 shows another embodiment of a disease detection device of the current invention including inlet and outlet of the device, the channel where the biological subject passes through, and detection devices aligned along the walls of the channel.

DETAILED DESCRIPTION OF THE INVENTION

One aspect of the present invention relates to apparatus for detecting disease in a biological subject in vivo or in vitro (e.g., human being, an organ, a tissue, or cells in a culture). Each apparatus includes a biological fluid delivering system and a probing and detecting device. The apparatus is capable of measuring microscopic properties of a biological sample. By the constant pressure fluid delivery system, microscopic biological subjects can be delivered onto or into the diagnostic micro-device of the apparatus. Compared to traditional detection apparatus or technologies, the apparatus provided by this invention are advantageous in providing enhanced detection sensitivity, specificity, and speed, with reduced costs and size. The apparatus can further include a biological interface, a probing controlling and data analysis circuitry, or a system reclaiming or treating medical waste. Additional micro-devices, e.g., a second detection device, can also be included or integrated into the apparatus for enhanced detection capabilities.

As a key component of the apparatus, the micro-device should include means to perform at least the function of addressing, controlling, forcing, receiving, amplifying, or storing information from each probing address. As an example, such means can be a central control unit that includes a controlling circuitry, an addressing unit, an amplifier circuitry, a logic processing circuitry, a memory unit, an application specific chip, a signal transmitter, a signal receiver, or a sensor.

In some embodiments, the fluid delivering system comprises a pressure generator, a pressure regulator, a throttle valve, a pressure gauge, and distributing kits. As examples of these embodiments, the pressure generator can include a motor piston system and a bin containing compressed gas; the pressure regulator (which can consist of multiple regulators) can down-regulate or up-regulate the pressure to a desired value; the pressure gauge feeds back the measured value to the throttle valve which then regulates the pressure to approach the target value.

The biological fluid to be delivered can be a sample of a biological subject to be detected for disease or something not necessarily to be detected for disease. In some embodiment, the fluid to be delivered is liquid (e.g., a blood sample, a urine sample, or a saline) or gas (e.g., nitrogen, argon, helium, neon, krypton, xenon, or radon). The pressure regulator can be a single pressure regulator or multiple pressure regulators which are placed in succession to either down-regulate or up-regulate the pressure to a desired level, particularly when the initial pressure is either too high or too low for a single regulator to adjust to the desired level or a level that is acceptable for an end device or target.

In some other embodiments, the system controller includes a pre-amplifier, a lock-in amplifier, an electrical meter, a thermal meter, a switching matrix, a system bus, a nonvolatile storage device, a random access memory, a processor, or a user interface. The interface can include a sensor which can be a thermal sensor, a flow meter, a piezo-meter, or another sensor.

In still some other embodiments, apparatus of this invention further include a biological interface, a system controller, a system for reclaiming or treatment medical waste. The reclaiming and treatment of medical waste can be performed by the same system or two different systems.

Another aspect of this invention provides apparatus for interacting with a cell, which include a device for sending a signal to the cell and optionally receiving a response to the signal from the cell.

In some embodiments, the interaction with the cell can be probing, detecting, communicating with, treating, or modifying with a coded signal that can be an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical signal, or a combination thereof.

In some other embodiments, the device contained in the apparatus can include multiple surfaces coated with one or more elements or combinations of elements, and a control system for releasing the elements. In some instances, the control system can cause release of the elements from the device surface via thermal energy, optical energy, acoustic energy, electrical energy, electro-magnetic energy, magnetic energy, radiation energy, or mechanical energy in a controlled manner. The energy can be in the pulsed form at desired frequencies.

In some other embodiments, the device contained in the apparatus include a first component for storing or releasing one element or a combination of elements onto the surface of the cell or into the cell; and a second component for controlling the release of the elements (e.g., a circuitry for controlling the release of the elements). The elements can be a biological component, a chemical compound, Ca, C, Cl, Co, Cu, H, I, Fe, Mg, Mn, N, O, P, F, K, Na, S, Zn, or a combination thereof. The signal, pulsed or constant, can be in the form of a released element or combination of elements, and it can be carried in a liquid solution, gas, or a combination thereof. In some instances, the signal can be at a frequency ranging from about $1 \times 10^{-4}$ Hz to about 100 MHz or ranging from about $1 \times 10^{-4}$ Hz to about 10 Hz, or at an oscillation concentration ranging from about 1.0 nmol/L to about 10.0 mmol/L. Also, the signal comprises the oscillation of a biological component, a chemical compound, Ca, C, Cl, Co, Cu, H, I, Fe, Mg, Mn, N, O, P, F, K, Na, S, Zn, or a combination thereof, e.g., at desired oscillating frequencies.

In some embodiments, the signal to be sent to the cell can be in the form of oscillating element, compound, or an oscillating density of a biological component, and a response to the signal from the cell is in the form of oscillating element, compound, or an oscillating density of a biological component.

In some embodiments, the device can be coated with a biological film, e.g., to enhance compatibility between the device and the cell.

In some other embodiments, the device can include components for generating a signal to be sent to the cell, receiving a response to the signal from the cell, analyzing the response, processing the response, and interfacing between the device and the cell.

Still another aspect of this invention provides devices each including a micro-filter, a shutter, a cell counter, a selector, a micro-surgical kit, a timer, and a data processing circuitry. The micro-filter can discriminate abnormal cells by a physical property (e.g., e.g., dimension, shape, or velocity), mechanical property, electric property, magnetic property, electromagnetic, thermal property (e.g., temperature), optical property, acoustical property, biological property, chemical property, or bio-chemical property. The devices each can also include one or more micro-filters. Each of these micro-filters can be integrated with two cell counters, one of which is installed at the entrance of each filter well, while the other is installed at the exit of each filter well. The shape of the micro-filter's well is rectangle, ellipse, circle, or polygon; and the micro-filter's dimension ranges from about 0.1 μm to about 500 μm or from about 5 um to about 200 um. As used herein, the term "dimension" means the physical or feature size of the filter opening, e.g., diameter, length, width, or height. The filter can be coated with a biological or bio-compatible film, e.g., to enhance compatibility between the device and the cell.

In some embodiments of these devices, the shutter sandwiched by two filter membranes can be controlled by a timer (thus time shutter). The timer can be triggered by the cell counter. For instance, when a cell passes through the cell counter of the filter entrance, the clock is triggered to reset the shutter to default position, and moves at a preset speed towards the cell pathway, and the timer records the time as the cell pass through the cell counter at the exit.

Figure 2:
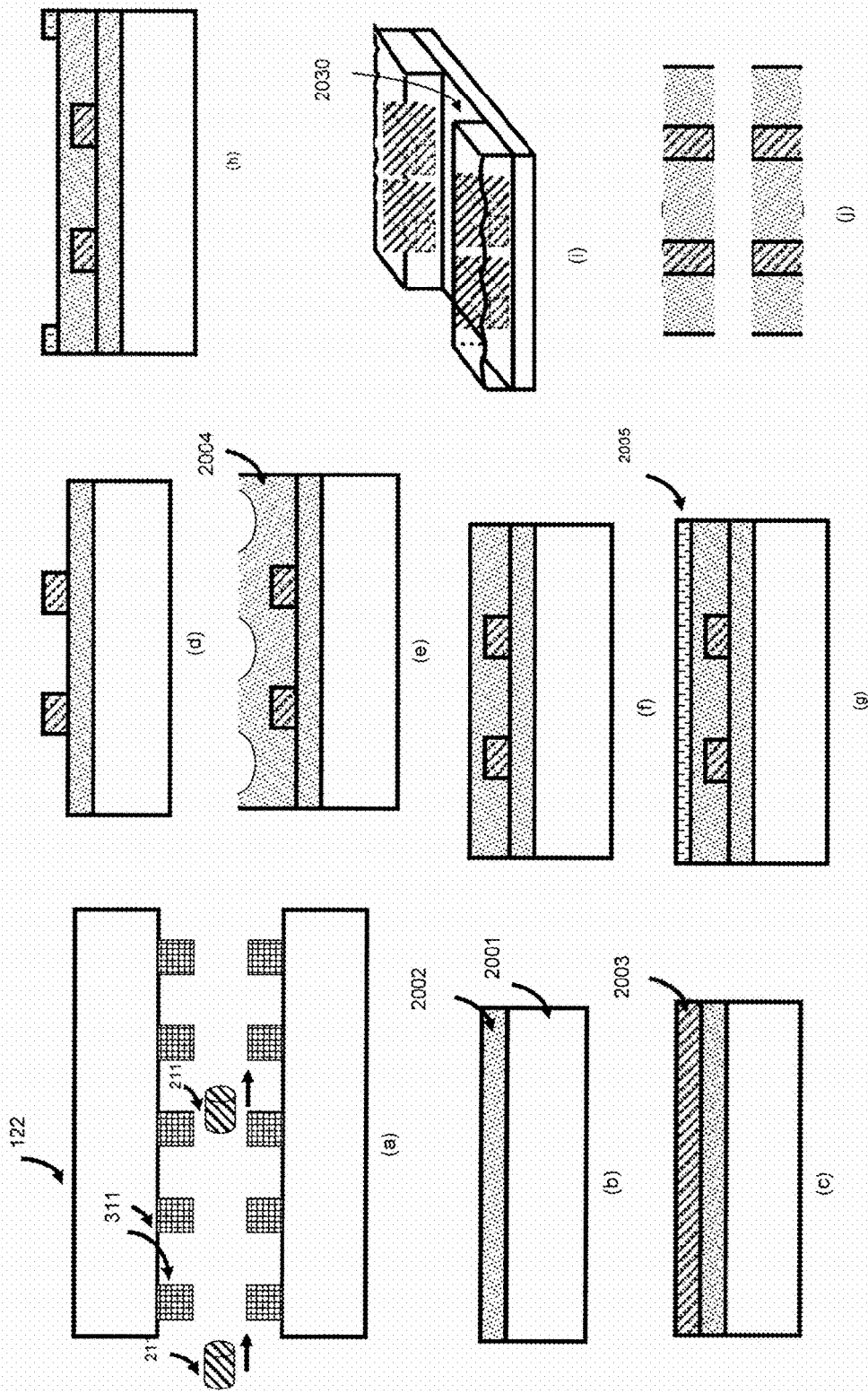
Figure 2:
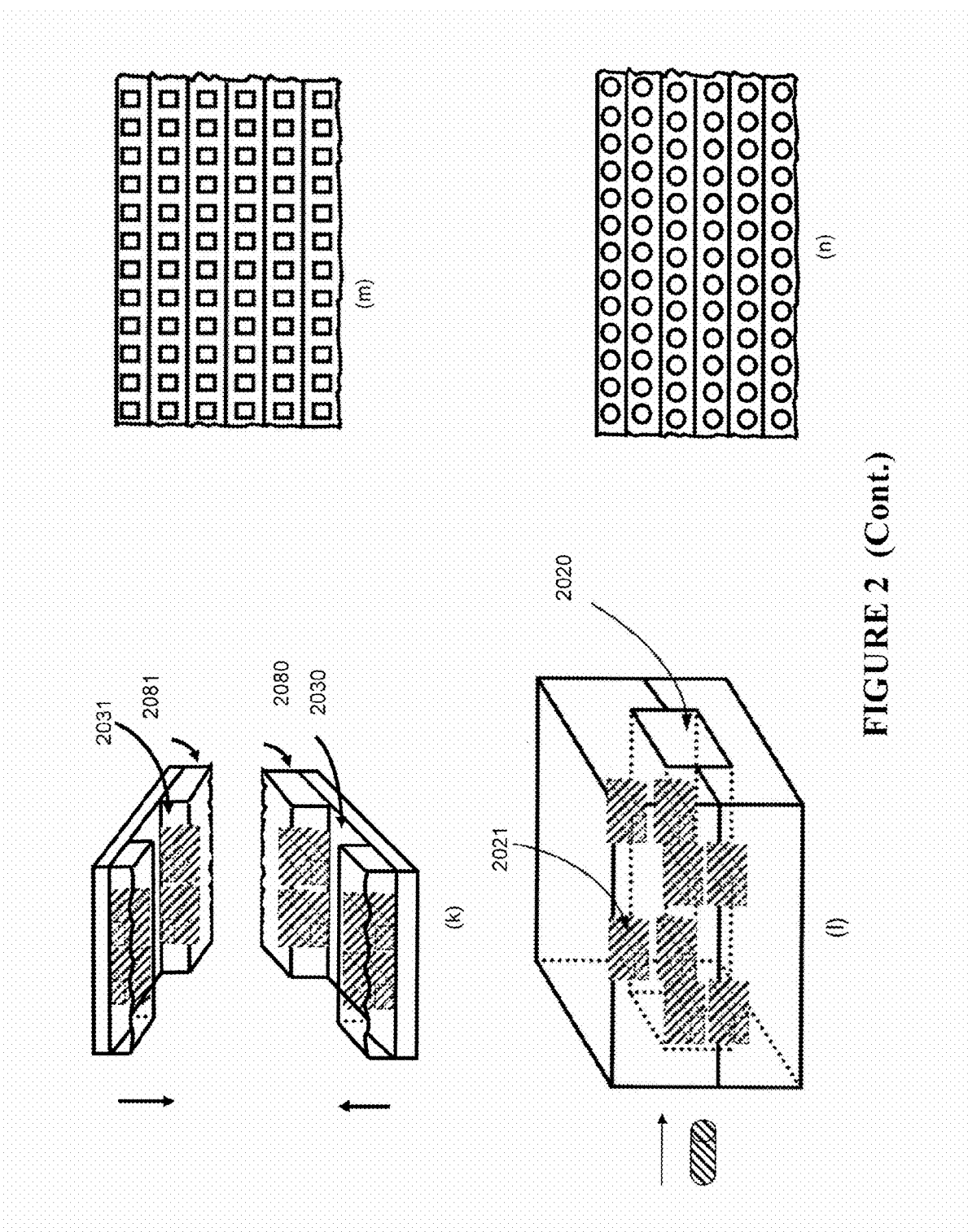

Still a further aspect of this invention provides methods for fabricating a micro-device with micro-trench and probe embedded in the micro-trench's sidewalls. A micro-trench is an unclosed tunnel (see, e.g., FIG. 2(*i*), 2030), which can be coupled with another upended symmetric trench (see, e.g., FIG. 2(*k*), 2031) to form a closed channel (see, e.g., FIG. 2(*l*), 2020). The method may include chemical vapor deposition, physical vapor deposition, or atomic layer deposition to deposit various materials on a substrate; lithography or etch to transfer patterns from design to structure; chemical mechanical planarization for surface planarization, chemical cleaning for particle removal, diffusion or ion implantation for doping elements into specific layers; or thermal anneal to reduce the crystal defects and activate diffused ions. An example of such method includes: depositing a first material onto a substrate; depositing a second material onto the first material and patterning the second material by a microelectronic process (e.g., lithography, etch) to form a detecting tip; depositing a third material on the second material and then patterning the second material by a planarization process; depositing a fourth material on the third material and patterning the fourth material first by a microelectronic process (e.g., lithography, etch) and then by a microelectronic process (e.g., another etch) in which the fourth material serves as a hardmask. A hardmask generally refers to a material (e.g., inorganic dielectric or metallic compound) used in semiconductor processing as an etch mask in lieu of polymer or other organic "soft" materials.

In some embodiments, the method further includes coupling two devices that are thus fabricated and symmetric (i.e., a flipped mirror) to form a detecting device with channels. The entrance of each channel can be optionally bell-mouthed, e.g., such that the size of channel's opening end (the entrance) is larger than the channel's body, thereby making it easier for a cell to enter the channel. The shape of each channel's cross-section can be rectangle, ellipse, circle, or polygon. The micro-trenches of the coupled two micro-devices can be aligned by the module of alignment marks designed on the layout of the micro-device. The dimension of the micro-trench can range from about 0.1 um to about 500 um.

Alternatively, the method can also include covering the micro-trench of the micro-device with a flat panel. Such a panel can comprise or be made with silicon, SiGe, $SiO_2$, $Al_2O_3$, or other optical materials. Examples of other potentially suitable optical materials include acrylate polymer, AgInSbTe, synthetic alexandrite, arsenic triselenide, arsenic trisulfide, barium fluoride, CR-39, cadmium selenide, caesium cadmium chloride, calcite, calcium fluoride, chalcogenide glass, gallium phosphide, GeSbTe, germanium, germanium dioxide, glass code, hydrogen silsesquioxane, Iceland spar, liquid crystal, lithium fluoride, lumicera, METATOY, magnesium fluoride, magnesium oxide, negative index metamaterials, neutron super mirror, phosphor, picarin, poly(methyl methacrylate), polycarbonate, potassium bromide, sapphire, scotophor, spectralon, speculum metal, split-ring resonator, strontium fluoride, yttrium aluminum garnet, yttrium lithium fluoride, yttrium orthovanadate, ZBLAN, zinc selenide, and zinc sulfide.

In other embodiments, the method can further include integrating three or more micro-devices thus fabricated to yield an enhanced device with an array of the channels.

Yet still another aspect of this invention relates to micro-devices each including a micro-trench, a probe embedded aside the trench's side walls or bottom floor, a supporting structure to move the probe, and a controlling circuitry, wherein the micro-device is capable of trapping, sorting, or modifying a DNA and measuring its properties (e.g., electrical, thermal, or optical properties). The micro-trench can be utilized to encase the DNA double helix.

In some embodiments, the width of the micro-trench ranges from about 1 nm to about 10 μm, the depth of the micro-trench ranges from about 1 nm to about 10 μm, or the length of the micro-trench ranges from about 1 nm to about 10 mm. The probe can include or be made of a conductive material and, optionally, a flexible supporting structure to extend or contract the probe. The probe can also have a tip aside the trench and the tip matches spatially with either a major groove or a minor groove of the DNA. The tip can match spatially with interlaced grooves of the DNA, which can be variable. The tip of can also match the end of each strand of the DNA helix. In some examples, the tip's diameter can range from about 1 angstrom to about 10 μm.

In some other embodiments, the micro-device can further include an array of trenches, e.g., to enhance the efficiency.

Another aspect of this invention relates to a set of novel process flows for fabricating micro-devices (including micro-probes and micro-indentation probes) for their applications in disease detection by measuring microscopic properties of a biological sample. The micro-devices can be integrated into a disease detection apparatus of this invention to measure one or more properties at microscopic levels.

Another aspect of this invention is to involve in cellular communications and regulate cellular decision or response (such as differentiation, dedifferentiation, cell division and cell death) with fabricated signals. This could be further employed to detect and treat diseases.

To further enhance measurement capabilities, multiple micro-devices can be implemented into a piece of detection apparatus employing the time of flight technique, in which at least one probing micro-device and one sensing micro-device placed at a preset, known distance. The probing micro-device can apply a signal (e.g., a voltage, a charge, an electrical field, a laser beam, or an acoustic wave) to the biological sample to be measured, and the detection (sensing) micro-device can measure response from or of the biological sample after the sample has traveled a known distance and a desired period of time. For instance, a probing micro-device can apply an electrical charge to a cell first, and then a detection (sensing) micro-device subsequently measures the surface charge after a desired period of time (T) has lapsed and the cell has traveled a certain distance (L).

The micro-devices contained in the apparatus of this invention can have a wide range of designs, structures, functionalities, and applications due to their diverse properties, high degree of flexibilities, and ability of integration and miniaturization. They include, e.g., a voltage comparator, a four point probe, a calculator, a logic circuitry, a memory unit, a micro cutter, a micro hammer, a micro shield, a micro dye, a micro pin, a micro knife, a micro needle, a micro thread holder, micro tweezers, a micro optical absorber, a micro mirror, a micro wheeler, a micro filter, a micro chopper, a micro shredder, micro pumps, a micro absorber, a micro signal detector, a micro driller, a micro sucker, a micro tester, a micro container, a signal transmitter, a signal generator, a friction sensor, an electrical charge sensor, a temperature sensor, a hardness detector, an acoustic wave generator, an optical wave generator, a heat generator, a micro refrigerator and a charge generator.

Further, it should be noted that advancements in manufacturing technologies have now made fabrications of a wide range of micro-devices and integration of various functions onto the same device highly feasible and cost effective. The typical human cell size is about 10 microns. Using state-of-the-art integrated circuit fabrication techniques, the minimum feature size defined on a micro-device can be as small as 0.1 micron or below. Thus, it is ideal to utilize the disclosed micro-devices for biological applications.

In terms of materials for the micro-devices, the general principle or consideration is the material's compatibility with a biological subject. Since the time in which a micro-device is in contact with a biological sample (e.g., a cell; a biological molecule such as DNA, RNA, or protein; or a tissue or organ sample) may vary, depending on its intended application, a different material or a different combination of materials may be used to make the micro-device. In some special cases, the materials may dissolve in a given pH in a controlled manner and thus may be selected as an appropriate material. Other considerations include cost, simplicity, ease of use and practicality. With the significant advancements in micro fabrication technologies such as integrated circuit manufacturing technology, highly integrated devices with minimum feature size as small as 0.1 micron can now be made cost-effectively and commercially. One good example is the design and fabrication of micro electro mechanical devices (MEMS), which now are being used in a wide variety of applications in the integrated circuit industry.

Set forth below are several illustrations or examples of apparatus of this invention containing a class of innovative micro-devices that are integrated into the disease detection apparatus of this invention, and of their fabrication process.

FIG. 1 is a perspective illustration of a disease detection apparatus of this invention 111 in which a biological sample 211 such as a blood sample placed in it or moving through it is tested. In this figure, an example of disease detection apparatus 111 is in the form of a cylinder, in which a biological sample 211 flowing through it (from the left side to the right side in the figure) can be tested for one or more properties at the microscopic levels.

To enhance detection speed and sensitivity, a large number of micro-devices can be integrated into a single disease detection apparatus of this invention, such as the apparatus illustrated in FIG. 1(b) and FIG. 1(c) with the micro-devices spaced to measure a large number of desired entities (such as cells, DNAs, RNAs, proteins, etc.) in the biological sample. To achieve the above requirements, the detection apparatus should be optimized with its surface area maximized to contact the biological sample and with large number of micro-devices integrated on the maximized surface.

FIG. 2(a) is a perspective, cross-sectional illustration of a disease detection apparatus of this invention 122 with multiple identical micro-devices 311. A biological sample such as a blood sample 211 placed in it or moving through it can be tested for one or more properties at the microscopic levels including, e.g., electrical properties (such as surface charge, surface potential, current, impedance, other electrical properties), magnetic properties, electromagnetic properties, mechanical properties (such as density, hardness, shear strength, elongation strength, fracture tress, and adhesion), biological features, chemical properties (e.g., pH or ionic strength), biochemical properties, thermal properties (e.g., temperature), and optical properties.

Figure 3:
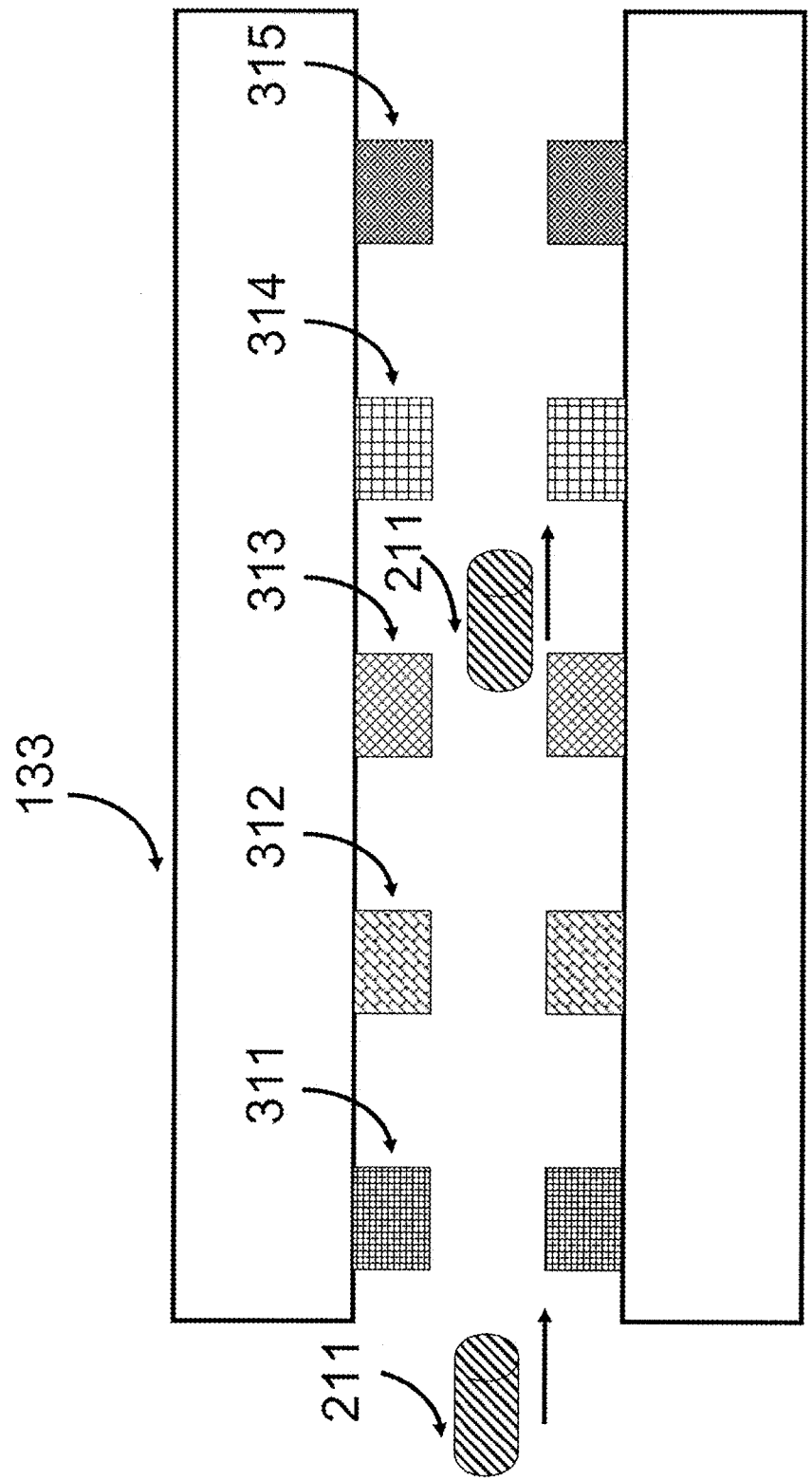
FIG. 3 is a perspective, cross-sectional illustration of a disease detection apparatus of this invention with multiple micro-devices of different detection probes. A biological sample is placed in the apparatus or moving through it and one or more microscopic properties of this sample are measured with the multiple micro-device.

Instead of measuring a single property of a biological subject for disease diagnosis, various micro-devices can be integrated into a detection apparatus to detect multiple properties. FIG. 3 is a perspective, cross-sectional illustration of a disease detection apparatus of this invention 133 with multiple micro-devices 311, 312, 313, 314, and 315, of different detection probes in which a sample 211 such as a blood sample placed in it or moving through it can be tested for multiple properties including but not limited to electrical properties (e.g., surface charge, surface potential, and impedance), magnetic properties, electromagnetic properties, mechanical properties (e.g., density, hardness and adhesion), thermal properties (e.g., temperature), biological properties, chemical properties (e.g., pH), physical properties, acoustical properties, and optical properties.

FIGS. 2(b)-2(n) illustrate a process flow of this invention for fabricating micro-devices for trapping, sorting, probing, measuring, and modifying biological subjects (e.g., a single cell, a DNA or RNA molecule). First, a material 2002 (e.g., a non-conducting material) and another material 2003 (e.g., a conducting material) are sequentially deposited on a substrate 2001 (see FIG. 2(b) and FIG. 2(c)). The first material 2003 is then subsequently patterned by the lithography and etch processes (see FIG. 2(d)). Another material 2004 is then deposited (as shown in FIG. 2(e)) and planarized (as shown in FIG. 2(f)). Another layer of material 2005 is deposited (as shown in FIG. 2(g)) and patterned as a hard mask (as shown in FIG. 2(h)), then followed by etch (as shown in FIG. 2(j)), which is stopped on the substrate 2001. FIG. 2(i) is a perspective illustration of the device, while FIG. 2(j) is a vertical illustration of the device.

As shown in FIG. 2(k), the device 2080 and a mirrored or symmetric device 2081 can be coupled together (as shown in FIG. 2(l)). As such, the apparatus having the pathway with probe embedded in the sidewall is fabricated.

As illustrated in FIG. 2(m) and FIG. 2(n), a large number of detection micro-devices can be integrated together to enhance the detection efficiency.

Figure 4:
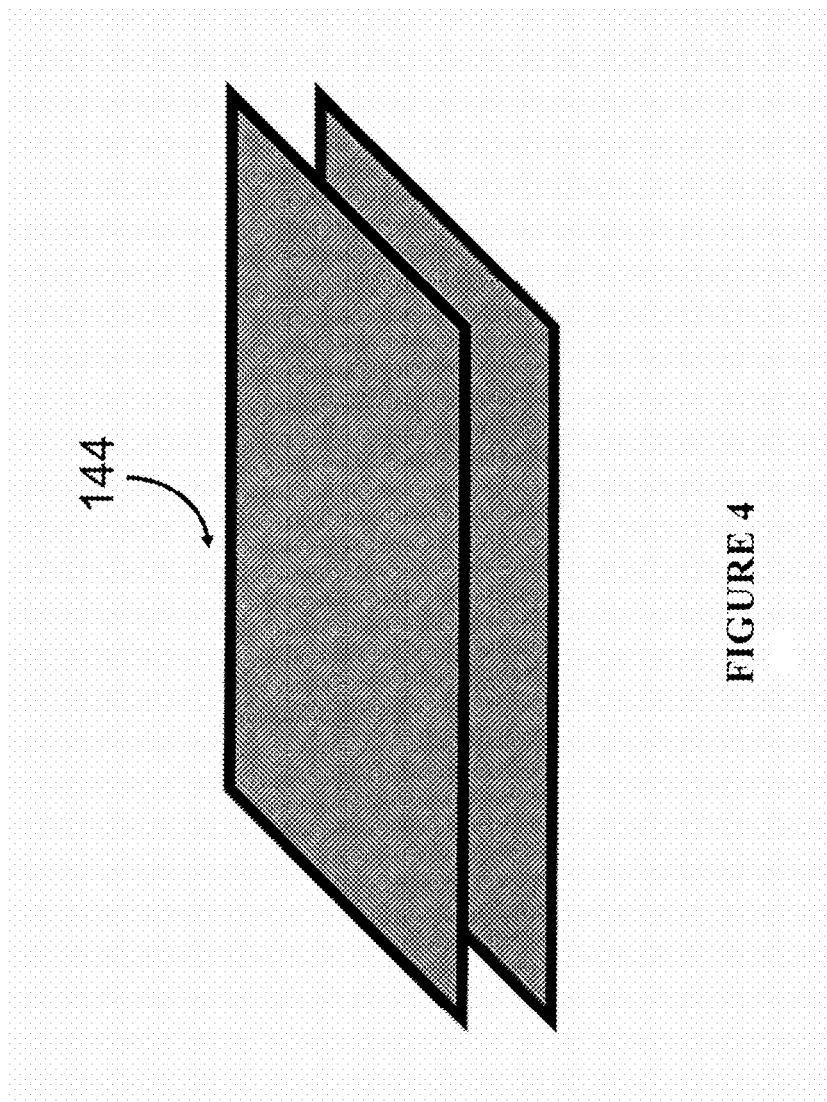
FIG. 4 is a perspective illustration of a disease detection apparatus of this invention. It includes two slabs separated by a narrow spacing with a biological sample to be analyzed placed between the slabs, with multiple micro-devices placed at the inner surfaces of the slabs to measure one or more desired parameters of the sample at microscopic levels.

As illustrated herein, it is desirable to optimize the detection apparatus design to maximize measurement surface area, since the greater the surface area, the greater number of micro-devices that can be placed on the detection apparatus to simultaneously measure the sample, thereby increasing detection speed and also minimizing the amount of sample needed for the test. FIG. 4 is a perspective illustration of a disease detection apparatus of this invention 144. It includes two slabs separated by a narrow spacing with a sample such as a blood sample to be measured placed between the slabs, with multiple micro-devices placed at the inner surfaces of the slabs to measure one or more properties of the sample at microscopic levels.

Figure 5:
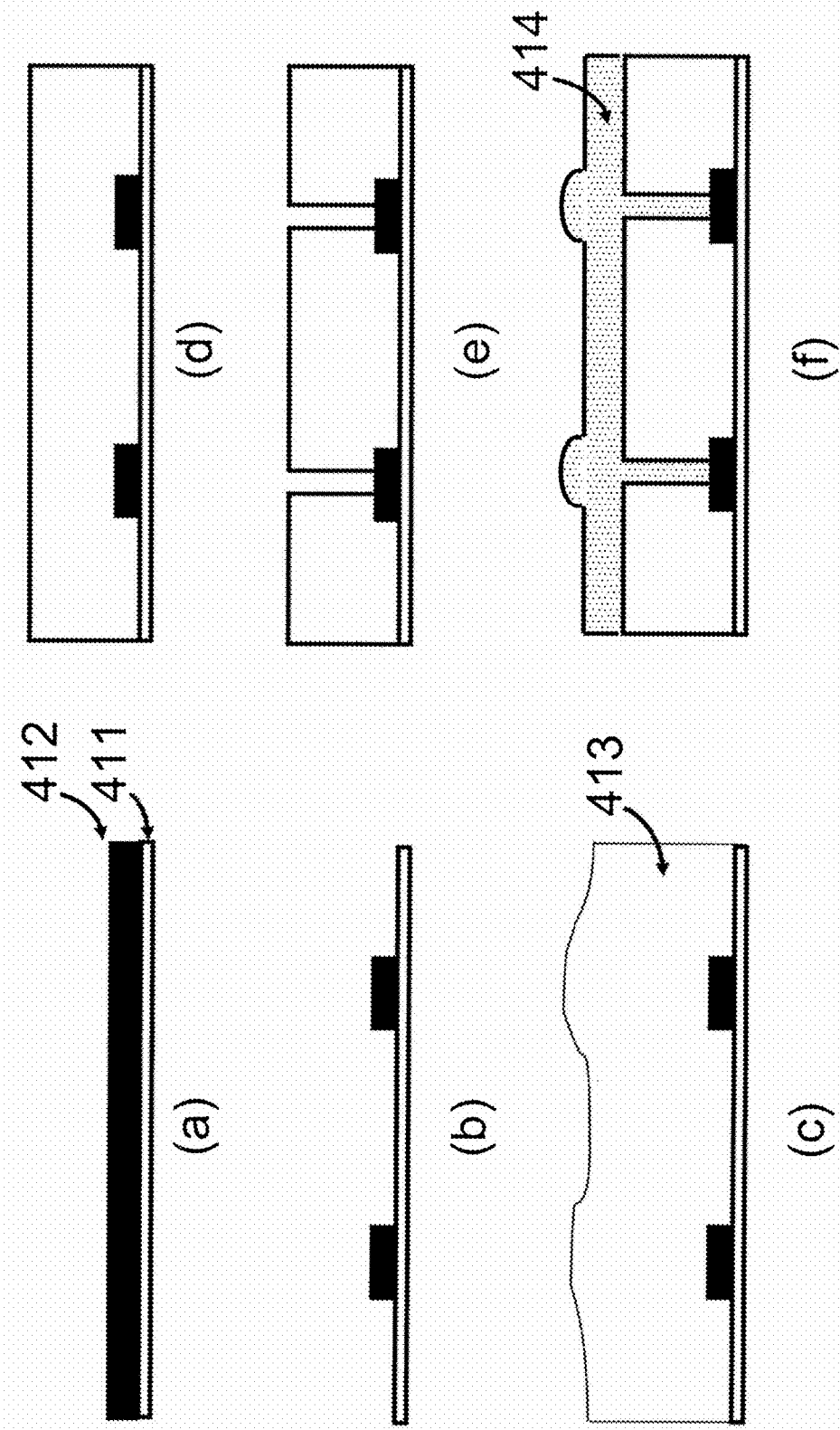
FIG. 5 illustrates a novel process flow for fabricating a disease detection apparatus of this invention utilizing microelectronics technologies.

Yet another aspect of this invention relates to a set of novel fabrication process flows for making micro-devices for disease detection purposes. FIG. 5 illustrates a novel process flow for fabricating a disease detection apparatus utilizing microelectronics technologies and processes. First, a material 412 is deposited on a substrate 411 (FIG. 5(a)). It is then patterned by photolithography and etching processes (FIG. 5(b)). Following the deposition, material 413 is planarized using chemical mechanical polishing as shown in FIG. 5(d). Recessed areas, in the form of hole pattern, are next formed in material 413 using photolithography and etch processes, as shown in FIG. 5(e), followed by the deposition of material 414 (FIG. 5(f)). Material 414 above the surface of material 413 is removed by chemical mechanical polishing (FIG. 5(g), followed by deposition of material 415. Material 415 is next patterned using photolithography and etching processes (FIG. 5(i)). Material 414 is next deposited and its excess material above its substrate 415 is removed by chemical mechanical polishing (FIGS. 5(j) and (k)). Finally, a light etch or short chemical mechanical polishing to material 415 is carried out to recess material 415, selective to material 414 (FIG. 5(l)), resulting in slight protruding of material 414. Material 412 can be a piezoelectric material. When a voltage is applied to it in the right direction, it will expand and push up, resulting in upward motion in middle tip in material 414. Thus, a micro-device with two probes capable of measuring a range of properties (including mechanical and electrical properties) of biological samples is fabricated, using the above novel fabrication process flow.

Figure 6:
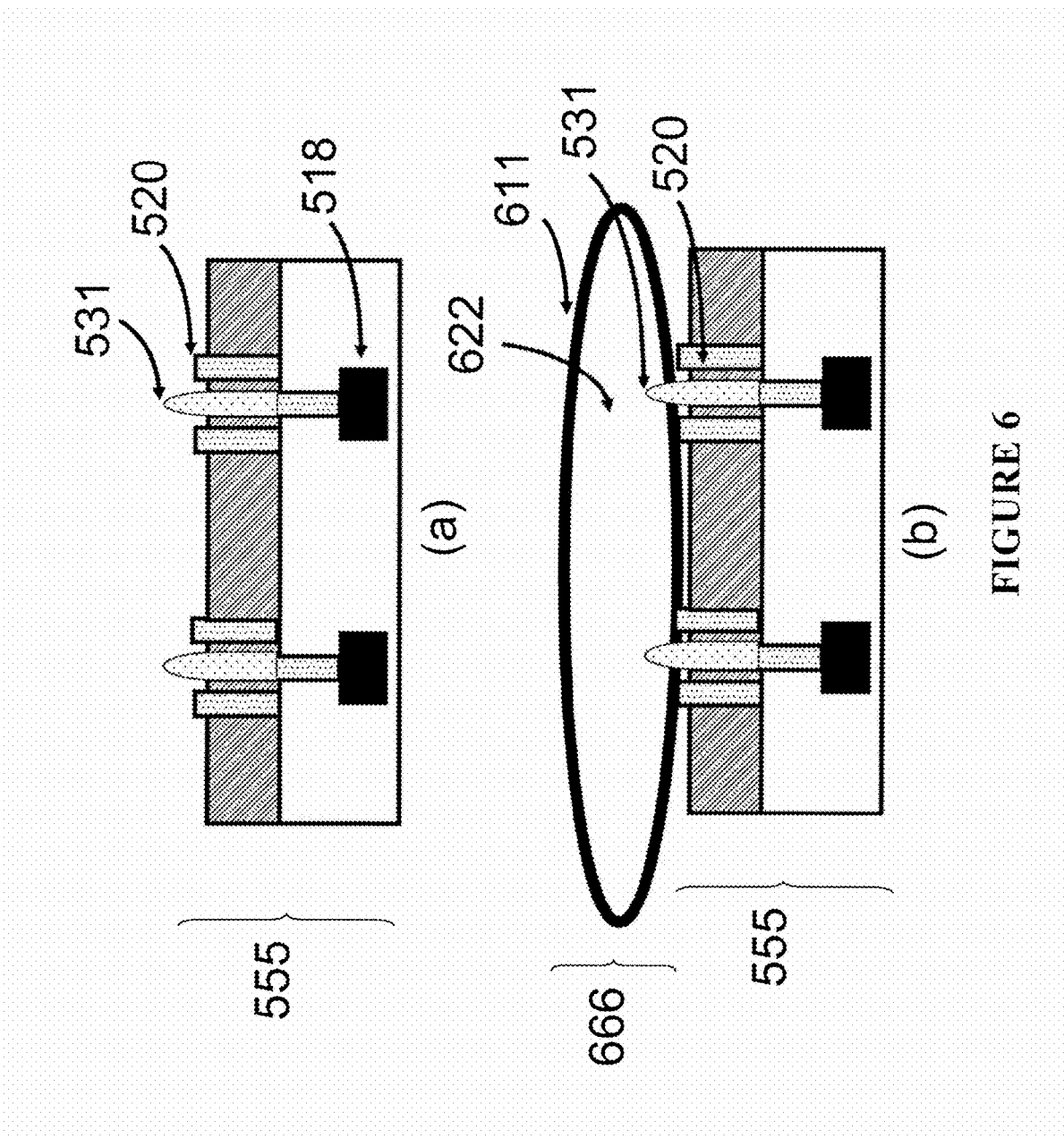
FIG. 6 is a perspective illustration of a disease detection apparatus fabricated by a method of this invention. The apparatus is capable of probing a single cell and measuring its microscopic properties.

Detection apparatus integrated with micro-devices disclosed in this application is fully capable of detecting pre-chosen properties on a single cell, a single DNA, a single RNA, or an individual, small sized biological matter level. FIG. 6 is a perspective illustration of a micro-device 555 fabricated by a novel process flow disclosed in this patent application (e.g., novel process flow illustrated in FIG. 5 above) and how such a device is capable of probing a single cell 666 and measuring the cell for collecting intended parameters. FIG. 6(a) illustrated a perspective, cross-section of a micro-device 555 with a pair of micro probes 531 and 520, where micro probe 531 is in the form of a tip and micro probe 520 is in the form of a ring. Both of micro probes 531 and 520 can be conductive and they can serve as a pair of probes to measure electrical properties of a biological sample. Micro probe 531 is in contact with a base 518 which can be a piezoelectric material. When a voltage is applied to the base 518 made of a piezoelectric material, the base 518 can expand and push micro probe tip 531 upward, which can be useful in measuring various properties of a biological sample such as a single cell. In FIG. 6(b), micro-device 555 is shown to measure a single cell 666, using probe tip 531 penetrating through cell membrane 611 and into the cell's inner space 622, while probe ring 520 making contact with cell membrane 611 at the outside surface of the membrane. This way, the micro-device 555 can make various measurements on the cell, including its electrical properties (e.g., electrical potential, current across the cell membrane, surface charge on the membrane, and impedance), mechanical properties (e.g., hardness when probe tip 531 is designed as a micro-indentation probe), thermal properties (e.g., temperature), physical properties, and chemical properties (e.g., pH).

In another further aspect, the invention provides the design, integration, and fabrication process flow of micro-devices capable of making highly sensitive and advanced measurements on very weak signals in biological systems for disease detection under complicated environment with very weak signal and relatively high noise background. Those novel capabilities using the class of micro-devices disclosed in this invention for disease detection include but not limited to making dynamic measurements, real time measurements (such as time of flight measurements, and combination of using probe signal and detecting response signal), phase lock-in technique to reduce background noise, and 4-point probe techniques to measure very weak signals, and unique and novel probes to measure various electronic, electromagnetic and magnetic properties of biological samples at the single cell (e.g., a telomere of DNA or chromosome), single molecule (e.g., DNA, RNA, or protein), single biological subject (e.g., virus) level.

For example, in a time of flight approach to obtain dynamic information on the biological sample (e.g., a cell, a substructure of a cell, a DNA, a RNA, or a virus), a first micro-device is first used to send a signal to perturb the biological subject to be diagnosed, and then a second micro-device is employed to accurately measure the response from the biological subject. In one embodiment, the first micro-device and the second micro-device are positioned with a desired or pre-determined distance L apart, with a biological subject to be measured flowing from the first micro-device towards the second micro-device. When the biological subject passes the first micro-device, the first micro-device sends a signal to the passing biological subject, and then the second micro-device detects the response or retention of the perturbation signal on the biological subject. From the distance between the two micro-devices, time interval, the nature of perturbation by the first micro-device, and measured changes on the biological subject during the time of flight, microscopic and dynamic properties of the biological subject can be obtained. In another embodiment, a first micro-device is used to probe the biological subject by applying a signal (e.g., an electronic charge) and the response from the biological subject is detected by a second micro-device as a function of time.

Figure 7:
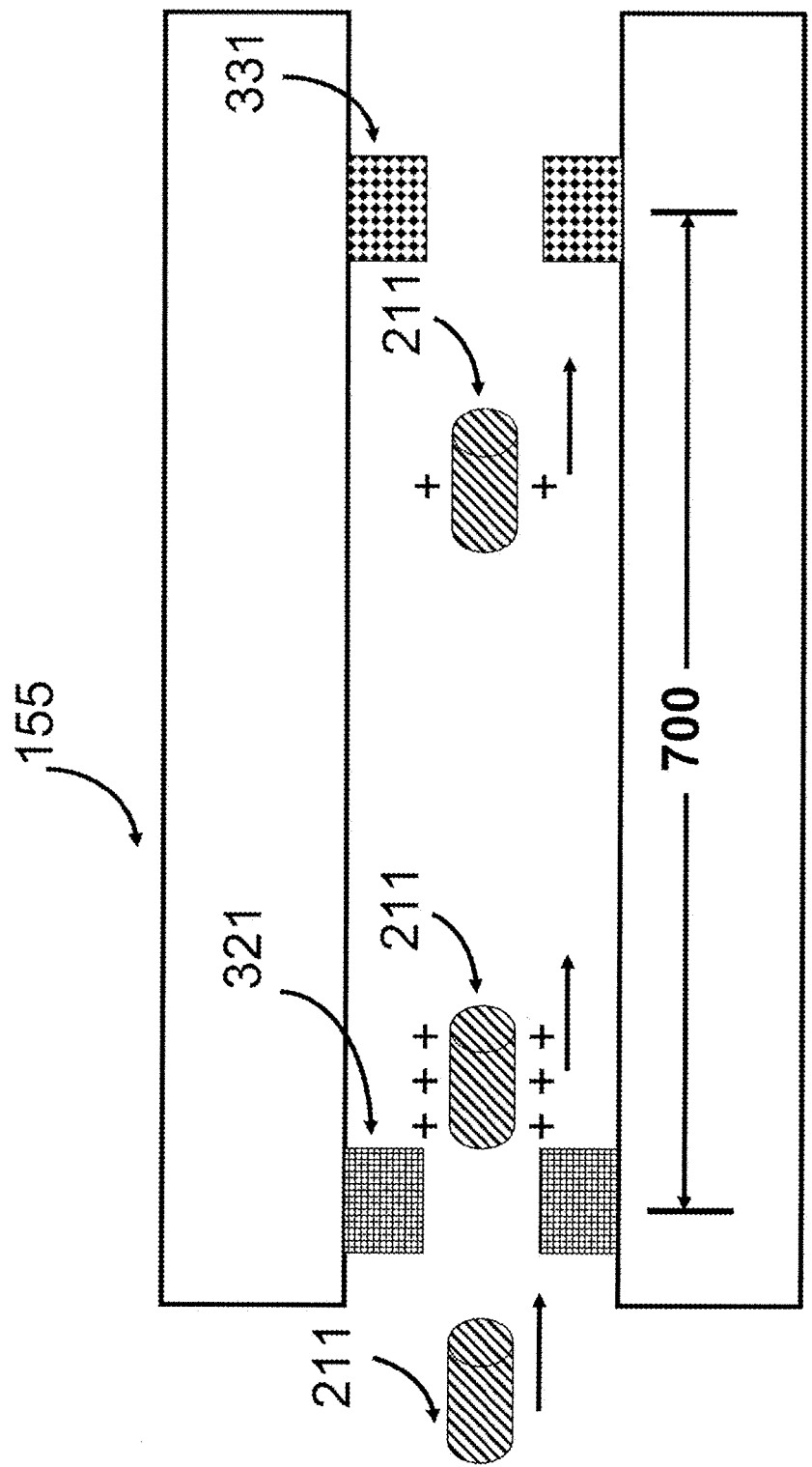
FIG. 7 is a perspective, cross-sectional illustration of a disease detection apparatus of this invention with multiple micro-devices placed at a desired distance for time of flight measurements with enhanced sensitivity, specificity, and speed, including time dependent or dynamic information.

To further increase detection sensitivity, a novel detection process for disease detection is used, in which time of flight technique is employed. FIG. 7 is a perspective, cross-sectional illustration of detection apparatus 155 with multiple micro-devices 321 and 331 placed at a desired distance 700 for time of flight measurements to attain dynamic information on biological sample 211 (e.g., a cell) with enhanced measurement sensitivity, specificity, and speed. In this time of flight measurement, one or more properties of the biological sample 211 are first measured when the sample 211 passes the first micro-device 321. The same properties are then measured again when the sample 211 passes the second micro-device 331 after it has travelled the distance 700. The change in properties of sample 211 from at micro-device 321 to at micro-device 331 indicates how it reacts with its surrounding environment (e.g., a particular biological environment) during that period. It may also reveal information and provide insight on how its properties evolve with time. Alternatively, in the arrangement shown in FIG. 7, micro-device 321 could be used first as a probe to apply a probe signal (e.g., an electrical charge) to sample 211 as the sample passes the micro-device 321. Subsequently, the response of the sample to the probe signal can be detected by micro-device 331 as the sample passes it (e.g., change in the electrical charge on the sample during the flight). Measurements on biological sample 211 can be done via contact or non-contact measurements. In one embodiment, an array of micro-devices can be deployed at a desired spacing to measure properties of the biological subject over time.

The utilization of micro-devices (e.g., made by using the fabrication process flows of this invention) as discussed above and illustrated in FIG. 7 can be helpful for detecting a set of new, microscopic properties of a biological sample (e.g., a cell, a cell substructure, or a biological molecule such as DNA or RNA or protein) that have not been considered in existing detection technologies. Such microscopic properties can be electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electrochemical, bio-electro-chemical-mechanical, physical, or mechanical properties of a biological sample that is a single biological subject (such as a cell, a cell substructure, a biological molecule—e.g., DNA, RNA, or protein—or a sample of a tissue or organ). It is known that biological matters includes from basic bonding such as OH, CO, and CH bonding, to complex, three dimensional structures such as DNA and RNA. Some of them have a unique signature in terms of its electronic configuration. Some of them may have unique electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electrochemical, bio-electro-chemical-mechanical, physical, or mechanical properties and configurations. Normal biological subject and diseased biological subject may carry different signatures with respective to the above said properties. However, none of the above stated parameters or properties have been routinely used as a disease detection property. Using a disease detection apparatus including one or more micro-devices of this invention, those properties can be detected, measured, and utilized as useful signals for disease detection, particularly for early stage detection of serious diseases such as cancer.

Figure 8:
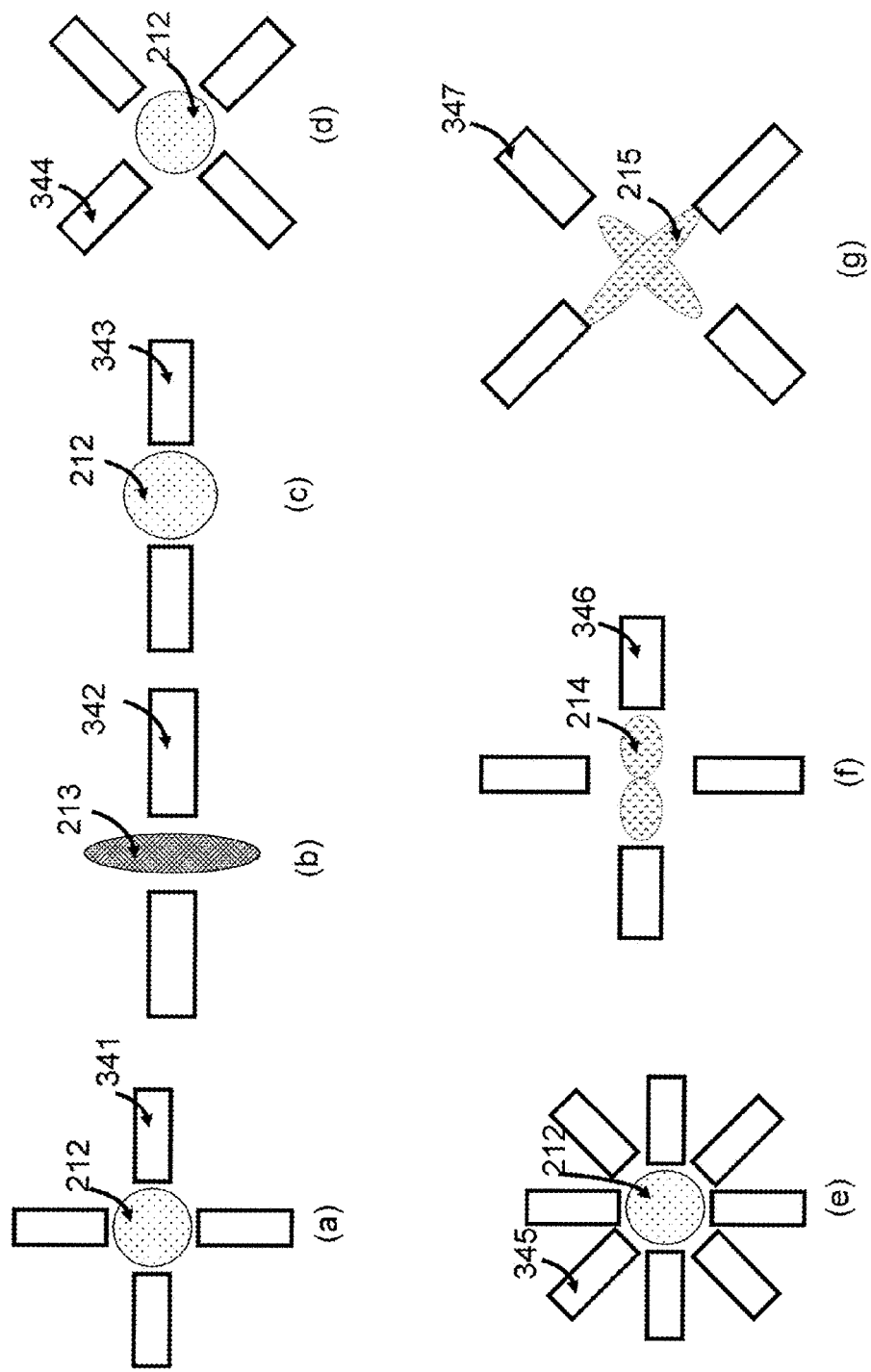
FIG. 8 is a perspective illustration of a novel set of microscopic probes, included in a disease detection apparatus of this invention, for detecting various electronic or magnetic states, configurations, or other properties of a biological sample (e.g., a cell, a DNA or RNA molecule, a telomere of DNA or chromosome, a virus, or a tissue sample).

FIG. 8 is a perspective illustration of a novel set of microscopic probes 341, 342, 343, 344, 345, 346, and 347 designed and configured to detect various electronic, magnetic, or electromagnetic states, configurations, or other properties at microscopic level on biological samples 212, 213, 214, and 215, which can be a single cell, DNA, RNA, and tissue or sample. As an example, in terms of measuring electronic properties, the shapes of biological samples 212, 213, 214, and 215 in FIG. 8 may represent electronic monopole (sample 212), dipole (samples 213 and 214), and quadruple (sample 215). The micro-devices 341, 342, 343, 344, 345, 346, and 347 are optimized to maximize measurement sensitivity of those said parameters including but not limited to electronic states, electronic charge, electronic cloud distribution, electrical field, and magnetic and electromagnetic properties, and the micro-devices can be designed and arranged in three dimensional configurations. For some diseases such as cancer, it is likely that electronic states and corresponding electronic properties differ between normal and cancerous cells, DNA, RNA, and tissue. Therefore, by measuring electronic, magnetic and electromagnetic properties at microscopic levels including at cell, DNA, and RNA levels, disease detection sensitivity and specificity can be improved.

In addition to the above examples in measuring electrical properties (e.g., charge, electronic states, electronic charge, electronic cloud distribution, electrical field, current, and electrical potential, and impedance), mechanical properties (e.g., hardness, density, shear strength, and fracture strength) and chemical properties (e.g., pH) in a single cell, and in FIG. 8 for measuring electrical, magnetic or electromagnetic states or configurations of biological samples at cell and biological molecular (e.g., DNA, RNA, and protein) levels, other micro-devices are disclosed in this application for sensitive electrical measurements.

Figure 9:
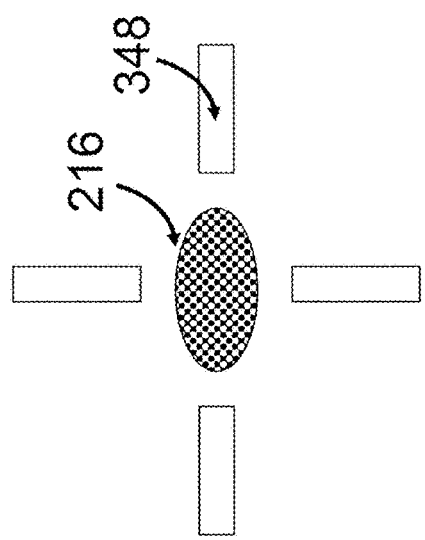
FIG. 9 is a perspective illustration of a novel four-point probe, included in a disease detection apparatus of this invention, for detecting weak electronic signal in a biological sample (e.g., a cell, a DNA or RNA molecule, a telomere of DNA or chromosome, a virus, or a tissue sample).

FIG. 9 is a perspective illustration of a four-point probe for detecting weak electronic signal in a biological sample such as a cell, where a four point probe 348 is designed to measure electrical properties (impedance and weak electrical current) of a biological sample 216.

One of the key aspects of this invention is the design and fabrication process flows of micro-devices and methods of use the micro-devices for catching and/or measuring biological subjects (e.g., cells, cell substructures, DNA, and RNA) at microscopic levels and in three dimensional space, in which the micro-devices have micro-probes arranged in three dimensional manner with feature sizes as small as a cell, DNA, or RNA, and capable of trapping, sorting, probing, measuring, and modifying biological subjects. Such micro-devices can be fabricated using state-of-the-art microelectronics processing techniques such as those used in fabricating integrated circuits. Using thin film deposition technologies such as molecular epitaxy beam (MEB) and atomic layer deposition (ALD), film thickness as thin as a few monolayers can be achieved (e.g., 4 A to 10 A). Further, using electron beam or x-ray lithography, device feature size on the order of nanometers can be obtained, making microdevice capable of trapping, probing, measuring, and modifying a biological subject (e.g., a single cell, a single DNA or RNA molecule) possible.

Figure 10:
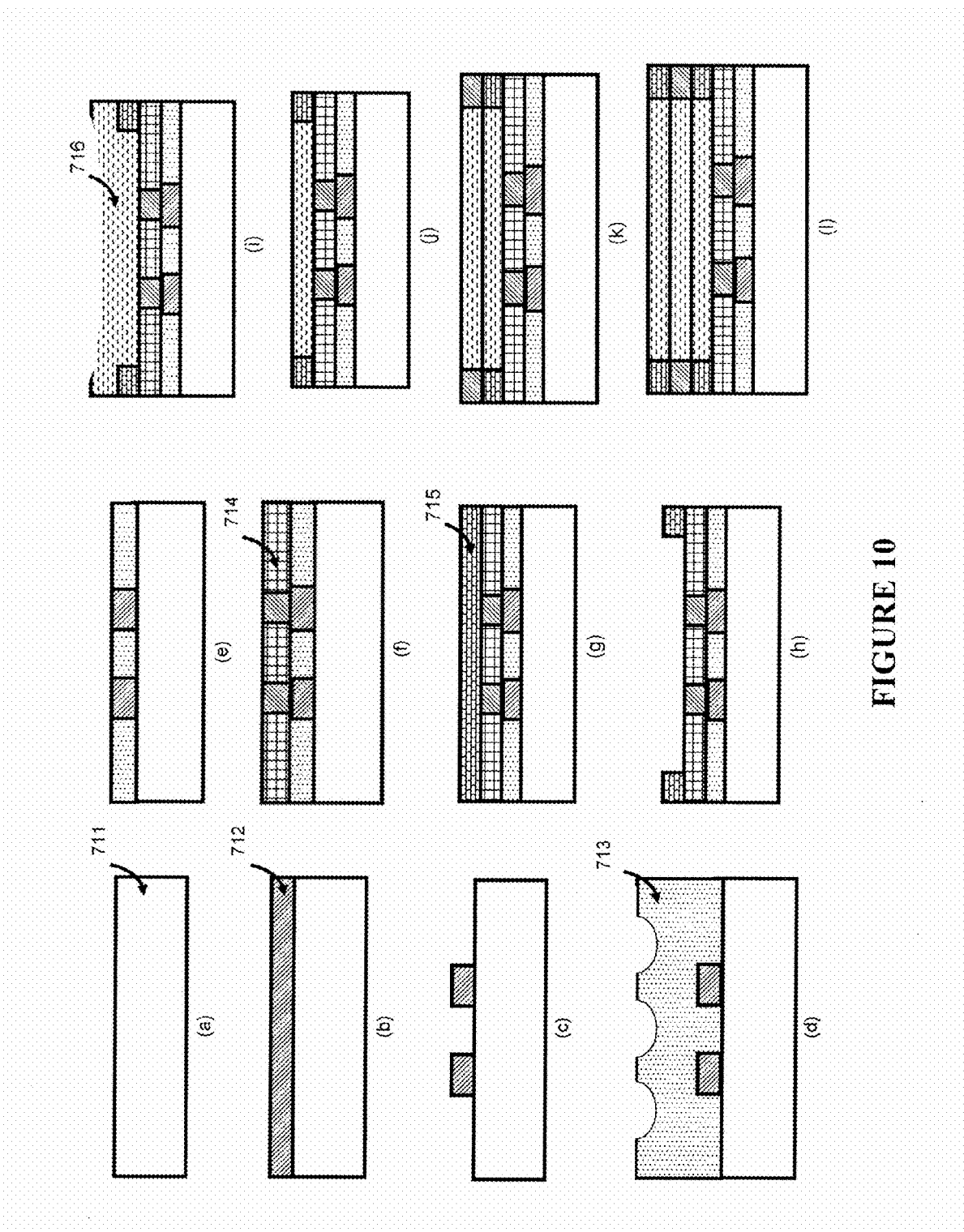
FIG. 10 illustrates a novel process flow for fabricating a class of micro-devices capable of trapping, sorting, probing, measuring, and modifying a biological subject (e.g., a cell, a DNA or RNA molecule, a telomere of DNA or chromosome, a virus, or a tissue sample) at the microscopic level and in a three-dimensional space.
Figure 10:
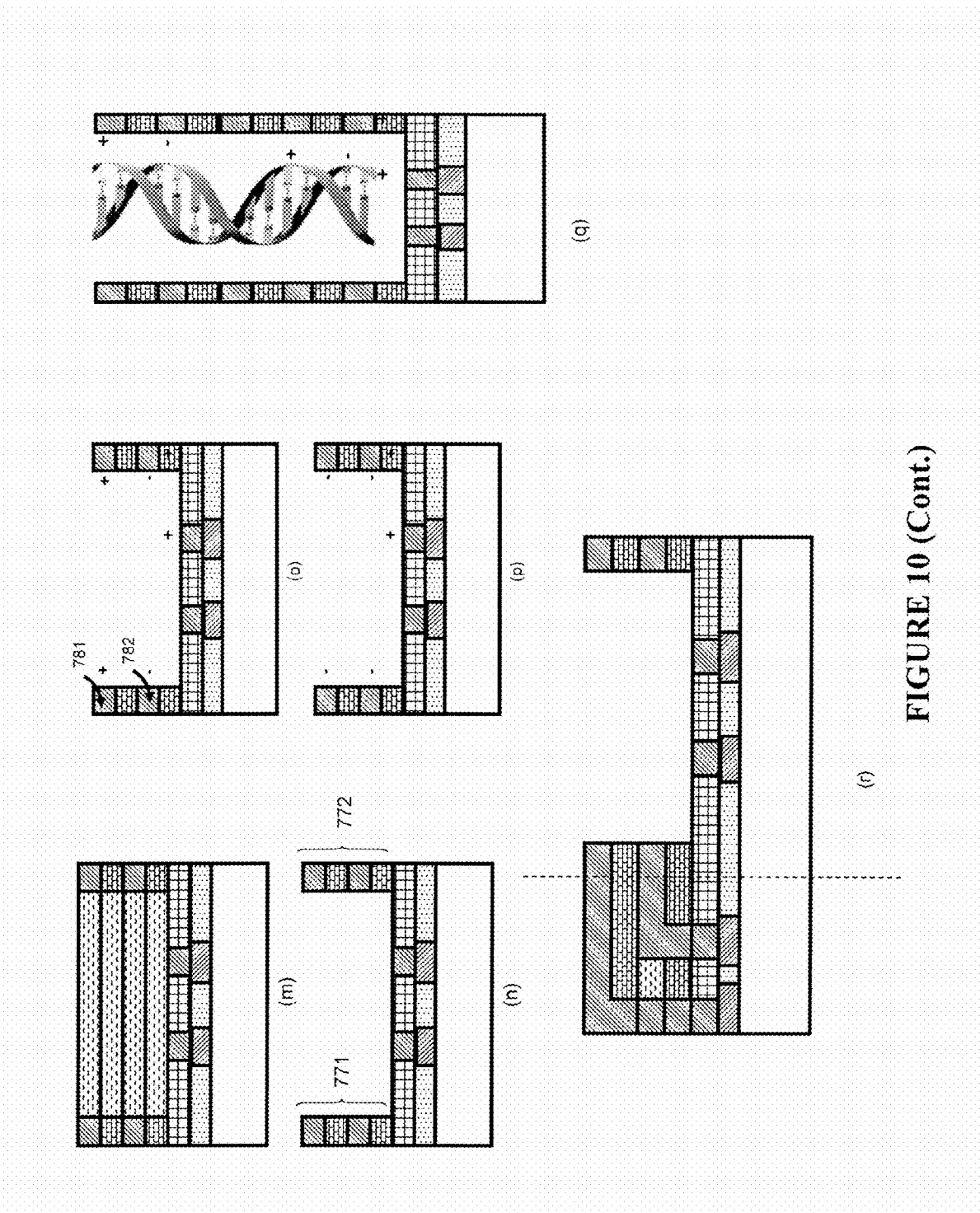

FIG. 10 illustrates a process flow of this invention for fabricating micro-devices for trapping, sorting, probing, measuring, and modifying biological subjects (e.g., a single cell, a DNA or RNA molecule). In this process flow, microelectronics processes are utilized to fabricate microdevices designed to achieve the above stated unique functions. Specifically, a first material 712 (typically a conducting material) is first deposited on a substrate 711 (FIG. 10(*a*) and FIG. 10(*b*)). The first material 712 is subsequently patterned by using lithography and etch processes (FIG. 10(*c*)). A second material 713 is then deposited and planarized using chemical mechanical polishing process to remove overburden of the second material 713 above the first material 712 (as shown in FIG. 10(*e*)). Another layer of material 714 is deposited and patterned, followed by deposition and planarization by chemical mechanical polishing of another layer of 712 (FIG. 10(f)). Next, a third material 715 is deposited and patterned, using lithography and etch processes (FIG. 10(g) and FIG. 10(h)), followed by deposition and planarization of a fourth material 716, typically a sacrificial material (FIG. 10(i) and FIG. 10(j)). Repeating the process flow of deposition of patterning material 712 or material 715 alternatively, and deposition of material 716 and planarization by chemical mechanical polishing (FIG. 10(k)-(m)), a film stack featuring multiple layers with alternating material 712 (e.g., a conducting material) and material 715 (e.g., an insulating material) in at least portions of the device is formed. Finally, material 716 between film stacks 771 and 772 is removed by wet etch, dry etch (which may require lithography process), or vapor etch, selective to all other materials (FIG. 10(n)). As illustrated in FIG. 10(o), in the case of 712 being a conductive material connected to an electrical circuit or an electrical source (e.g., a charge source), each probe tip formed by 712 on the stack (e.g., 781 and 782) can have a charge or an electrical field at the surface (e.g., 781 and 782), which (each probe tip) can be selected to have a positive charge or a negative charge, or a positive electrical field or negative electrical field. Conversely, such probe tip can also sense various properties of biological subject being measured (e.g., electronic cloud, field, charge, or temperature when the probe tip is a thermal detector, or light emission when the probe tip is an optical sensor). Using electrical circuit or electrical source, various combinations of electrical charge distribution or electrical field can be placed on the micro-device, as shown in FIG. 10(o) and FIG. 10(p), which can be used to sort and trap various biological subjects such as a cell and a DNA molecule. For instance, a biological subject with a charge distribution inverse of that in FIG. 10(p) can be trapped by the micro-device shown in FIG. 10(p). An array of micro-devices with various charge distributions or electrical field distributions can trap their respective biological subjects in a high speed, which can serve as a sorting device. FIG. 10(q) illustrates the use of a micro-device capable of trapping a DNA or measuring various properties (e.g., electrical, thermal, or optical properties) of a DNA, with each probe tip matched up spatially with either a major groove or minor groove of a double helix DNA. FIG. 10(r) illustrates how the probe tips are connected to electrical circuit, where only electrical wiring is shown. It should be noted that the micro-device shown in this example can be integrated onto a single chip with one billion or more such micro-devices to trap and/or sort cells, DNAs, RNAs, proteins, and other biological subject in a high speed.

Another aspect of this invention relates to micro-indentation probes and micro-probes for measuring a range of physical properties (such as mechanical properties) of biological subjects. Examples of the mechanical properties include hardness, shear strength, elongation strength, fracture stress, and other properties related to cell membrane which is believed to be a critical component in disease diagnosis.

Figure 11:
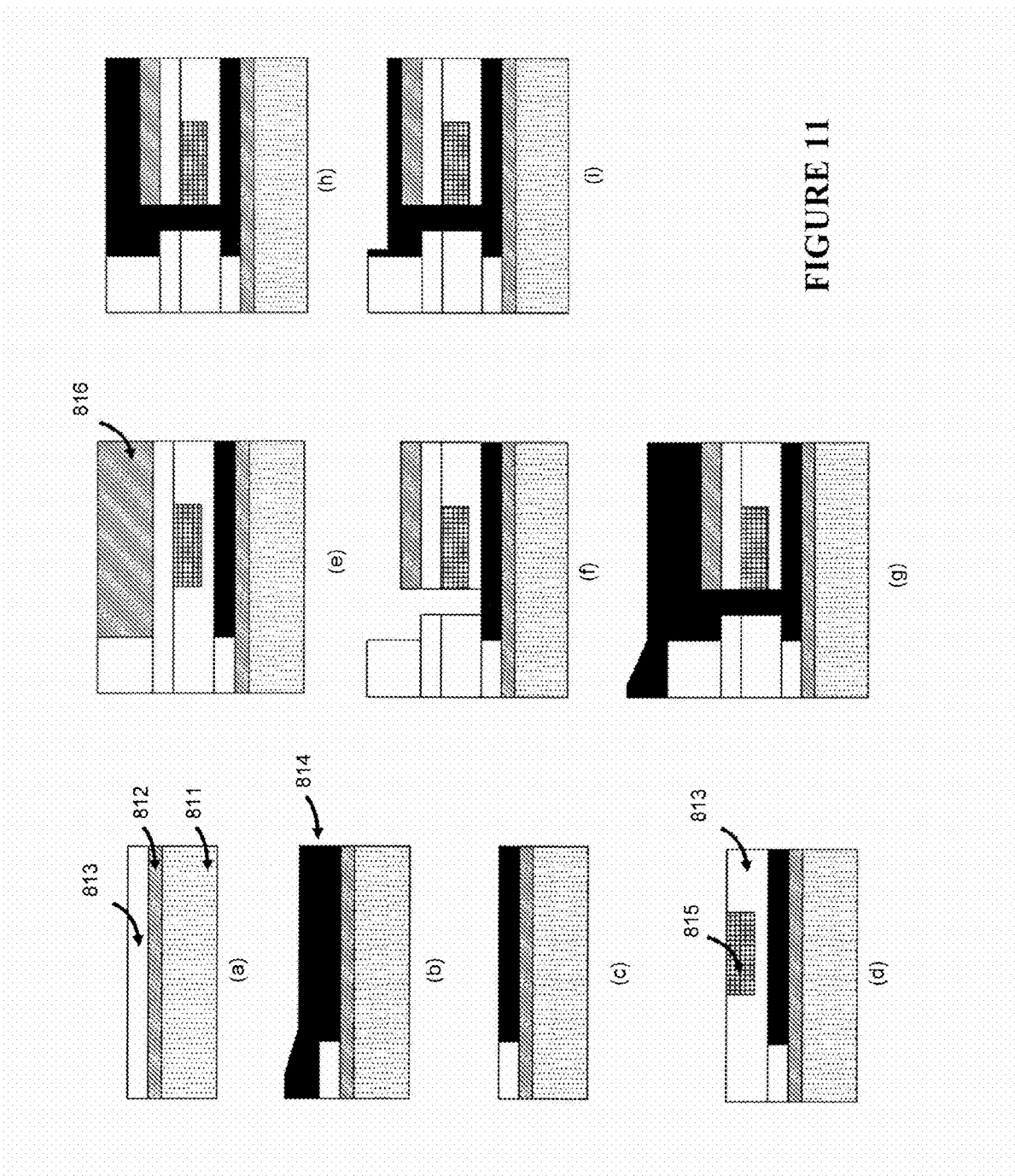
FIG. 11 illustrates a novel process flow for fabricating a class of micro-devices capable of measuring physical properties of a biological subject (e.g., a cell, a DNA or RNA molecule, a telomere of DNA or chromosome, a virus, or a tissue sample) such as mechanical properties (e.g., hardness, shear strength, elongation strength, fracture stress) and other properties related to cell membrane.
Figure 11:
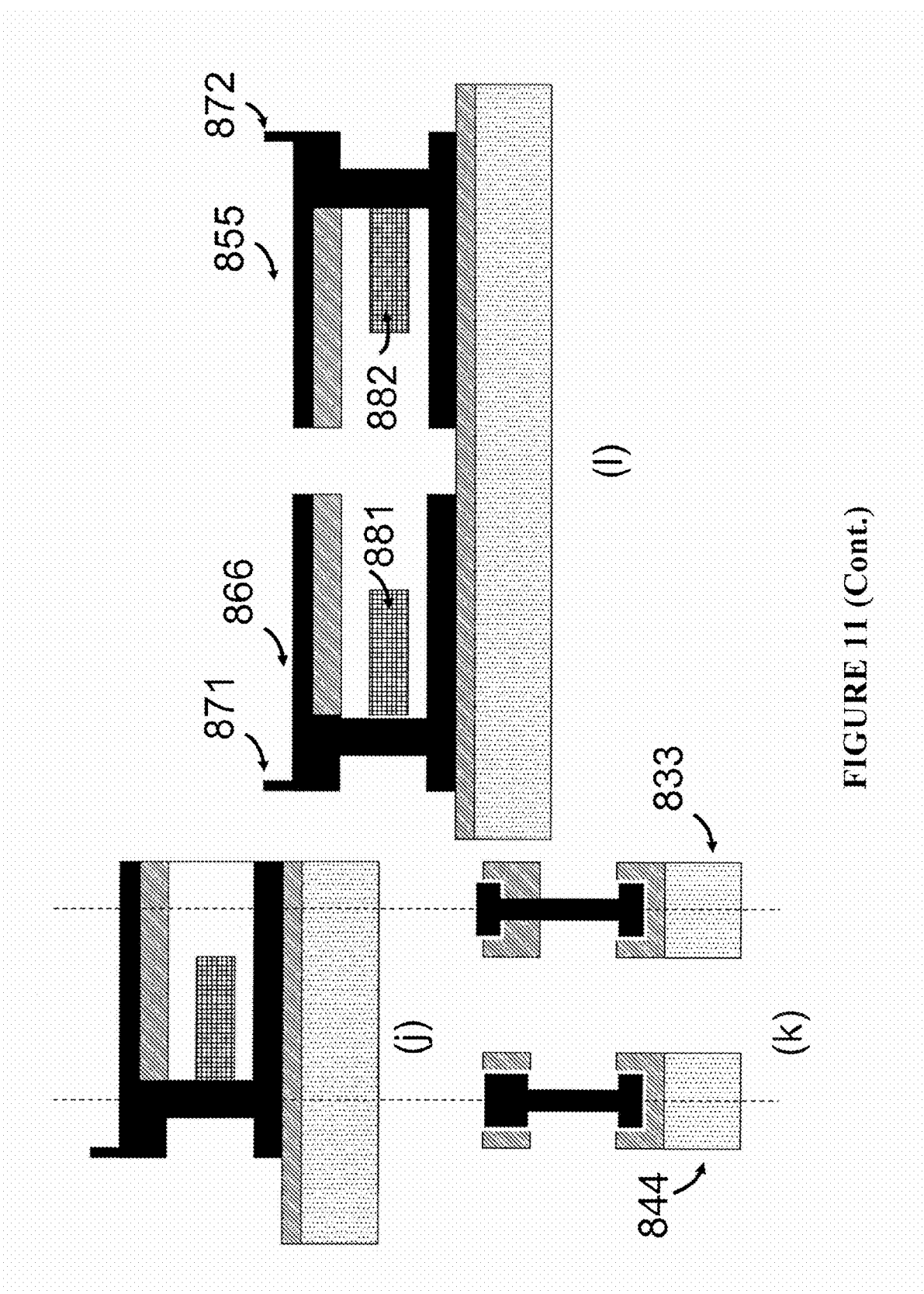

FIG. 11 illustrates a novel fabrication process flow for micro-devices capable of probing a range of properties of biological subjects, such as mechanical properties of cell membrane (e.g., mechanical strength of a cell membrane). In this process flow, a material 812 is first deposited onto a substrate 811, followed by the deposition of another material 813 (FIG. 11(a)). Following patterning of material 813 using lithography and etch processes, a material 814 is deposited (FIG. 11(b)) and planarized (FIG. 11(c)). Another layer of material 813 is next deposited and patterned using lithography and etch processes to remove portions of the material 813, followed by the deposition and planarization of a material 815 (which can be a piezoelectric material and can serve as a driver) (FIG. 11(d)). A layer of material 813 is next deposited, followed by deposition and patterning of yet another layer of 813, and deposition and planarization of material 816 (FIG. 11(e)). Next, material 816 is etched back to a reduced thickness, and patterned, followed by patterning of triple-layer of material 813 (FIG. 11(f)). Another layer of 814 is deposited (FIG. 11(g)) and planarized by chemical mechanical polishing (FIG. 11(h)), and patterned (FIG. 11(i)). Finally, multiple layers of 813 are removed by wet etch, plasma etch, or vapor etch (FIG. 11(j)). FIG. 11(k) is a perspective, cross-sectional illustration of the micro-device in a plane perpendicular to that in FIG. 11(j) (90-degree rotation from FIG. 11(j)). FIG. 11(l) illustrates a micro-device with two micro-tips 871 and 872 which can move in opposite directions when a voltage is applied to piezoelectric drivers 881 and 882, which can be used to probe biological subjects such as cells.

Figure 12:
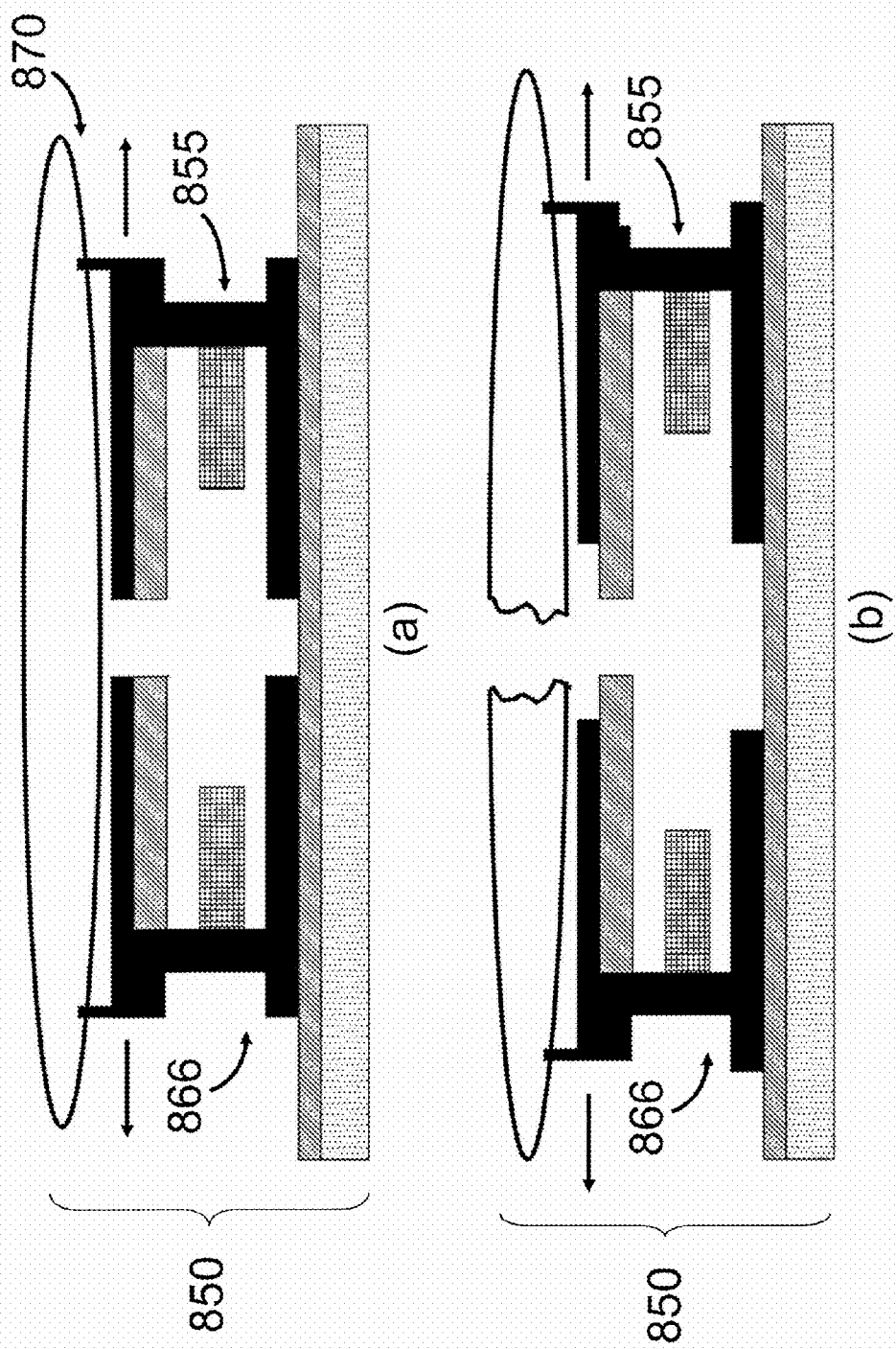
FIG. 12 illustrates how a micro-device with two micro-probes capable of moving in opposite directions when a force is applied can be utilized to probe properties of a biological subject (e.g., mechanical properties of a cell membrane).

FIG. 12 is an illustration of how micro-devices fabricated using the novel manufacturing process shown in FIG. 11 work. In FIG. 12, a micro-device 850 with two micro-probes 866 and 855 can move in opposite directions upon a force being applied (FIG. 12(a)). When the tips of the two probes are penetrated into a cell 870, as the distance between the two micro-probes is increased with the increasing applied force, the cell is stretched. Finally, as the applied force is reached a critical value, the cell is broken into two pieces (FIG. 12(b)). The dynamic response of the cell to the applied force provides information on the cell, particularly on the mechanical properties (e.g., elasticity) of cell membrane. The force at the point in which the cell is torn apart reflects the strength of the cell and it may be called a breaking point: the greater the mechanical strength of the cell membrane is, the greater the force is at the breaking point.

Another novel approach provided by this invention is the use of phase lock-in measurement for disease detection, which reduces background noise and effectively enhances signal to noise ratio. Generally, in this measurement approach, a periodic signal is used to probe the biological sample and response coherent to the frequency of this periodic probe signal is detected and amplified, while other signals not coherent to the frequency of the probe signal is filtered out, which thereby effectively reduces background noise. In one of the embodiments in this invention, a probing micro-device can send a periodic probe signal (e.g., a pulsed laser team, a pulsed thermal wave, or an alternating electrical field) to a biological subject, response to the probe signal by the biological subject can be detected by a detecting micro-device. The phase lock-in technique can be used to filter out unwanted noise and enhance the response signal which is synchronized to the frequency of the probe signal. The following two examples illustrate the novel features of time of flight detection arrangement in combination with phase lock-in detection technique to enhance weak signal and therefore detection sensitivity in disease detection measurements.

FIG. 13 is an illustration of a novel time of flight detection arrangement for disease detection applications. Specifically, FIG. 13(a) shows a set-up for measuring biological subject 911 using detection probe 933 and clock generator 922, and FIG. 13(b) contains recorded signal 921 due to structure 922, signal 931 recorded by signal probe 933, and processed signal 941 using a phase lock-in technique to filter out noise in recorded signal 931, where only response synchronized to clock signal 921 is retained. In the setup shown in FIG. 13(a), when a biological subject such as a cell 911 passes a structure 922, it triggers a clear signal (e.g., a light scattering signal if 922 is a light source, or a sharp increase in voltage if 922 is an orifice structure in a resistor). Therefore, 922 can be used to register the arrival of the biological subject, and as a clock when multiple structures of 922 are placed at a periodic distance as shown in recorded signal trace 921 in FIG. 13(*b*). In addition, when 922 is placed at a known distance in front of a probe 933, it marks the arrival of a biological subject coming towards 933 and signal response recorded at 933 is delayed by a time t from the signal triggered by 922 where t equals distance between 922 and 933 divided by traveling speed of the biological subject. As illustrated in FIG. 13(*b*), signal 921 due to structure 922 is clear and periodic with periodicity proportional to distance between structure 922*s*, while signal measured by probe 933 has a high noise level and relatively weak signal related to the biological subject. With the utilization of phase lock-in technique to filter out noise in recorded signal 931 by the detection probe 933 un-synchronized to clock signal 921, signal to noise ratio can be greatly enhanced as shown in processed signal 941 in FIG. 13(*b*).

FIG. 14 illustrates yet another time of flight disease detection arrangement in which a clock signal generator 922, a probe signal generator 944, and a signal detection probe 955 are used, along with schematically recorded clock signal 921, total recorded response signal 951 (except clock signal), and processed signal 952 using phase lock-in technique. In this arrangement, a probe signal generator 944 is used to perturb the biological subject 911 (e.g., heating 911 up using an optical beam, or adding an electrical charge to 911), and response to the probe signal is subsequently measured as a function of time using an array of detection probes 955. The filtered signal in 952 shows dynamic response to probe signal by 944 as it decays over time. Since normal cell and abnormal cell may respond differently to the probe signal, this arrangement with proper micro-probes can be utilized to detect diseases such as cancer. In another embodiment utilizing this set-up (shown in FIG. 14), the probe signal generator 944 can send a periodic signal to the biological subject 911, detected response signal from the biological subject by the detection probe 955 can be processed using the phase lock-in technique, with noise un-synchronized to the frequency of the probe signal filtered out and signal synchronized to the probe signal frequency amplified.

FIG. 15 is a perspective illustration of the novel multi-property micro-filter. A timed shutter 1502 is sandwiched between 2 pieces of filter membrane 1501 with wells. When a biological subject 1511 moves through the pathway of the well, it is first detected by the counter 1512, which triggers the clock of the barrier panel 1502. Then the larger cells will be filtered out, or blocked, by the filter's holes 1001, while only the specific subjects with enough speed are able to get through the pathway 1503 before the timed shutter 1502 closes the filter pathway (see FIG. 15(*b*)). Otherwise it will be held back as the timed shutter 1502 moves to block the pathway as shown in FIG. 15(*c*).

FIG. 16 illustrates a fluid delivery system that includes a pressure generator, a pressure regulator, a throttle valve, a pressure gauge, and distributing kits. The pressure generator 1605 sustains fluid with desired pressure, and the pressure is further regulated by the regulator 1601 and then accurately manipulated by the throttle valve 1602. Meanwhile, the pressure is monitored at real time and fed back to the throttle valve 1602 by the pressure gauge 1603. The regulated fluid is then in parallel conducted into the multiple devices where a constant pressure is needed to drive the fluid sample.

FIG. 17 illustrates how a micro-device in a disease detection apparatus of this invention can communicate, probe, detect, and optionally treat and modify biological subjects at a microscopic level. FIG. 17(*a*) illustrates the sequence of cellular events from signal recognition to cell fates determination. First, as the signals 1701 are detected by receptors 1702 on the cell surface, the cell will integrate and encode the signals into a biologically comprehensible message, such as calcium oscillation 1703. Consequently, corresponding proteins 1704 in the cell will interact with the message, then be modified and transform into ion-interacted proteins 1705 accordingly. Through the translocation, these modified proteins 1705 will pass the carried message to the nuclear proteins, and the controlled modification on nuclear proteins will modulate the expression of gene 1707 which includes transcription, translation, epigenetic processes, and chromatin modifications. Through messenger RNA 1709, the message is in turn passed to specific proteins 1710, thereby changing their concentration—which then determines or regulates a cell's decision or activities, such as differentiation, division, or even death.

FIG. 17(*b*) illustrates an apparatus of this invention which is capable of detecting, communicating with, treating, modifying, or probing a single cell, by a contact or non-contact means. The apparatus is equipped with micro-probes and micro-injectors which are addressed and modulated by the controlling circuitry 1720. Each individual micro-injector is supplied with a separate micro-cartridge, which carries designed chemicals or compounds.

To illustrate how an apparatus of this invention can be used to simulate an intracellular signal, calcium oscillation is taken as an example mechanism. First, a $Ca^{2+}$-release-activated channel (CRAC) has to be opened to its maximal extent, which could be achieved by various approaches. In an example of the applicable approaches, a biochemical material (e.g., thapsigargin) stored in the cartridge 1724 is released by an injector 1725 to the cell, and the CRAC will open at the stimulus of the biological subject. In another example of the applicable approaches, the injector 1724 forces a specific voltage on cell membrane, which causes the CRAC to open as well.

The $Ca^{2+}$ concentration of a solution in the injector 1728 can be regulated as it is a desirable combination of a $Ca^{2+}$-containing solution 1726, and a $Ca^{2+}$ free solution 1727. While the injector 1730 contains a $Ca^{2+}$ free solution, then injectors 1728 and 1730 are alternately switched on and off at a desired frequency. As such, the $Ca^{2+}$ oscillation is achieved and the content inside the cell membrane are then exposed to a $Ca^{2+}$ oscillation. Consequently, the cell's activities or fate is being manipulated by the regulated signal generated by the apparatus.

Meanwhile, the cell's response (e.g., in the form of an electric, magnetic, electromagnetic, thermal, optical, acoustical, or mechanical property) can be monitored and recorded by the probes integrated in this apparatus.

FIG. 17(*c*) illustrates another design of apparatus which is able to setup communication with a single cell. The apparatus is equipped with micro-probes which are coated with biologically compatible compounds or elements, e.g., Ca, C, Cl, Co, Cu, H, I, Fe, Mg, Mn, N, O, P, F, K, Na, S, or Zn. These probes can generate oscillating chemical signals with such an element or compound to interact with the cell, and results into a response that affects the cell's activities or eventual fate as describe above. Likewise, this apparatus can probe and record the cell's response (e.g., in the form of an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical property) as well.

FIG. 18 illustrates the system block diagram of a disease detection apparatus of this invention. This example includes a fluid delivering system 1801, biological interface 1802, a probing and detecting device 1803, a system controller 1805, a medical waste reclaiming and treating system 1804. A biological sample or material is transported to the interface 1802 by the fluid delivery system 1801, meanwhile the fluid parameters (or properties) are reported to the system controller 1805 which comprises a logic processing unit, a memory unit, an application specific chip, a sensor, a signal transmitter, and a signal receiver; and then the system controller 1805 can give further command to the system. The interface 1802 is an assembly which bridges a fluid sample and the detecting device, and further monitors the parameters or properties of the biological sample (e.g., pressure, temperature, stickiness, or flow rate) and then reports the date to the system controller 1805 while distributing the biological sample to the probing and detecting device 1803 with a specified speed or pressure (which can be commanded by the system controller 1805).

The system controller 1805 is the central commander and monitor of the entire system (or apparatus), where all the parameters and information from various modules is processed and exchanged and the instructions are given out, and where the command is dispatched. The system controller 1805 can include, e.g., a pre-amplifier, an electrical meter, a thermal meter, a switching matrix, a system bus, a nonvolatile storage device, a random access memory, a processor, and a user interface through which the user of the apparatus can manipulate, configure the apparatus, and read the operating parameters and final result. The pre-amplifier can process the raw signal to a recognizable signal for the meters. The meters can force and measure corresponding signals which can be, e.g., electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical signals, or combinations thereof. The switching matrix can switch the testing terminals of different arrays of the probe sub-apparatus. The user interface includes input and output assemblies and is an assembly which seals the fluid delivery system and the probing and detecting device together.

The probing and detecting device 1803 is the core functional module of the disease detection apparatus of this invention as it is the unit that probes the biological sample and collects related cellular signals (or responses). The waste reclaiming and treating system 1804 reclaims the waste biological sample to protect the privacy of its biological host, and keeps it away from polluting the environment.

FIGS. 19(b)-(l) illustrate a process flow for fabricating a micro-device for trapping, sorting, probing, measuring, treating, or modifying a biological subject (e.g., a single cell, a DNA or RNA molecule). A first material 1902 (e.g., a piezoelectric conducting material) and a second material 1903 (e.g., a conducting material) are sequentially deposited on a substrate 1901 (see FIGS. 19(b) and 19(c)). The second material 1903 is subsequently patterned by lithography and etch processes (see FIG. 19(d)). A third material 1904 is next deposited (as shown in FIG. 19(e)) and planarized (see FIG. 19(f)). A layer of a fourth material 1905 is subsequently deposited (see FIG. 19(g)) and patterned as a hard mask (see FIG. 19(h)), followed by etch to remove the third and first materials from desired areas, which stops on the substrate 1901. FIG. 19(i) is a perspective illustration of the device, while FIG. 19(j) is a vertical illustration of the same device.

FIG. 19 (k) illustrates the use of a micro-device capable of trapping a DNA 1920 and measuring various properties (e.g., electrical, magnetic, physical, thermal, chemical, biological, bio-chemical, or optical properties) of a DNA. Each probe tip 1912 matches up spatially with either a major groove or minor groove of a double helix DNA. Meanwhile, two probes (1911 and 1910) configured at the end of the trench can force or measure signals to each strand end of the DNA's double helix. The probes can be made of a conducting material with optionally a piezoelectric support structure, which can stretch forward and backward at a desired distance. All the probes are numbered, addressed, and controlled by a controlling circuitry.

FIG. 19(l) shows a simplified form of the device illustrated in FIG. 19(k). In this device, probe tips match spatially with interlaced grooves of a double helix DNA. The number of groove intervals between the adjacent probes is variable. If required, either DNA can be moved (for example, by pulling by probes 1910 and 1911) or the probes can move along the trench direction, mapping out properties in a full or partial DNA.

FIG. 20 illustrates an apparatus of this invention that is capable of detecting or measuring the surface charge of a biological subject 2010. It includes a channel, a pair of plates 2022, and a slit 2030 which separates the channel into a top channel 2041 and a bottom channel 2051. When a biological subject 2010 carrying a surface charge (positive charge shown in FIG. 20(a)) passes through the channel, under the influence of the voltage applied on the plates 2022 (with positive voltage at the top plate and negative at the bottom plate), it will move towards the bottom plate as shown in FIG. 20(b). Thus, the biological subject 2010 will pass through the bottom channel 2051 when it reaches slit 2030. (If the biological subject 2010 carries a negative charge, it would pass through the top channel 2041.) This way, a biological subject with unknown charge type (negative or positive) can be determined by using this apparatus.

This device comprises at least 2 parts of channel, one of which is channel 2060 where the biological subject is charged or modified, and the other comprises at least one plate or slit to separate the biological subjects (e.g., where the biological subjects are separated).

As surface charge will affect the shape of a biological subject, by using novel and multiple plates, information on the shape and charge distribution of biological subjects can be obtained. The general principle and design of the micro-device can be extended to a broader scope, thereby making it possible to obtain other information on the biological subject via separation by applying other parameters such as ion gradient, thermal gradient, optical beam, or another form of energy.

FIG. 21 illustrates another apparatus of this invention for detecting or measuring microscopic properties of a biological subject 2110 by utilizing a micro-device that includes a channel, a set of probes 2120, and a set of optical sensors 2132 (see, FIG. 21(a)). The detected signals by probes 2120 can be correlated to information including images collected by the optical sensors 2132 to enhance detection sensitivity and specificity. The optical sensors can be, e.g., a CCD camera, a florescence light detector, a CMOS imaging sensor, or any combination.

Alternatively, a probe 2120 can be designed to trigger optical emission such as florescence light emission 2143 in the targeted biological subject such as diseased cells, which can then be detected by an optical probe 2132 as illustrated in FIG. 21(*c*). Specifically, biological subjects can be first treated with a tag solution which can selectively react to diseased cells. Subsequently, upon reacting (contact or non-contact) with probe 2120, optical emissions from diseased cells occur and can be detected by optical sensors 2132. This novel process using the micro-devices of this invention is more sensitive than such conventional methods as traditional florescence spectroscopy as the emission trigger point is directly next to the optical probe and the triggered signal 2143 can be recorded in real time and on-site, with minimum loss of signal.

FIG. 22 illustrates another embodiment of the apparatus of this invention, which can be used to separate biological subjects of different geometric size and detect their properties respectively. It includes at least an entrance channel 2210, a disturbing fluid channel 2220, an accelerating chamber 2230, and two selecting channels 2240 and 2250. The angle between 2220 and 2210 is between 0° and 180°. The biological subject 2201 flows in the x-direction from 2210 to 2230. The biocompatible distribution fluid 2202 flows from 2220 to 2230. Then the fluid 2202 will accelerate 2201 in y-direction. However, the acceleration correlates with the radius of the biological subjects and the larger ones are less accelerated than the small ones. Thus, the larger and smaller subjects are separated into different channels. Meanwhile, probes can be optionally assembled aside the sidewall of 2210, 2220, 2230, 2240, and 2250. They could detect electric, magnetic, electromagnetic, thermal, optical, acoustical, biological, chemical, physical, or mechanical properties at the microscopic level.

The channel included in the apparatus of this invention can have a width of, e.g., from 1 nm to 1 mm. The apparatus should have at least one inlet channel and at least two outlet channels.

FIG. 23 shows another apparatus of this invention with an acoustic detector 2320 for measuring the acoustic property of a biological subject 2301. This apparatus includes a channel 2310, and at least an ultrasonic emitter and an ultrasonic receiver installed along the sidewall of the channel. When the biological subject 2301 passes through the channel 2310, the ultrasonic signal emitted from 2320 will be received after carrying information on 2301 by the receiver 2330. The frequency of the ultrasonic signal can be, e.g., from 2 MHz to 10 GHz, and the trench width of the channel can be, e.g., from 1 nm to 1 mm. The acoustic transducer (i.e., the ultrasonic emitter) can be fabricated using a piezoelectric material (e.g., quartz, berlinite, gallium, orthophosphate, $GaPO_4$, tourmalines, ceramics, barium, titanate, $BatiO_3$, lead zirconate, titanate PZT, zinc oxide, aluminum nitride, and polyvinylidene fluorides).

FIG. 24 shows another apparatus of this invention that includes a pressure detector for biological subject 2401. It includes at least one channel 2410 and whereon at least one piezoelectric detector 2420. When the biologic subject 2401 passes through the channel, the piezoelectric detector 2420 will detect the pressure of 2401, transform the information into an electrical signal, and send it out to a signal reader. Likewise, the trench width in the apparatus can be, e.g., from 1 nm to 1 mm, and the piezoelectric material can be, e.g., quartz, berlinite, gallium, orthophosphate, $GaPO_4$, tourmalines, ceramics, barium, titanate, $BatiO_3$, lead zirconate, titanate PZT, zinc oxide, aluminum nitride, or polyvinylidene fluorides.

FIG. 25 shows another apparatus of this invention that include a concave groove 2530 between a probe couple, in the bottom or ceiling of the channel. When a biological subject 2510 passes through, the concave 2530 can selectively trap the biological subject with particular geometric characteristics and makes the probing more efficiently. The shape of concave's projection can be rectangle, polygon, ellipse, or circle. The probe could detect electric, magnetic, electromagnetic, thermal, optical, acoustical, biological, chemical, physical, or mechanical properties. Similarly, the trench width can be, e.g., from 1 nm to 1 mm. FIG. 25(*a*) is an up-down view of this apparatus, FIG. 25(*b*) is a side view, whereas FIG. 25(*c*) is a perspective view.

FIG. 26 is another apparatus of this invention that also includes concave grooves 2630 (of a different shape from those shown in FIG. 25) on the bottom or ceiling of the channel. When a biological subject 2610 passes through, the concave grooves 2630 will generate a turbulent fluidic flow, which can selectively trap the micro-biological objects with particular geometric characteristics. The probe could detect electric, magnetic, electromagnetic, thermal, optical, acoustical, biological, chemical, physical, or mechanical properties. The depth of the concave groove can be, e.g., from 10 nm to 1 mm, and the channel width can be, e.g., from 1 nm to 1 mm.

FIG. 27 illustrated an apparatus of this invention with a stepped channel 2710. When a biological subject 2701 passes through the channel 2710, probe couples of different distances can be used to measure different microscopic properties, or even the same microscopic at different sensitivity at various steps (2720, 2730, 2740) with probe aside each step. This mechanism can be used in the phase lock-in application so that signal for the same microscopic property can be accumulated. The probes can detect or measure microscopic electric, magnetic, electromagnetic, thermal, optical, acoustical, biological, chemical, physical, or mechanical properties.

FIG. 28 illustrates another apparatus of this invention with thermal meters 2830. It includes a channel, a set of probes 2820, and a set of thermal meters 2830. The thermal meters 2830 can be an infrared sensor, a transistor sub-threshold leakage current tester, or thermister.

FIG. 29 illustrates a specific apparatus of this invention which includes carbon a nano-tube 2920 with a channel 2910 inside, probes 2940 which can detect microscopic electric, magnetic, electromagnetic, thermal, optical, acoustical, biological, chemical, physical, or mechanical properties. The carbon nano-tube 2920 as shown contains a double-helix DNA molecule 2930. The carbon nano-tube can force and sense electrical signals by the probes 2940 aside. The diameter of the carbon nano tube diameter can be, e.g., from 0.5 nm to 50 nm, and its length can range from, e.g., 5 nm to 10 mm FIG. 30 shows an integrated apparatus of this invention that includes a detecting device (shown in FIG. 30(*a*)) and an optical sensor (shown in FIG. 30(*b*)) which can be, e.g., a CMOS image sensor (CIS), a Charge-Coupled Device (CCD), a florescence light detector, or another image sensor. The detecting device comprises at least a probe and a channel, and the image device comprises at least 1 pixel. FIG. 30(*c*-1) and FIG. 30(*c*-2) illustrate the device with the detecting device and optical sensor integrated. As illustrated in FIG. 30(*d*), when biological subjects 3001, 3002, 3003 pass through, the probe 3010 in the channel 3020, its electric, magnetic, electromagnetic, thermal, optical, acoustical, biological, chemical, physical, or mechanical property could be detected by the probe 3010 (see FIG. 30(*e*)), meanwhile its image could be synchronously recorded by the optical sensor (FIG. 30(f)). Both the probed signal and image are combined together to provide a diagnosis and enhanced detection sensitivity and specificity. Such a detecting device and an optical sensing device can be designed in a system-on-chip or be packaged into one chip.

FIG. 31 shows an apparatus with a detecting micro-device (FIG. 31(a)) and a logic circuitry (FIG. 31(b)). The detecting device comprises at least a probe and a channel, and the logic circuitry comprises an addressor, an amplifier, and a RAM. When a biological subject 3101 passes through the channel, its property could be detected by the probe 3130, and the signal can be addressed, analyzed, stored, processed, and plotted in real time. FIG. 31(c-1) and FIG. 31(c-2) illustrate the device with detecting device and Circuitry integrated. Similarly, the detecting device and the integrated circuit can be designed in a System-on-Chip or be packaged into one chip.

FIG. 32 shows an apparatus of this invention that comprises a detecting device (FIG. 32(a)) and a filter (FIG. 32(b)). When a biological subject 3201 passes through the device, a filtration is performed in the filter, and irrelevant objects can be removed. The remaining subjects' property can then be detected by the probe device (FIG. 31(a)). The filtration before probing will enhance the precision of the device. The width of the channel can also range, e.g., from 1 nm to 1 mm.

FIG. 33 shows the geometric factors of DNA 3330 such as spacing in DNA's minor groove (3310) have an impact on spatial distribution of electrostatic properties in the region, which in turn may impact local biochemical or chemical reactions in the segment of this DNA. By probing, measuring, and modifying spatial properties of DNA (such as the spacing of minor groove) using the disclosed detector and probe 3320, one may detect properties such as defect of DNA, predict reaction/process at the segment of the DNA, and repair or manipulate geometric properties and therefore spatial distribution of electrostatic field/charge, impacting biochemical or chemical reaction at the segment of the DNA. For example, tip 3320 can be used to physically increase spacing of minor groove 3310.

FIG. 34 shows the fabrication process for a micro-device of this invention that has a flat cover atop of trench to form a channel. This will eliminate the need for coupling two trenches to form a channel, which can be tedious for requiring perfect alignment.

The cover can be transparent and allow observation with a microscope. It can comprise or be made of silicon, SiGe, $SiO_2$, various types of glass, or $Al_2O_3$.

While for the purposes of demonstration and illustration, the above cited novel, detailed examples show how microelectronics and/or nano-fabrication techniques and associated process flows can be utilized to fabricate highly sensitive, multi-functional, powerful, and miniaturized detection devices, the principle and general approaches of employing microelectronics and nano-fabrication technologies in the design and fabrication of high performance detection devices have been contemplated and taught, which can and should be expanded to various combination of fabrication processes including but not limited to thin film deposition, patterning (lithography and etch), planarization (including chemical mechanical polishing), ion implantation, diffusion, cleaning, various materials, combination of processes and steps, and various process sequences and flows. For example, in alternative detection device design and fabrication process flows, the number of materials involved can be fewer than or exceed four materials (which have been utilized in the above example), and the number of process steps can be fewer or more than those demonstrated process sequences, depending on specific needs and performance targets. For example, in some disease detection applications, a fifth material such as a biomaterial-based thin film can be used to coat a metal detection tip to enhance contact between the detection tip and a biological subject being measured, thereby improving measurement sensitivity.

Applications for the detection apparatus and methods of this invention include detection of diseases (e.g., in their early stage), particularly for serious diseases like cancer. Since cancer cell and normal cell differ in a number of ways including differences in possible microscopic properties such as electrical potential, surface charge, density, adhesion, and pH, novel micro-devices disclosed herein are capable of detecting these differences and therefore applicable for enhanced capability to detect diseases (e.g., for cancer), particularly in their early stage. In addition microdevices for measuring electrical potential and electrical charge parameters, micro-devices capable of carrying out mechanical property measurements (e.g., density) can also be fabricated and used as disclosed herein. In mechanical property measurement for early stage disease detection, the focus will be on the mechanical properties that likely differentiate disease or cancerous cells from normal cell. As an example, one can differentiate cancerous cells from normal cells by using a detection apparatus of this invention that is integrated with micro-devices capable of carrying out micro-indentation measurements.

FIG. 35 is a diagram of an apparatus of this invention for detecting a disease in a biological subject. This apparatus includes a pre-processing unit, a probing and detecting unit, a signal processing, and a disposal processing unit.

FIG. 36 shows an example of a sample filtration sub-unit in the pre-processing unit, which can separate the cells with different dimensions or sizes. This device comprises at least one entrance channel 3610, one disturbing fluid channel 3620, one accelerating chamber 3630, and two selecting channels (3640 and 3650). The angle 3660 between 3620 and 3610 ranges from 0° to 180°.

The biological subject 3601 flows in the x direction from the entrance channel 3610 to the accelerating chamber 3630. A bio-compatible fluid 3602 flows from disturbing fluid channel 3620 to the accelerating chamber 3630, it then accelerates the biological subject 3601 in the y-direction. The acceleration correlates with the radius of the biological subject and the larger ones are less accelerated than the smaller ones. Then, the larger and smaller subjects are separated into different selecting channels. Meanwhile, probes can be optionally assembled on the sidewalls of the channels 3610, 3620, 3630, 3640, and 3650. The probes could detect, at the microscopic level, electric, magnetic, electromagnetic, thermal, optical, acoustical, biological, chemical, biochemical, electro-mechanical, electro-chemical, electro-chemical-mechanical, physical, or mechanical properties.

FIG. 37 is a diagram of another example of a sample filtration unit in the apparatus of this invention. 3701 represents small cells, while 3702 represents large cells. When a valve 3704 is open and another valve 3703 is closed, biological subjects (3701 and 3702) flow towards exit A. Large cells that have larger size than the filtration hole are blocked against exit A, while small cells are flushed out through exit A. The entrance valve 3704 and exit A valve 3707 are then closed, and a bio-compatible fluid is injected through the fluid entrance valve 3706. The fluid carries big cells are flushed out from exit B. The larger cells are then analyzed and detected in the detection part of the invention.

FIG. 38 is a diagram of a pre-processing unit of an apparatus of this invention. This unit includes a sample filtration unit, a recharging unit or system for recharging nutrient or gas into the biological subject, a constant pressure delivery unit, and a sample pre-probing disturbing unit.

FIG. 39 is a diagram of an information or signal processing unit of an apparatus of this invention. This unit includes an amplifier (such as a lock-in amplifier) for amplifying the signal, an A/D converter, and a micro-computer (e.g., a device containing a computer chip or information processing sub-device), a manipulator, a display, and network connections.

FIG. 40 shows the integration of multiple signals which results in cancellation of noise and enhancement of signal/noise ratio. In this figure, a biological 4001 is tested by Probe 1 during Δt between t1 and t2, and by Probe 2 during Δt between t3 and t4. 4002 is 4001's tested signal from Probe 1, and 4003 is from Probe 2. Signal 4004 is the integration result from signal 4002 and 4003. The noise cancels out each other in certain extent and results in an improved signal strength or signal/noise ratio. The same principle can be applied to data collected from more than more than 2 micro-devices or probing units.

FIG. 41 shows one embodiment of the fabrication processes flow of this invention for manufacturing a detection device with at least one detection chamber and at least one detector. In this example, following an optional process flow of fabricating data storage, data processing and analyzing components (including transistors, memory devices, logic circuits, and RF devices), a material 4122 is first deposited onto a substrate 4111, followed by the deposition of another material 4133 (material for future detectors). Material 4133 can be selected from electrically conductive materials, piezo-electric materials, semiconductor materials, thermal sensitive materials, ion emission sensitive materials, pressure sensitive materials, mechanical stress sensitive materials, or optical materials. Optionally, it can also consist of composite materials or a desired material stack. If required, an integrated detector with a set of sub-components can be placed at this level. Material 4133 is next patterned using lithography and etch processes, forming a set of desired features shown in FIG. 41(c). Another material 4144 is subsequently deposited, which can be the same as or different from material 4122. Material 4122 can be an electrically insulating material such as oxide ($SiO_2$), doped oxide, silicon nitride, or polymer material. Next, the material 4144 is optionally planarized using polishing (e.g., using chemical mechanical polishing) or etch back process. The material stack is then patterned using lithography and etch processes, stopping on substrate 4111. Finally, as shown in FIG. 41(g), a capping layer or the surface of another component 4155 is placed on top of the material stack (thereby sealing or capping it), forming an enclosed detection chamber 4166 with detector 4177 for biological sample detection.

FIG. 42 illustrates another embodiment of the fabricating method of this invention for manufacturing a detection device with enclosed detection chambers, detectors, and channels for transporting biological samples such as fluidic samples. In this embodiment, following an optional process flow of fabricating data storage, data processing and analyzing components (including transistors, memory devices, logic circuits, and RF devices), a material 4222 is first deposited onto a substrate 4211, followed by the deposition of another material 4233 (material for future detectors). Material 4233 can be selected from electrical conductive materials, piezo-electric materials, semiconductor materials, thermal sensitive materials, ion emission sensitive materials, pressure sensitive materials, mechanical stress sensitive materials, or optical materials. Optionally, it can also include composite materials or a desired material stack. If required, an integrated detector with a set of sub-components can be placed at this level.

Materials 4222 and 4233 are subsequently patterned using lithography and etch processes (FIG. 42(c)). These two layers (4222 and 4233) can be patterned in separate patterning processes sequentially, or can be patterned in the same process, pending on device design, types of materials and etch chemistries. Substrate 4211 is next etched as shown in FIG. 42(d), forming a recessed area (cavity) in 4211, in which stacks 4222 and 4233 can be used as a hard mask during the etch process.

A material 4244 is deposited into the recessed area, and the portion of the material 4244 above the material 4233 is removed using a polishing (chemical or mechanical) or etch back process. Material 4244 can be selected from oxide, doped oxide, silicon nitride, and polymer materials. A layer 4255 is then deposited onto material 4244 and patterned to form small holes at selected locations. A wet or vapor etch is utilized next to remove material 4244, forming an enclosed detection chamber 4266.

Optionally, as shown in FIG. 42(i), the material 4222 is also removed using wet or vapor etch process, forming channels 4288 connecting various detection chambers, thus forming detection chambers with a detector 4277 lined with the walls of the detection chamber and with gaseous or fluidic biological samples flowing through the chambers. Finally, the top surface of the detection chamber is sealed with another layer of material (e.g., 4255).

FIG. 43 shows a novel disease detection method of this invention in which at least one probe object is launched at a desired speed and direction toward a biological subject, resulting in a collision. The response(s) by the biological subject during and/or after the collision is detected and recorded, which can provide detailed and microscopic information on the biological subject such as weight, density, elasticity, rigidity, structure, bonding (between different components in the biological subject), electrical properties such as electrical charge, magnetic properties, structural information, and surface properties. For example, for a same type of cell, it is expected that a cancerous cell will experience a smaller traveling distance after the collision than that of a normal cell due to its denser, greater weight, and possibly larger volume. As shown in FIG. 43(a), a probe object 4311 is launched towards a biological subject 4322. After the collision with the probe object 4311, the biological subject 4322 may be pushed (scattered) out a distance depending on its properties as shown FIG. 43(b).

FIG. 43(c) shows a schematic of a novel disease detection device with a probe object launch chamber 4344, an array of detectors 4333, a probe object 4322 and a biological subject to be tested 4311. In general, a test object can be an inorganic particle, an organic particle, a composite particle, or a biological subject itself. The launch chamber comprises a piston to launch the object, a control system interfaced to an electronic circuit or a computer for instructions, and a channel to direct the object.

FIG. 44 illustrates a novel fabrication process for forming multiple components with different materials at the same device level. First, a first material 4422 is deposited onto a substrate 4411 (see FIG. 44(a)), followed by the deposition of a second material 4433. The second material 4433 is next patterned to form at least a portion of recessed area in the layer 4433, using lithography and etch processes (see FIG. 44(c)). A third material 4444 is subsequently deposited. The third material can be the same as or different from the second material 4422.

The third material directly above the second material is removed via etch back and/or polishing (such as chemical mechanical polishing) processes (see FIG. 44(e)). Optionally, the third material is next patterned to form at least a portion of recessed area in layer 4444 (FIG. 44(f)). A fourth material 4455 is then deposited. Optionally, the portion of the fourth material 4455 directly above the third material 4444 or above both the second and third materials is removed via etch back and/or polishing (such as chemical mechanical polishing). The above process can keep repeating to form multiple features with the same or different materials at the same device level. Hence, this process flow forms at least two components 4466 and 4477 with different materials or the same materials at the same device level. For example, in one embodiment, one component can be used as a prober and the other can be used as a detector.

FIG. 45 illustrates a method for detecting a disease in a biological subject. A biological object 4501 passes through the channel 4531 at a speed v, and probe 4511 is a probe which can grossly detect the properties of the biological subject at high speed.

Probe 4512 is a fine probing device which is coated by a piezoelectric material. There is a distance ΔL between probe 4511 and probe 4512.

When the biological subjects are tested when getting through 4511, if the entity is identified to be a suspected abnormal one, the system would trigger the piezoelectric probe 4512 to stretch into the channel and probe particular properties after a time delay of Δt. And probe 4512 retracts after the suspected entity passed through.

The probing device is capable of measuring at the microscopic level an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property of the biological subject.

The width of the micro-channel can range from about 1 nm to about 1 mm.

FIG. 46 shows a process of detecting a disease in a biological subject. A biological subject 4601 passes through the channel 4631 at a speed v. Probe 4611 is a probe which can grossly detect the properties of the biological subject at high speed. 4621 and 4622 are piezoelectric valves to control the micro-channel 4631 and 4632. 4612 is a fine probing device which can probe biological properties more particularly. 4631 is flush channel to rush out normal biological subjects. 4632 is detection channel where the suspected entities are fine detected in this channel.

When a biological subject is tested while getting through 4611, if it is normal, the valve 4621 of the flush channel is open, while the detection channel valve 4622 is closed, the biological subject is flushed out without a time-consuming fine detection.

When the biological subject is tested while getting through 4611, if it is suspected to be abnormal or diseased, the valve 4621 of the flush channel is closed, while the detection channel valve 4622 is open, the biological subject is conducted to the detection channel for a more particular probing.

The width of the micro-channel can range from about 1 nm to about 1 mm.

The probing device is capable of measuring at the microscopic level an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property of the biological subject.

FIG. 47 illustrates an arrayed biological detecting device. 4701 are arrayed micro-channels which can get through the fluidics and biological subjects. 4702 are probing devices embedded aside the channels. The sensors are wired by bit-lines 4721 and word-lines 4722. The signals are applied and collected by the decoder R\row-select 4742 and decoder column select 4741. As illustrated in FIG. 47-b, the micro-channel arrayed biological detecting device 4700 can be embedded in a macro-channel 4701. The micro-channel's dimension ranges from about 1 um to about 1 mm. The shape of the micro-channel can be rectangle, ellipse, circle, or polygon.

The probing device is capable of measuring at the microscopic level an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property of the biological subject.

FIG. 48 illustrates a device of the current invention for disease detection. 4801 is inlet of the detecting device, and 4802 is the outlet of the device. 4820 is the channel where the biological subjects pass through. 4811 is the optical component of the detecting device.

As illustrated in FIG. 48(b), the optical component 4811 consists of an optical emitter 4812 and an optical receiver 4813. The optical emitter emits an optical pulse (e.g. laser beam pulse), when the biological subject 4801 passing through the optical component, and the optical sensor detects the diffraction of the optical pulse, then identify the morphology of the entity.

The width of the micro-channel can range from about 1 nm to about 1 mm.

Although specific embodiments of this invention have been illustrated herein, it will be appreciated by those skilled in the art that any modifications and variations can be made without departing from the spirit of the invention. The examples and illustrations above are not intended to limit the scope of this invention. Any combination of detection apparatus, micro-devices, fabrication processes, and applications of this invention, along with any obvious their extension or analogs, are within the scope of this invention. Further, it is intended that this invention encompass any arrangement, which is calculated to achieve that same purpose, and all such variations and modifications as fall within the scope of the appended claims.

All publications referred to above are incorporated herein by reference in their entireties. All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example of a generic series of equivalent or similar features.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All publications referenced herein are incorporated by reference in their entireties.

What is claimed is:

1. A detection apparatus, comprising a detection device fabricated by a method comprising:
providing a substrate;
sequentially depositing a first material and a second material as two layers onto the substrate to form a material stack;
patterning the second material to form a first desired feature;
depositing a third material onto the material stack to cover the second material;
polishing or etch back the third material to planarize the third material;
patterning the first material and third material to form a second desired feature; and
optionally depositing a fourth material onto the material stack,
wherein the first desired feature comprises a feature selected from the group consisting of probe generator, detection probe, electrically connective interconnection line, optional transmission line, and piezo-electric line; and the second desired feature comprises a feature selected from the group consisting of partitioned chamber, channel, and chamber connected with channel,
wherein the detection device comprises at least one pair of probe generator and detection probe supported by the substrate, wherein at least one of the probe generator or the detection probe is included by the first desired feature,
wherein the probe generator applies a signal onto a biological subject, thereby stimulating the biological subject and causing it to have a response signal; wherein the biological subject comprises a liquid sample of blood, urine, sweat, or saliva, which further comprises one or more cells, proteins, or DNAs;
wherein the probe generator comprises a micro-injector or conductive tip, and the probe generator applies the signal onto the biological subject by delivering a biochemical material or applying a voltage to the biological subject; or by piercing the cell or interacting with grooves of the DNA;
wherein the detection probe contacts the biological subject and directly measures at the microscopic level the response signal from the biological subject; wherein when the biological subject travels in a certain direction in the detection device, the detection takes place after the biological subject travels a distance from the probing function.

2. The apparatus of claim 1, wherein the detection device is capable of interacting with the biological subject to generate the response signal as an electric, magnetic, electromagnetic, thermal, optical, acoustical, biological, chemical, electro-mechanical, electro-chemical, electro-chemical-mechanical, bio-chemical, bio-chemical-physical, physical-chemical, bio-physical, bio-physical mechanical, bio-mechanical, bio-electro-mechanical, bio-electro-chemical, bio-electro-chemical-mechanical, physical, or mechanical property; and the apparatus is capable of measuring the response signal at the microscopic level.

3. The apparatus of claim 2, wherein the electric property is surface charge, surface potential, resting potential, action potential, electrical voltage, electrical current, electrical field distribution, electrical charge distribution, electric dipole, electric quadruple, three-dimensional electrical or charge cloud distribution, electrical properties at telomere of DNA and chromosome, dynamic changes in electrical properties, dynamic changes in potential, dynamic changes in surface charge, dynamic changes in current, dynamic changes in electrical field, dynamic changes in electrical voltage, dynamic changes in electrical distribution, dynamic changes in electronic cloud distribution, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, oxygen concentration, oxygen consumption rate, ionic strength, catalytic behavior, or bonding strength; the physical property is density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

4. The apparatus of claim 1, wherein the second material is patterned by microelectronic processes.

5. The apparatus of claim 1, wherein the first material and third material can be the same or different.

6. The apparatus of claim 1, wherein the fabrication method further comprises capping the top of the material stack to form an enclosed trench, wherein the enclosed trench is an enclosed channel or chamber.

7. The apparatus of claim 6, wherein the enclosed trench can be used to transport the biological subject.

8. The apparatus of claim 6, wherein the capping comprises placing a second device on the top of the material stack, and the second device can be a device identical to the detection device being capped, a piece of glass or crystal, or a functional device selected from the group consisting of an imaging device, an optical detector, a sensor, a memory storage, a logic processing component, a circuit for data storage, signal transmitter, and signal processing unit.

9. The apparatus of claim 1, wherein the thickness of the fourth material is thinner than that of the third material.

10. The apparatus of claim 1, further comprising a pre-processing unit with additional chambers for pre-screening, additional channels for carrying fluidic sample to flow through, additional probes for probing and disturbing the biological subject being tested for generating additional response signals, additional detection probes for measuring the generated response signals of the biological subject, and an imaging device, a camera, a viewing station, an acoustic detector, an optical detector, an electrical signal detector, a thermal detector, an ion emission detector, or a thermal recorder for observing and recording properties and behaviors of the biological subject, a memory storage, a signal transmitter, a logic processing component, a circuit for data storage, or a signal processing unit.

11. The apparatus of claim 1, wherein an additional device is fabricated by microelectronics processes on the substrate where the first material is deposited.

12. The apparatus of claim 1, wherein the first desired feature comprises the probe generator or the detection probe; and the second desired feature comprises the channel.

13. The apparatus of claim 1, wherein the partitioned chamber is for pre-processing of the biological subject for initial screening, the chamber connected with channel is for pre-processing and detection, the channel is for the biological subject to flow through, the probe generator is for generating the signal onto the biological subject for triggering the response signal, the detection probe is for measuring properties of the biological subject and the response signal, the electrically connective interconnection line is for transmitting the signal or the response signal.

14. The apparatus of claim 1, wherein the channel is a square-shaped channel having a dimension ranging from about 2 microns×2 microns to about 100 microns×100 microns in cross sectional area, or a circular shaped channel having a radius ranging from about 1 micron to about 20 microns in cross sectional area for a circular shaped channel; the detection probe or the probe generator has a dimension ranging from about 0.5 micron×0.5 micron to about 20 microns×20 microns in cross sectional area for a square-shaped probe.

15. The apparatus of claim 1, wherein the first material and the third material each comprise a material selected from the group consisting of un-doped silicon oxide ($SiO_2$), doped oxide, silicon nitride, a polymer material, glass, and an insulating material.

16. The apparatus of claim 1, wherein the second material comprises a material selected from the group consisting of an electrically conductive material, a thermal sensitive material, an optical material, an ion emission sensitive material, aluminum, an aluminum alloy, copper, a copper alloy, tungsten, a tungsten alloy, gold, a gold alloy, silver, a silver alloy, and a piezo-electric material; wherein the optical material comprises an anisotropic optical material, glass, glass-ceramic, laser gain media, nonlinear optical material, phosphor and scintillator, or transparent material.

17. The apparatus of claim 16, wherein the piezo-electric material is quartz, berlinite, gallium, orthophosphate, $GaPO_4$, tourmaline, ceramics, barium, titanate, $BatiO_3$, lead zirconate, titanate PZT, zinc oxide, aluminum nitride, or a polyvinylidene fluoride.

18. The apparatus of claim 1, wherein the first material and third material can be the same or different.

19. The apparatus of claim 18, wherein the fabrication method further comprises capping the top of the material stack to form an enclosed trench, wherein the enclosed trench is an enclosed channel or chamber.

20. The apparatus of claim 19, wherein the capping comprises sealing or capping the top of the material stack with an imaging device, a sensor, an optical detector, a camera, a viewing station, an acoustic detector, an optical detector, an electrical detector, a thermal detector, an ion emission detector, or a thermal recorder onto the material stack.

21. The apparatus of claim 18, further comprising a pre-processing unit for pre-screening, additional channels for carrying fluidic sample to flow through, additional probes for probing and disturbing the biological subject being tested for generating additional response signals, additional detection probes for measuring the generated response signals of the biological subject, or an imaging device for observing and recording properties and behaviors of the biological subject.

22. The apparatus of claim 18, wherein the first and the third materials each comprises a material selected from the group consisting of un-doped silicon oxide ($SiO_2$), doped oxide, silicon nitride, a polymer material, glass, or an insulating material; and the second material comprises an electrically conductive material, aluminum, an aluminum alloy, copper, a copper alloy, tungsten, a tungsten alloy, gold, a gold alloy, silver, a silver alloy, a piezo-electric material, a thermal sensitive material, an optical material, or an ion emission sensitive material; and the piezo-electric material is quartz, berlinite, gallium, orthophosphate, $GaPO_4$, tourmaline, ceramics, barium, titanate, $BatiO_3$, lead zirconate, titanate PZT, zinc oxide, aluminum nitride, and a polyvinylidene fluoride; wherein the optical material comprises an anisotropic optical material, glass, glass-ceramic, laser gain media, nonlinear optical material, phosphor and scintillator, or transparent material.

23. A detection apparatus, comprising a detection device fabricated by a method comprising:
    providing a substrate;
    sequentially depositing a first material and a second material as two layers onto the substrate to form a material stack;
    patterning the second material by microelectronic processes selective to the first material to create at least a portion of recessed area in the layer of the second material;
    depositing a third material onto the material stack to cover the second material;
    removing a portion of the third material above the second material by etch back or polishing process;
    optionally patterning the third material by microelectronic processes to form at least a portion of recessed area in the layer of the third material;
    depositing a fourth material onto the material stack;
    optionally removing a portion of the fourth material above both the second and third materials by etch back or polishing process; and
    optionally depositing a fifth material;
    optionally patterning the fifth material to form trenches;
    optionally covering the material stack with a plate or another device,
    wherein the detection device comprises at least one probe and at least one detector, wherein the probe and the detector are supported by the substrate, and at least one of the probe and the detector is formed by said step of patterning the second material or the fourth material,
    wherein the probe applies a signal onto a biological subject, thereby stimulating the biological subject and causing it to have a response signal;
    wherein the probe comprises a micro-injector or conductive tip, and the probe applies the signal onto the biological subject by delivering a biochemical material or applying a voltage to the biological subject; or by piercing the cell or interacts with grooves of the DNA;
    wherein the detector contacts the biological subject and directly measures at the microscopic level the response signal from the biological subject; wherein when the biological subject travels in a certain direction in the detection device, the detection takes place after the biological subject travels a distance from the probing function.

24. The apparatus of claim 23, wherein the second material and fourth material can be the same or different.

25. The apparatus of claim 23, wherein the third material is patterned by microelectronic processes to form the portion of recessed area in the layer of the third material; the portion of the fourth material above both the second and third materials is removed by etch back or polishing process; and the fifth material is deposited and then patterned to form the trenches.

26. The apparatus of claim 23, wherein the second material is patterned using lithography and etch processes selective to the first material to create the portion of the recessed area in the layer of the second material; or the second material is patterned to form the probe capable of probing or disturbing the biological subject.

27. The apparatus of claim 23, wherein the fourth material is patterned by a chemical mechanical polishing process or an etch back process to stop on the second and third materials to form the detector capable of detecting response signal from the biological subject; or is patterned to form a second probe using polishing, etch back, or both polishing and etch back.

28. The apparatus of claim 23, wherein the fifth material is patterned to form the trenches, and the trenches comprise channels where a fluidic sample can flow through during disease detection with probes aligned along the bottoms of the channels.

29. The apparatus of claim 23, wherein the fabrication method further comprises placing another device on top of the above material stack to further form an enclosed trench; capping the top of the material stack to further form an enclosed trench; or fabricating a sensor, a memory storage, a signal transmitter, a logic processing component, a circuit for data storage, or signal processing unit on the substrate using microelectronics technologies.

30. The apparatus of claim 23, wherein the capping comprises placing another device on the top of the material stack, and the other device can be a device identical to the device being capped, a piece of glass or crystal, or a functional device selected from the group consisting of an imaging device, a sensor, a memory storage, a signal transmitter, a logic processing component, a circuit for data storage, and signal processing unit.

31. The apparatus of claim 23, wherein the microelectronic processes comprise a process selected from the group consisting of thin film deposition, lithography, etch, polishing, cleaning, ion implantation, diffusion, and packaging.

32. The apparatus of claim 23, wherein the third material is patterned by a chemical or mechanical polishing process or by an etch back process to stop on the second material; or by a lithography and etch processes selective to the first and second materials to remove at least a portion the third material, optionally, while protecting the second material during the patterning processes.

33. The apparatus of claim 23, wherein the fourth material is patterned by a chemical or mechanical polishing process or by an etch back process to form a second detector.

34. The apparatus of claim 23, wherein the fifth material is patterned using lithography and etch processes.

35. The apparatus of claim 34, wherein the fifth material is patterned to form the trenches, and the trenches comprise at least a channel or at least a detection chamber where a fluidic sample can flow through during disease detection with probes aligned along the walls of the channels.

36. The apparatus of claim 23, wherein the fabrication method further comprises placing another device on top of the material stack to further form an enclosed trench, capping the top of the material stack to further form an enclosed trench, or fabricating a memory storage, a sensor, a signal transmitter, a logic processing component, or a circuit for data storage, or signal processing unit on the substrate using microelectronics technologies.

37. The apparatus of claim 36, wherein the capping comprises placing another device on the top of the material stack, and the other device can be a device identical to the device being capped, a piece of glass or crystal, or a functional device selected from the group consisting of an imaging device, a sensor, a memory storage, a logic processing component, a circuit for data storage, signal transmitter, and signal processing unit.

38. The apparatus of claim 23, wherein the detector is capable of measuring at the microscopic level an electric, magnetic, electromagnetic, thermal, optical, acoustical, biological, chemical, physical-chemical, bio-physical, bio-physical-chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property of the biological subject.

39. The apparatus of claim 38, wherein the electric property is surface charge, surface potential, resting potential, action potential, electrical voltage, electrical current, electrical field distribution, electrical charge distribution, electric dipole, electric quadruple, three-dimensional electrical or charge cloud distribution, electrical properties at telomere of DNA and chromosome, dynamic changes in electrical properties, dynamic changes in potential, dynamic changes in surface charge, dynamic changes in current, dynamic changes in electrical field, dynamic changes in electrical voltage, dynamic changes in electrical distribution, dynamic changes in electronic cloud distribution, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, oxygen concentration, oxygen consumption rate, ionic strength, catalytic behavior, or bonding strength; the physical property is density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

40. A detection apparatus, comprising a detection device and a channel or chamber fabricated by a method comprising:
provide a substrate;
optionally patterning the substrate to form at least a recessed area;
depositing material A onto the substrate to cover at least the substrate's optional recessed area;
planarizing material A to remove at least part of it from above the substrate and leaving material A at least in the substrate's optional recessed area;
depositing material B onto material A and optionally the recessed area of the substrate;
patterning material B to form at least a recessed area;
depositing material X onto material B to cover material B and its recessed area;
patterning material X to form at least a hole smaller than material B's recessed area above material B's recessed area;
removing at least part of material B and at least part of material A by wet etch, plasma etch, or vapor etch to form the channel or chamber between material X and the substrate or material A; and
depositing material Y to seal the at least one small hole in material X,
wherein the detection device is capable of measuring at the microscopic level a property of a biological subject by a detector formed by material B;
wherein material B comprises an electrically conductive material, a piezo-electric material, a semiconductor material, a thermal sensitive material, an optical material; a pressure sensitive material, an ion emission sensitive material, or any combination thereof; wherein the optical material comprises an anisotropic optical material, glass, glass-ceramic, laser gain media, nonlinear optical material, phosphor and scintillator, or transparent material.

41. The apparatus of claim 40, wherein the detector is capable of measuring at the microscopic level an electric, magnetic, electromagnetic, thermal, optical, acoustical, biological, chemical, physical-chemical, bio-physical, biophysical-chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property of the biological subject.

42. The apparatus of claim 41, wherein the electric property is surface charge, surface potential, resting potential, action potential, electrical voltage, electrical current, electrical field distribution, electrical charge distribution, electric dipole, electric quadruple, three-dimensional electrical or charge cloud distribution, electrical properties at telomere of DNA and chromosome, dynamic changes in electrical properties, dynamic changes in potential, dynamic changes in surface charge, dynamic changes in current, dynamic changes in electrical field, dynamic changes in electrical voltage, dynamic changes in electrical distribution, dynamic changes in electronic cloud distribution, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, oxygen concentration, oxygen consumption rate, ionic strength, catalytic behavior, or bonding strength; the physical property is density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

43. The apparatus of claim 40, wherein all the recessed areas overlap; and optionally material A comprises an electrically insulating material and material B comprises an electrically conductive material, a piezo-electric material, a semiconductor material, a thermal sensitive material, an optical material; a pressure sensitive material, an ion emission sensitive material, or any combination thereof; wherein the optical material comprises an anisotropic optical material, glass, glass-ceramic, laser gain media, nonlinear optical material, phosphor and scintillator, or transparent material.

44. The apparatus of claim 40, where the fabricating method further comprises:
after patterning material B and before depositing material X, depositing material C onto material B to cover at least the recessed area of material B;
optionally planarizing material C; and
patterning material C to form at least a recessed area that overlaps with the recessed area of material B;
wherein material C can be the same or different from material A.

45. The apparatus of claim 44, wherein material C comprises an electrically insulating material, an electrically conductive material, a piezo-electric material, a semiconductor material, a thermal sensitive material, an optical material; a pressure sensitive material, or an ion emission sensitive material; wherein the optical material comprises an anisotropic optical material, glass, glass-ceramic, laser gain media, nonlinear optical material, phosphor and scintillator, or transparent material.

46. The apparatus of claim 44, wherein all the recessed areas overlap; and optionally material C comprises an electrically insulating material, an electrically conductive material, a piezo-electric material, a semiconductor material, a thermal sensitive material, an optical material, a pressure sensitive material, or an ion emission sensitive material; wherein the optical material comprises an anisotropic optical material, glass, glass-ceramic, laser gain media, nonlinear optical material, phosphor and scintillator, or transparent material.

47. The apparatus of claim 46, where the fabricating method further comprises:
after patterning material C and before depositing material X, depositing material D onto material C to cover at least the recessed area of material C; and
removing material D above material C and leaving material D in the recessed area of material C;
wherein material D can be the same or different from material B.

48. The apparatus of claim 46, where the fabricating method further comprise, after patterning material C and before depositing material X, depositing material E onto material D to cover at least the recessed area of material D; and removing material E above material D and leaving material E in the recessed area of material D; and optionally repeating the steps of depositing an additional material onto at least a recessed area and removing the additional material above the recessed area and leave the additional material in the recessed area.

49. The apparatus of claim 48, wherein all the recessed areas overlap.

50. The apparatus of claim 40, further comprising a micro-injector for injecting an object into the biological subject to generate a response, and response is measured by the detector.

51. An apparatus comprising two micro-devices each fabricated by the method comprising:
providing a substrate,
depositing a first material onto a substrate;
depositing a second material onto the first material and then patterning the second material by microelectronic processes; and
repeating the second step at least once with a third material that can be the same as or different from the first or second material, wherein the two micro-devices each comprise a conductive tip, and the two micro-devices can simultaneously pierce through the membrane of a cell and can move in different directions in order to stretch the cell.

52. The apparatus of claim 51, wherein the micro-devices each are capable of measuring at the microscopic level at least an electric, magnetic, electromagnetic, thermal, optical, acoustical, biological, chemical, physical-chemical, electro-mechanical, electro-chemical, electro-chemical-mechanical, bio-chemical, bio-physical, bio-physical mechanical, physical-chemical, bio-mechanical, bio-electro-mechanical, bio-electro-chemical, bio-electro-chemical-mechanical, physical, or mechanical property of the cell or cell membrane.

53. The apparatus of claim 51, wherein the fabricated micro-devices are physically or electrically coupled or integrated.

54. The apparatus of claim 51, wherein the microelectronic processes comprise thin film deposition, lithography, etch, polishing, cleaning, ion implantation, diffusion, or packaging.

55. The apparatus of claim 51, wherein the apparatus is integrated on a single device or assembled on a single board.

56. A method for fabricating a device, wherein the device comprises a micro-device, and the micro-device further comprises a micro-trench having sidewalls and a probe embedded in the micro-trench's sidewalls, wherein the probe comprises a detecting tip, and wherein the method comprises:
providing a substrate;
depositing a first material onto the substrate;
depositing a second material onto the first material and then patterning the second material by a microelectronic process to form the detecting tip;
depositing a third material on the second material and then patterning the third material by a planarization process;
depositing a fourth material on the third material and patterning the fourth material by microelectronic processes;
patterning the third material using a microelectronic process with the fourth material serving as a hardmask.

57. The method of claim 56, wherein the microelectronic process comprises lithography, etch process, direct writing, molecular self assembly, laser ablation, electron beam writing, x-ray writing, diffusion, ion implantation, cleaning, polishing, planarization by chemical mechanical polishing, and packaging.

58. The method of claim 56, further comprising removal of a stack of multiple layers of materials by wet etch, dry etch, or vapor etch.

59. The method of claim 56, wherein the third or fourth material can be the same as or different from the first or second material.

60. The method of claim 56, wherein the micro-device can move in any direction.

61. The method of claim 56, wherein at least one of the materials used in fabricating the micro-device is a biological material, a polymer, a piezo-electric material, a semiconductor material, an electrically insulating material, or an electrically conductive material.

62. The apparatus of claim 61, wherein the piezo-electric material is quartz, berlinite, gallium, orthophosphate, $GaPO_4$, tourmaline, ceramics, barium, titanate, $BatiO_3$, lead zirconate, titanate PZT, zinc oxide, aluminum nitride, or a polyvinylidene fluoride.

63. The method of claim 56, wherein the micro-device is capable of sorting, probing, measuring, communicating, or modifying a biological subject.

64. The method of claim 56, wherein the microelectronic processes comprise thin film deposition, lithography, etch, polishing, cleaning, ion implantation, diffusion, or packaging.

65. The method of claim 56, further comprising fabricating an additional micro-device, and coupling the two micro-devices together.

66. The method of claim 65, wherein the shape of each channel's cross-section is rectangle, ellipse, circle, or polygon.

67. The method of claim 65, wherein the micro-trenches of the coupled two micro-devices are aligned by module of alignment marks designed on the layout of the micro-device.

68. The method of claim 56, wherein the micro-trench has a dimension ranging from about 0.1 um to about 500 um.

69. The method of claim 56, further comprises integrating three or more micro-devices together.

70. The method of claim 69, further comprising covering the micro-trench of the micro-device with a flat panel, wherein the flat panel comprises a material selected from the group consisting of silicon, SiGe, $SiO_2$, $Al_2O_3$, acrylate polymer, AgInSbTe, synthetic alexandrite, arsenic triselenide, arsenic trisulfide, barium fluoride, CR-39, cadmium selenide, caesium cadmium chloride, calcite, calcium fluoride, chalcogenide glass, gallium phosphide, GeSbTe, germanium, germanium dioxide, glass code, hydrogen silsesquioxane, Iceland spar, liquid crystal, lithium fluoride, lumicera, METATOY, magnesium fluoride, magnesium oxide, negative index metamaterials, neutron super mirror, phosphor, picarin, poly(methyl methacrylate), polycarbonate, potassium bromide, sapphire, scotophor, spectralon, speculum metal, split-ring resonator, strontium fluoride, yttrium aluminum garnet, yttrium lithium fluoride, yttrium orthovanadate, ZBLAN, zinc selenide, and zinc sulfide.

71. The method of claim 56, further comprising:
before depositing the second material, patterning the first material by a microelectronic process to give rise to at least one patterned residual and leaving part of the substrate surface uncovered by the first material;
creating an opening in the second material to expose part of the patterned residual of the first material; and
filling up the opening in the second material with the third material;
wherein the second material is a non-electrically conductive material.

72. The method of claim 71, wherein the microelectronic processes comprise a process selected from the group consisting of thin film deposition, lithography, etch, polishing, cleaning, ion implantation, diffusion, and packaging.

73. A method for fabricating a micro-device, comprising:
providing a substrate;
sequentially depositing a first material and a second material as two layers onto the substrate to form a material stack;
patterning the second material by microelectronic processes to form a first desired feature;
depositing a third material onto the material stack to cover the second material and optionally the first material;
optionally patterning the first and third materials by microelectronic processes to form a second desired feature; and
optionally depositing a fourth material onto the material stack,
wherein the first desired feature is a detection probe capable of applying a probing or disturbing signal onto a biological subject to result in a response signal from the biological subject, wherein the biological subject comprises a liquid sample of blood, urine, sweat, or saliva, which further comprises one or more cells, proteins, or DNAs; wherein the detection probe comprises a micro-injector or a conductive tip, and the detection probe applies the probing or disturbing signal by delivering a biochemical material or applying a voltage to the biological subject, or by piercing the cell or interacting with grooves of the DNA to generate the response signal,
wherein the second desired feature is a recessed form, or a trench form in the layers of the third and first materials, wherein the trench form is a trench or a channel,
wherein the second material is an electrically conductive material, a piezo-electric material, a semiconductor material, a thermal sensitive material, a magnetic material, a pressure sensitive material, a mechanical stress sensitive material, an ion emission sensitive material, a optical material, or a combination thereof; wherein the optical material comprises an anisotropic optical material, glass, glass-ceramic, laser gain media, nonlinear optical material, phosphor and scintillator, or transparent material.

74. The method of claim 73, further comprising fabricating at least an additional component onto the substrate before sequentially depositing the first material and the second material as layers onto the substrate, wherein the additional component comprises a data storage component, a signal processing component, a memory storage component, a signal receiver, a signal transmitting component, a logic processing component, or an RF component.

75. The method of claim 73, wherein the microelectronic processes comprise a process selected from the group consisting of thin film deposition, lithography, etch, polishing, cleaning, ion implantation, diffusion, and packaging.

76. The method of claim 73, wherein the first material and the third material are the same.

77. The method of claim 76, wherein the first material and the third material are electrically insulating.

78. The method of claim 76, wherein the first material or the third material is oxide, doped oxide, silicon nitride, or a polymer.

79. The method of claim 73, wherein the second material comprises a material selected from the group consisting of copper, aluminum, tungsten, gold, silver, alloys thereof, and glass.

80. The method of claim 73, wherein the second material is aligned with a wall of the trench form in the layers of the third and first materials.

81. The method of claim 73, further comprising capping the top of the material stack to cover the third material and form the enclosed trench.

82. The method of claim 81, wherein the capping comprises sealing or capping the top of the material stack with a layer of material, an imaging device, a camera, a viewing station, an acoustic detector, a thermal detector, an ion emission detector, or a thermal recorder onto the material stack.

83. The method of claim 73, wherein the second material can be the same as or different from the third material, the second material is patterned by microelectronic process to form at least a portion of the recessed area in the layer of the second material; and the method further comprises:
optionally planarizing the third material by chemical mechanical polishing process, an etch process, or a combination thereof to stop on the second material;
patterning the third material by microelectronic processes to remove at least a portion of the third material;
depositing a fourth material onto the material stack; and
patterning the fourth material and first material by microelectronic processes to form the channel; wherein the channel is used to deliver the biological subject passing through.

84. The method of claim 83, further comprising fabricating at least an additional component onto the substrate before sequentially depositing the first material and the second material as layers onto the substrate, wherein the additional component comprises a data storage component, a signal processing component, a memory storage component, a signal transmitting component, a logic processing component, or an RF component, a signal transmitting component, a logic processing component, or an RF component; or fabricating at least a circuit onto the substrate before sequentially depositing the first material and the second material as layers onto the substrate, wherein the circuit comprises a data storage circuit, a signal processing circuit, a memory storage circuit, a sensor, a signal transmitting circuit, or a logic processing circuit.

85. The method of claim 83, further comprising planarizing the third material using a chemical mechanical polishing process or an etch back process after depositing the third material onto the material stack and before patterning the first and the third materials.

86. The method of claim 83, further comprising planarizing the third material using a chemical mechanical polishing process or an etch back process.

87. The method of claim 83, wherein the microelectronic processes comprise a process selected from the group consisting of thin film deposition, lithography, etch, polishing, cleaning, ion implantation, diffusion, and packaging.

88. The method of claim 83, wherein the first material and the fourth material are the same.

89. The method of claim 88, wherein the first material or fourth material is un-doped oxide, doped oxide, silicon nitride, polymer material, or glass.

90. The method of claim 83, wherein the second material and the third material are the same.

91. The method of claim 90, wherein the second material or the third material is an electrical conductive material, a magnetic material, an electro-magnetic material, an optical material, a thermal sensitive material, a pressure sensitive material, an ion emission sensitive material, or a piezoelectric material; wherein the optical material comprises an anisotropic optical material, glass, glass-ceramic, laser gain media, nonlinear optical material, phosphor and scintillator, or transparent material.

92. The method of claim 91, wherein the second material or the third material is aluminum, copper, tungsten, gold, silver, the alloys thereof, quartz, berlinite, gallium, orthophosphate, $GaPO_4$, tourmalines, ceramics, barium, titanate, $BatiO_3$, lead zirconate, titanate PZT, zinc oxide, aluminum nitride, or polyvinylidene fluoride.

93. The method of claim 83, wherein the detection probe is aligned with the wall of the channel.

94. The method of claim 91, further comprising patterning the fourth material to form a hole at a selected location after depositing the fourth material onto the material stack.

95. The method of claim 83, further comprising removing the third material from the material stack by wet or vapor etch to form a detection chamber between the fourth material and the substrate, or removing the first material from the material stack by wet or vapor etch to form the channel.

96. The method of claim 95, wherein the channel connects the detection chamber with at least an additional detection chamber.

97. The method of claim 83, further comprising capping the top of the material stack to form an enclosed trench or channel; sealing or capping the top of the material stack with a fifth material to form the enclosed channel; or sealing or capping the top of the material stack with an imaging devices, a detector, an optional sensor, a camera, a viewing station, an acoustic detector, a thermal detector, an electrical detector, an ion emission detector, or a thermal recorder onto the material stack.

98. A method for fabricating a device for detecting at the microscopic level a property of a biological subject, comprising:
providing a substrate;

sequentially depositing a first and a second materials as layers onto the substrate to form a material stack;

patterning the second material by microelectronic processes to form at least a portion of a recessed area in the second material depositing a third material onto the material stack to cover the second material, and removing a portion of the third material above the second material by etch back or polishing process;

patterning the third material by lithography and etch processes to remove at least an additional portion of the third material; and depositing a fourth material onto the material stack to cover the second and third material, and removing portion of the fourth material above the second and third material by etch back or polishing process; and optionally, depositing a fifth material and repeating the above process sequence used for the third material, wherein at least a detector is formed by the second material or the fourth material, and optionally a probe or an integrated unit with sub-component for detection is further formed by the second material or the fourth material;

wherein the second or the fourth material is electrical conductive material, semiconductor material, piezo-electric material, thermal sensitive material, an ion emission sensitive material, a magnetic material, a pressure sensitive material, a mechanical stress sensitive material, or optical material; wherein the optical material comprises an anisotropic optical material, glass, glass-ceramic, laser gain media, nonlinear optical material, phosphor and scintillator, or transparent material.

99. The method of claim 98, further comprising fabricating at least an additional component onto the substrate before sequentially depositing the first material and the second material as layers onto the substrate, wherein the additional component is selected from the group consisting of a data storage component, a signal processing component, a memory storage component, a signal transmitting component, a logic processing component, and an RF component.

100. The method of claim 98, wherein the substrate is silicon, polysilicon, silicon nitride, or polymer material.

101. The method of claim 98, wherein the first material is oxide, doped oxide, silicon nitride, or polymer material.

102. The method of claim 98, wherein the second and the fourth material are the same.

103. The method of claim 102, wherein the second and the fourth materials are electrical conductive material, semiconductor material, piezo-electric material, thermal sensitive material, an ion emission sensitive material, a magnetic material, a pressure sensitive material, a mechanical stress sensitive material, or optical material; wherein the optical material comprises an anisotropic optical material, glass, glass-ceramic, laser gain media, nonlinear optical material, phosphor and scintillator, or transparent material.

* * * * *